(12) United States Patent
Angst et al.

(10) Patent No.: US 8,791,100 B2
(45) Date of Patent: Jul. 29, 2014

(54) ARYL BENZYLAMINE COMPOUNDS

(75) Inventors: Daniela Angst, Basel (CH); Birgit Bollbuck, Weil am Rhein (DE); Philipp Janser, Basel (CH); Jean Quancard, Basel (CH); Nikolaus Johannes Stiefl, Lörrach (DE)

(73) Assignee: Novartis AG, Basel (CH)

( * ) Notice: Subject to any disclaimer, the term of this patent is extended or adjusted under 35 U.S.C. 154(b) by 772 days.

(21) Appl. No.: 13/015,919

(22) Filed: Jan. 28, 2011

(65) Prior Publication Data

US 2011/0190258 A1 Aug. 4, 2011

Related U.S. Application Data

(60) Provisional application No. 61/300,607, filed on Feb. 2, 2010.

(51) Int. Cl.
| | |
|---|---|
| A61K 31/192 | (2006.01) |
| A61K 31/397 | (2006.01) |
| A61K 31/40 | (2006.01) |
| A61K 31/4439 | (2006.01) |
| A61K 31/4427 | (2006.01) |
| C07D 401/06 | (2006.01) |
| C07D 205/04 | (2006.01) |
| C07D 207/12 | (2006.01) |
| C07C 53/134 | (2006.01) |

(52) U.S. Cl.
USPC ...... 514/210.17; 514/423; 514/340; 514/343; 514/570; 548/953; 548/532; 546/279.1; 546/268.1; 562/442

(58) Field of Classification Search
None
See application file for complete search history.

(56) References Cited

U.S. PATENT DOCUMENTS

| 6,310,078 B1 | 10/2001 | Connolly et al. |
|---|---|---|
| 7,655,396 B1 | 2/2010 | Kedzie et al. |
| 2005/0101644 A1 | 5/2005 | Davey et al. |
| 2006/0057559 A1 | 3/2006 | Xu et al. |
| 2008/0108077 A1 | 5/2008 | Chissoe |
| 2008/0260719 A1 | 10/2008 | Liao et al. |

FOREIGN PATENT DOCUMENTS

| DE | 19846979 A1 | 9/1998 |
|---|---|---|
| DE | 10028901 A1 | 10/2000 |
| EP | 1090925 A1 | 4/2001 |
| EP | 1524265 A1 | 4/2005 |
| EP | 1661881 A2 | 5/2006 |
| WO | 91/15583 A1 | 10/1991 |
| WO | 98/50549 A2 | 11/1998 |
| WO | 00/11166 A1 | 3/2000 |
| WO | 00/22131 A2 | 4/2000 |
| WO | 00/31258 A2 | 6/2000 |
| WO | 00/59529 A1 | 10/2000 |
| WO | 01/04139 A2 | 1/2001 |
| WO | 01/66742 A2 | 9/2001 |
| WO | 01/70954 A3 | 9/2001 |
| WO | 01/73021 A1 | 10/2001 |
| WO | 01/81573 A1 | 11/2001 |
| WO | 02/06446 A2 | 1/2002 |
| WO | 02/17899 A2 | 3/2002 |
| WO | 03/013551 A1 | 2/2003 |
| WO | 03/062252 A1 | 7/2003 |
| WO | 03/087063 A1 | 10/2003 |
| WO | 2004/009816 A1 | 1/2004 |
| WO | 2004/026823 A1 | 4/2004 |
| WO | 2004/035538 A1 | 4/2004 |
| WO | 2005/014532 A1 | 2/2005 |
| WO | 2005/028667 A1 | 3/2005 |
| WO | 2006/014802 A2 | 2/2006 |
| WO | 2006/058316 A1 | 6/2006 |
| WO | 2007/048042 A2 | 4/2007 |
| WO | 2007/139946 A2 | 12/2007 |
| WO | 2009/053481 A1 | 4/2009 |
| WO | 2009/071947 A2 | 6/2009 |
| WO | 2009/103778 A1 | 8/2009 |
| WO | 2009/137081 A2 | 11/2009 |
| WO | 2010/072712 A1 | 7/2010 |

OTHER PUBLICATIONS

Library compounds: Structures: RN 1156678-01-1, RN 1156677-94-9, RN 1156612-22-4, RN 1155512-87-0, RN 1154318-37-2, RN 1154318-25-8, RN 1125428-05-8, RN 617709-33-8 (2003).

*Primary Examiner* — Michael Barker
(74) *Attorney, Agent, or Firm* — Sophie Binet Cross

(57) ABSTRACT

The present invention relates to substituted aryl-benzylamine compounds, to processes for their production, to their use as pharmaceuticals and to pharmaceutical compositions comprising them.

16 Claims, No Drawings

ARYL BENZYLAMINE COMPOUNDS

This application claims benefit under 35 U.S.C. §119(e) of U.S. Provisional Application No. 61/300,607, filed Feb. 2, 2010; the contents of which are incorporated herein by reference in their entirety.

The present invention relates to substituted aryl-benzylamine compounds, to processes for their production, to their use as pharmaceuticals and to pharmaceutical compositions comprising them. The compounds of formula (I) in free form or in pharmaceutically acceptable salt form, exhibit valuable pharmacological properties, for example for preventing or treating diseases or disorders which are mediated by lymphocyte interactions, or for example as S1P receptor modulators, e.g. S1P1 receptor antagonists and hence are useful for therapy susceptible thereto.

More particularly, the present invention provides a compound of formula (I) or a salt thereof;

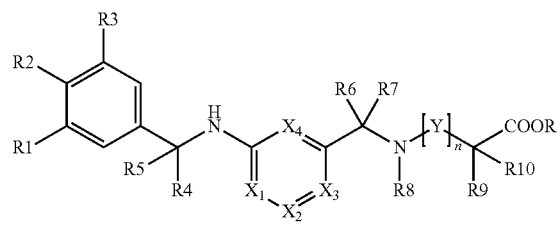

(I)

wherein,
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_8$ alkoxy optionally substituted by halogen;
or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl or they may form together with the carbon atom to which they are attached a 3-7 membered saturated carbocyclic ring;
R8 and R9 are independently selected from H and $C_1$-$C_6$ alkyl, or they may form together with the atoms to which they are attached a 4-7 membered heterocyclic ring optionally substituted one or more times by $C_1$-$C_6$-alkyl optionally substituted by halogen, trifluoromethyl, hydroxy, $C_1$-$C_6$ alkoxy, amino;
n=1, 2, 3 or 4;
R10 is hydrogen, $C_1$-$C_6$ alkyl, amino, hydroxy, or $C_1$-$C_6$ alkoxy;
R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl optionally substituted by $C_1$-$C_6$ alkyl, $C_1$-$C_6$ alkoxy, halogen or hydroxy,
$X_1$, $X_2$, $X_3$ and $X_4$, are each independently selected from N or CR11,
R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and
Y stands in each occurrence independently for CR12R13 wherein R12 and R13 are independently selected from H and $C_1$-$C_6$ alkyl.

In another embodiment the invention provides a compound of formula (II) or a salt thereof,

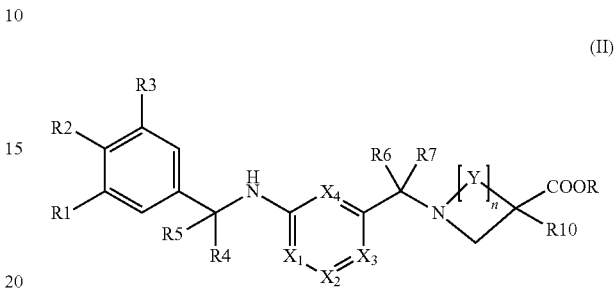

(II)

wherein
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy optionally substituted by halogen;
or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl, or they may form together with the carbon atom to which they are attached a 3-7 membered saturated carbocyclic ring;
n=1, 2, 3 or 4;
R10 is hydrogen, $C_1$-$C_6$ alkyl, amino, hydroxy, or $C_1$-$C_6$ alkoxy;
R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl, said phenyl being optionally substituted by $C_1$-$C_6$ alkyl, $C_1$-$C_6$ alkoxy, halogen or hydroxy;
$X_1$, $X_2$, $X_3$ and $X_4$, are each independently selected from N or CR11,
R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and
Y stands in each occurrence independently for CR12R13 wherein R12 and R13 are independently selected from H and $C_1$-$C_6$ alkyl optionally substituted by halogen.

With regard to a compound of formula (I) and/or formula (II), to the extent the substituents can be present in a corresponding formula, the following significances represent further embodiments of the invention independently, collectively or in any combination or in any sub-combination thereof:
1. R1 is H or methyl;
2. R2 is chloro;
3. R1 and R3 are both methyl;

4. R3 is methyl;
5. R4 is methyl or $C_1$-$C_6$ alkyl optionally substituted by halogen, or R4 is in particular trifluoromethyl;
6. R5 is H;
7. R6 is H;
8. R7 is H;
9. R8 is H or methyl; in particular H;
10. R8 and R9 form together with the atoms to which they are attached a 5 membered heterocyclic ring;
11. R10 is H, methyl or ethyl;
12. R10 is hydrogen;
13. R11 is H;
14. R11 is methyl;
15. R11 is chloro or cyano;
16. R12 is H;
17. R13 is H;
18. $X_3$ and $X_4$, are each CR11 and R11 stands for methyl;
19. $X_3$ stands for N;
20. Y stands for $CH_2$;
21. R is H;
22. n stands for 1 or 2, especially 2;
23. $X_3$ is CR11 and R11 stands for methyl;
24. R2 is chloro and R3 is methyl;
25. R2 is chloro, R3 is methyl and R4 is trifluoromethyl;
26. $X_1$ stands for N;
27. $X_1$, $X_2$, $X_3$ and $X_4$, are each independently CR11
28. R1 and R2 together with the C-atoms to which they are attached form an aryl ring with 6-10 carbon atoms, especially phenyl, naphthyl or tetrahydronaphthyl, which may optionally be substituted by 1-4 substituents selected from cyano, $C_1$-$C_4$-alkyl optionally substituted by halogen, $C_1$-$C_4$-alkoxy optionally substituted by halogen, and halogen;

In another embodiment the invention provides compounds in accordance to formula (I) and or formula (II) or a salt thereof wherein R1 and R stand for hydrogen, wherein the other variables are as defined above.

In another embodiment the invention provides compounds in accordance to formula (I) and or formula (II) or a salt thereof wherein n is 2, and wherein the other variables are as defined above.

In another embodiment the invention provides compounds in accordance to formula (I) and or formula (II) or a salt thereof wherein any of $X_3$ and $X_4$ are each CR11 and wherein R11 stands for methyl, wherein the other variables are as defined above.

In another embodiment the invention provides compounds in accordance to formula (I) and or formula (II) or a salt thereof wherein $X_3$ is CR11 and wherein R11 stands for methyl, wherein the other variables are as defined above.

In another embodiment the invention provides compounds in accordance to formula (I) and or formula (II) or a salt thereof wherein R4 is trifluoromethyl and R5 is hydrogen, wherein the other variables are as defined above.

In another embodiment the invention provides compounds in accordance to formula (I) and or formula (II) or a salt thereof wherein R2 is chloro, R3 is methyl, R4 is trifluoromethyl and R is hydrogen, wherein the other variables are as defined above.

In another embodiment the invention provides compounds in accordance to formula (I) and or formula (II) or a salt thereof wherein $X_1$, $X_2$, $X_3$ and $X_4$, are each independently CR11, R11 is hydrogen, R2 is chloro, R3 is methyl, R4 is trifluoromethyl and R is hydrogen, wherein the other variables are as defined above.

In another embodiment the invention provides compounds in accordance to formula (I) and or formula (II) or a salt thereof wherein $X_1$, $X_2$, $X_3$ and $X_4$, are each independently CR11, R11 is hydrogen, R2 is chloro, R3 is methyl, R4 is trifluoromethyl, R is hydrogen, and n=2, and wherein the other variables are as defined above.

In another embodiment the invention provides compounds in accordance to formula (I) and or formula (II) or a salt thereof wherein $X_1$, $X_2$, $X_3$ and $X_4$, are each independently CR11, R11 is hydrogen, R2 is chloro, R3 is methyl, R4 is trifluoromethyl, R is hydrogen, n=2, R6 is hydrogen, R7 is hydrogen, and wherein the other variables are as defined above.

In another embodiment individual compounds according to the invention are those described in the Examples section below.

In another embodiment the invention provides any one of compounds in accordance to the working examples 1-87 as described in the experimental section or a pharmaceutically acceptable salt thereof.

In another embodiment the invention provides any one of compounds in accordance to the working examples 1-87 as described in the experimental section or a pharmaceutically acceptable salt thereof as a racemate or as a diastereomeric mixture as applicable, in each case.

In another embodiment the invention provides a compound of the formula (I), which is selected from:
1-{3-[1-(4-Chloro-3-methyl-phenyl)-ethylamino]-benzyl}-azetidine-3-carboxylic acid,
1-{3-[1-(4-Chloro-3-methyl-phenyl)-propylamino]-benzyl}-azetidine-3-carboxylic acid,
1-{3-[(R)-1-(4-Chloro-3-methyl-phenyl)-propylamino]-benzyl}-azetidine-3-carboxylic acid,
1-{5-[1-(4-Chloro-3-methyl-phenyl)-propylamino]-2-methyl-benzyl}-azetidine-3-carboxylic acid,
1-{3-[1-(4-Chloro-3-methyl-phenyl)-propylamino]-4-methyl-benzyl}-azetidine-3-carboxylic acid,
1-(1-{3-[(R)-1-(4-Chloro-3-methyl-phenyl)-propylamino]-phenyl)-ethyl}azetidine-3-carboxylic acid,
1-{3-[1-(4-Chloro-3-methyl-phenyl)-propylamino]-2-methyl-benzyl}-azetidine-3-carboxylic acid,
1-{3-[(R)-1-(4-Chloro-3-methyl-phenyl)-propylamino]-benzyl}-3-methyl-azetidine-3-carboxylic acid,
1-{3-[1-(4-Chloro-3-methyl-phenyl)-propylamino]-5-methyl-benzyl}-azetidine-3-carboxylic acid,
1-(1-{5-[1-(4-Chloro-3-methyl-phenyl)-propylamino]-2-methyl-phenyl}-ethyl)-azetidine-3-carboxylic acid,
(R)-1-{3-[(R)-1-(4-Chloro-3-methyl-phenyl)-propylamino]-benzyl}-pyrrolidine-3-carboxylic acid,
(S)-1-{3-[(R)-1-(4-Chloro-3-methyl-phenyl)-propylamino]-benzyl}-pyrrolidine-3-carboxylic acid,
1-(1-(3-[(R)-1-(4-Chloro-3-methyl-phenyl)-propylamino]-phenyl}-propyl)-azetidine-3-carboxylic acid,
(R)-1-{3-[1-(4-Chloro-3-methyl-phenyl)-propylamino]-2-methyl-benzyl}-pyrrolidine-3-carboxylic acid,
(R)-1-{3-[1-(4-Chloro-3-methyl-phenyl)-propylamino]-5-methyl-benzyl}-pyrrolidine-3-carboxylic acid,
1-{3-[(R)-1-(4-Chloro-3-methyl-phenyl)-propylamino]-benzyl}-3-ethyl-azetidine-3-carboxylic acid,
1-{3-[1-(4-Chloro-3-methyl-phenyl)-2-methyl-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(5-Chloro-naphthalen-2-yl)-propylamino]-benzyl}-azetidine-3-carboxylic acid, (R)-1-{5-[(S)-1-(4-Chloro-3-methyl-phenyl)-2,2,2-trifluoro-ethylamino]-2-methyl-benzyl}-pyrrolidine-3-carboxylic acid,
1-{5-[(R)-1-(4-Chloro-3-methyl-phenyl)-propylamino]-2-methyl-benzyl}-azetidine-3-carboxylic acid,
(R)-1-{5-[(R)-1-(4-Chloro-3-methyl-phenyl)-propylamino]-2-methyl-benzyl}-pyrrolidine-3-carboxylic acid,
1-{3-[(R)-1-(4-Chloro-3-methyl-phenyl)-propylamino]-2-fluoro-benzyl}-azetidine-3-carboxylic acid,
(R)-1-{3-[(R)-1-(4-Chloro-3-methyl-phenyl)-propylamino]-2-fluoro-benzyl}-pyrrolidine-3-carboxylic acid,
1-{3-[(R)-1-(4-Chloro-3-methyl-phenyl)-propylamino]-4-fluoro-benzyl}-azetidine-3-carboxylic acid,
(R)-1-{3-[(R)-1-(4-Chloro-3-methyl-phenyl)-propylamino]-4-fluoro-benzyl}-pyrrolidine-3-carboxylic acid,
1-{5-[(R)-1-(4-Chloro-3-methyl-phenyl)-propylamino]-2-methyl-benzyl}-3-methyl-azetidine-3-carboxylic acid,
(R)-1-{2-Chloro-5-[(S)-1-(4-chloro-3-methyl-phenyl)-2,2,2-trifluoro-ethylamino]-benzyl}-pyrrolidine-3-carboxylic acid,
(R)-1-{3-[(S)-1-(4-Chloro-3-methyl-phenyl)-2,2,2-trifluoro-ethylamino]-2,6-dimethyl-benzyl}-pyrrolidine-3-carboxylic acid,
1-{3-[(S)-1-(4-Chloro-3-methyl-phenyl)-2,2,2-trifluoro-ethylamino]-2,6-dimethyl-benzyl}-azetidine-3-carboxylic acid,
(R)-1-{3-[(R)-1-(4-Chloro-3-methyl-phenyl)-propylamino]-2,6-dimethyl-benzyl}-pyrrolidine-3-carboxylic acid,
1-{3-[(R)-1-(4-Chloro-3-methyl-phenyl)-propylamino]-2,6-dimethyl-benzyl}-azetidine-3-carboxylic acid,
(R)-1-{5-[(S)-1-(4-Chloro-3-methyl-phenyl)-2,2,2-trifluoro-ethylamino]-2-ethyl-benzyl}-pyrrolidine-3-carboxylic acid,
1-{5-[(S)-1-(4-Chloro-3-methyl-phenyl)-2,2,2-trifluoro-ethylamino]-2-ethyl-benzyl}-azetidine-3-carboxylic acid,
(R)-1-{5-[(R)-1-(4-Chloro-3-methyl-phenyl)-propylamino]-2-ethyl-benzyl}-pyrrolidine-3-carboxylic acid,
1-{5-[(R)-1-(4-Chloro-3-methyl-phenyl)-propylamino]-2-ethyl-benzyl}-azetidine-3-carboxylic acid,
(R)-1-{2-Chloro-5-[(R)-1-(4-chloro-3-methyl-phenyl)-propylamino]-benzyl}-pyrrolidine-3-carboxylic acid,
1-{3-[(S)-1-(4-Chloro-3-methyl-phenyl)-2,2,2-trifluoro-ethylamino]-2-methyl-benzyl}-azetidine-3-carboxylic acid,
3-{3-[(S)-1-(4-Chloro-3-methyl-phenyl)-2,2,2-trifluoro-ethylamino]-2,6-dimethyl-benzylamino}-propionic acid,
1-{5-[(R)-1-(4-Chloro-3,5-dimethyl-phenyl)-propylamino]-2-methyl-benzyl}-azetidine-3-carboxylic acid,
(R)-1-{5-[(R)-1-(4-Chloro-3,5-dimethyl-phenyl)-propylamino]-2-methyl-benzyl}-pyrrolidine-3-carboxylic acid,
(R)-1-{2-Chloro-5-[(R)-1-(4-chloro-3,5-dimethyl-phenyl)-propylamino]-benzyl}-pyrrolidine-3-carboxylic acid,
(R)-1-{5-[(R)-1-(4-Chloro-3,5-dimethyl-phenyl)-ethylamino]-2-methyl-benzyl}-pyrrolidine-3-carboxylic acid,
3-{5-[(R)-1-(4-Chloro-3,5-dimethyl-phenyl)-propylamino]-2-methyl-benzylamino}-propionic acid,
(R)-1-{2-Chloro-5-[(R)-1-(4-chloro-3,5-dimethyl-phenyl)-ethylamino]-benzyl}-pyrrolidine-3-carboxylic acid,
3-{5-[(R)-1-(4-Chloro-3,5-dimethyl-phenyl)-ethylamino]-2-methyl-benzylamino}-propionic acid,
3-{2-Chloro-5-[(R)-1-(4-chloro-3,5-dimethyl-phenyl)-propylamino]-benzylamino}-propionic acid,
(R)-3-{5-[(R)-1-(4-Chloro-3,5-dimethyl-phenyl)-propylamino]-2-methyl-benzylamino}-2-methyl-propionic acid,
3-{5-[(S)-1-(4-Chloro-3,5-dimethyl-phenyl)-2,2,2-trifluoro-ethylamino]-2-methyl-benzylamino}-propionic acid, 3-{2-Chloro-5-[(S)-1-(4-chloro-3,5-dimethyl-phenyl)-2,2,2-trifluoro-ethylamino]-benzylamino}-propionic acid,
3-{2-Chloro-5-[(S)-1-(4-chloro-3-methyl-phenyl)-2,2,2-trifluoro-ethylamino]-benzylamino}-propionic acid,
3-{2-Chloro-5-[(R)-1-(4-chloro-3,5-dimethyl-phenyl)-propylamino]-benzylamino}-propionic acid,
1-{2-[(R)-1-(4-Chloro-3-methyl-phenyl)-propylamino]-5-fluoro-pyridin-4-ylmethyl}-azetidine-3-carboxylic acid,
(R)-1-{5-Chloro-2-[(R)-1-(4-chloro-3-methyl-phenyl)-propylamino]-pyridin-4-ylmethyl}-pyrrolidine-3-carboxylic acid,
(R)-1-{5-[(R)-1-(4-Chloro-3-methyl-phenyl)-propylamino]-2-methyl-pyridin-3-ylmethyl}-pyrrolidine-3-carboxylic acid,
1-{5-Chloro-2-[(R)-1-(4-chloro-3-methyl-phenyl)-propylamino]-pyridin-4-ylmethyl}-3-methyl-pyrrolidine-3-carboxylic acid,
3-({5-Chloro-2-[(R)-1-(4-chloro-3-methyl-phenyl)-propylamino]-pyridin-4-ylmethyl}-amino)-propionic acid,
(R)-1-{5-Chloro-2-[(R)-1-(4-chloro-3,5-dimethyl-phenyl)-propylamino-]-pyridin-4-ylmethyl}-pyrrolidine-3-carboxylic acid,
(R)-1-{2-[(R)-1-(4-Chloro-3-methyl-phenyl)-propylamino]-5-methyl-pyridin-4-ylmethyl}-pyrrolidine-3-carboxylic acid,
1-{2-Chloro-5-[(R)-1-(4-chloro-3,5-dimethyl-phenyl)-propylamino]-benzyl}-azetidine-3-carboxylic acid,
1-{2-Chloro-5-[(R)-1-(4-chloro-3-methyl-phenyl)-propylamino]-benzyl}-azetidine-3-carboxylic acid,
1-{2-Chloro-5-[(R)-1-(4-chloro-3-methyl-phenyl)-2-methyl-propylamino]-benzyl}-azetidine-3-carboxylic acid,
1-{2-Chloro-5-[(R)-1-(4-chloro-3,5-dimethyl-phenyl)-2-methyl-propylamino]-benzyl}-azetidine-3-carboxylic acid,
1-{2-Chloro-5-[(S)-1-(4-chloro-3-methyl-phenyl)-2,2,2-trifluoro-ethylamino]-benzyl}-3-methyl-azetidine-3-carboxylic acid,
1-{2-Chloro-5-[(R)-1-(4-chloro-3,5-dimethyl-phenyl)-propylamino]-benzyl}-3-methyl-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{5-[(S)-1-(4-Chloro-3-methyl-phenyl)-2,2,2-trifluoro-ethylamino]-2-trifluoromethyl-benzyl}-azetidine-3-carboxylic acid,
1-{5-[(S)-1-(4-Chloro-3-methyl-phenyl)-2,2,2-trifluoro-ethylamino]-2-methyl-benzyl}-azetidine-3-carboxylic acid,
1-{5-[(S)-1-(4-Chloro-3-methyl-phenyl)-2,2,2-trifluoro-ethylamino]-2-fluoro-benzyl}-azetidine-3-carboxylic acid,
1-{2-Chloro-5-[(S)-1-(4-chloro-3-methyl-phenyl)-2,2,2-trifluoro-ethylamino]-benzyl}-pyrrolidine-3-carboxylic acid,
3-((S)-1-{3-[(S)-1-(4-Chloro-3-methyl-phenyl)-2,2,2-trifluoro-ethylamino]-phenyl}-ethylamino)-propionic acid
1-{6-[(R)-1-(4-Chloro-3-methyl-phenyl)-propylamino]-pyridin-2-ylmethyl}-azetidine-3-carboxylic acid,
1-{2-[(R)-1-(4-Chloro-3-methyl-phenyl)-propylamino]-pyridin-4-ylmethyl}-azetidine-3-carboxylic acid,
1-(3-{[(R)-(4-Chloro-3-methyl-phenyl)-cyclobutyl-methyl]-amino}-benzyl)-azetidine-3-carboxylic acid,
1-(3-{[(S)-(4-Chloro-3-methyl-phenyl)-cyclobutyl-methyl]-amino}-benzyl)-azetidine-3-carboxylic acid,
1-{4-[(R)-1-(4-Chloro-3-methyl-phenyl)-propylamino]-pyridin-2-ylmethyl}-azetidine-3-carboxylic acid, 1-{5-Chloro-2-[(R)-1-(4-chloro-3-methyl-phenyl)-propylamino]-pyridin-4-ylmethyl}-azetidine-3-carboxylic acid, 3-{5-[(R)-1-(4-Chloro-3,5-dimethyl-phenyl)-propylamino]-2-methyl-benzylamino}-2,2-dimethyl-propionic acid, (S)-3-{5-[(R)-1-(4-Chloro-3,5-dimethyl-phenyl)-propylamino]-2-methyl-benzylamino}-2-methyl-propionic acid, 3-({5-[(R)-1-(4-Chloro-3,5-dimethyl-phenyl)-propylamino]-2-methyl-benzyl}-methyl-amino)-propionic acid, 1-{5-[(S)-1-(4-Chloro-3-methyl-phenyl)-2,2,2-trifluoro-ethylamino]-2-methyl-benzyl}-3-methyl-pyrrolidine-3-carboxylic acid, (R)-1-{5-Chloro-2-[(S)-1-(4-chloro-3-methyl-phenyl)-2,2,2-trifluoro-ethylamino]-pyridin-4-ylmethyl}-pyrrolidine-3-carboxylic acid, 3-({5-Chloro-2-[(S)-1-(4-chloro-3-methyl-phenyl)-2,2,2-trifluoro-ethylamino]-pyridin-4-ylmethyl}-amino)-propionic acid, 1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer A), and 1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer B).

As used herein "alkyl" may be a linear or branched hydrocarbon moiety having 1 to 20 carbon atoms. Unless otherwise provided, alkyl refers to hydrocarbon moieties having 1 to 16 carbon atoms, 1 to 10 carbon atoms, 1 to 6 carbon atoms, or 1 to 4 carbon atoms. $C_1$-$C_6$ alkyl represents, for example: methyl, ethyl, propyl, butyl, isopropyl, isobutyl, tertiary butyl, 2,2-dimethylpropyl, n-pentyl, neo-pentyl, n-hexyl, isohexyl and the like.

As used herein "cycloalkyl" represents a cyclic hydrocarbon containing from 3 to 12 ring atoms preferably from 3 to 6 ring atoms. Cycloalkyl represents, for example: cyclopropyl, cyclobutyl, cyclopentyl, or cyclohexyl. A cycloalkyl may optionally be substituted by $C_1$-$C_6$ alkyl, trifluoromethyl, $C_3$-$C_6$ cycloalkyl, halogen, hydroxy, $C_1$-$C_6$ alkoxy, acyl, $C_1$-$C_6$ alkyl-C(O)—O—, aryl-O—, heteroaryl-O—, amino, thiol, $C_1$-$C_6$ alkyl-S—, aryl-S—, nitro, cyano, carboxy, $C_1$-$C_6$ alkyl-O—C(O)—, carbamoyl, $C_1$-$C_6$ alkyl-S(O)—, sulfonyl, sulfonamido, or phenyl.

As used herein acyl is a radical $R_dCO$ wherein $R_d$ is H, $C_{1-6}$alkyl, $C_{3-6}$cycloalkyl, $C_{3-6}$cycloalkyloxy, $C_{1-6}$alkoxy, phenyl, phenyloxy, benzyl or benzyloxy; in particular acyl is $C_{1-6}$alkyl-CO, $C_{1-6}$alkoxy-CO, benzyloxy-CO or benzyl-CO; especially acyl is $C_{1-6}$alkyl-CO or $C_{1-4}$alkoxy-CO, particularly $C_{1-4}$alkyl-CO, $C_{1-4}$alkoxy-CO, t-butoxycarbonyl or acetyl ($CH_3CO$).

As used herein, the term "alkoxy" refers to alkyl-O—, wherein alkyl is defined herein above. An alkoxy group may be branched or unbranched. $C_1$-$C_6$ alkoxy represents, for example: methoxy, ethoxy, propoxy, butoxy, isopropoxy, isobutoxy or tertiary butoxy. Alkoxy includes $C_3$-$C_6$ cycloalkyloxy and $C_3$-$C_6$ cycloalkyl—$C_1$-$C_6$ alkyloxy.

Halo or halogen represents chloro, fluoro, bromo or iodo. Preferably halo or halogen represents chloro or fluoro.

Alkyl as defined herein may be substituted by one or more halo groups as defined herein and may also be named haloalkyl. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Alkyl is for example $C_1$-$C_6$ alkyl, and halo is for example fluoro and/or chloro.

Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

Alkoxy as defined herein may be substituted by one or more halo groups as defined herein. Alkoxy substituted by halo may be monohaloalkoxy, dihaloalkoxy, trihaloalkoxy or polyhaloalkoxy. A monohaloalkoxy may have one iodo, bromo, chloro or fluoro within the alkoxy group. Dihaloalkoxy and polyhaloalkoxy groups can have two or more of the same halo atoms or a combination of different halo groups within the alkoxy. Alkoxy is for example $C_1$-$C_5$ alkoxy, and halo is for example fluoro and/or chloro. Non-limiting examples of haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy.

The term "aryl" refers to an aromatic hydrocarbon group having 5-20 carbon atoms in the ring portion. Typically, aryl is monocyclic, bicyclic or tricyclic aryl having 5-20 carbon atoms, also monocyclic or bicyclic having from 6-10 carbon atoms.

Furthermore, the term "aryl" as used herein, refers to an aromatic substituent which can be a single aromatic ring, or multiple aromatic rings that are fused together. The term "aryl" further refers to an aromatic ring as defined herein substituted with 1 to 5 substituents independently selected from the groups consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, trifluoromethyl, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, carbamoyl, sulfonyl, sulfamoyl, alkylsulfamoyl, $C_1$-$C_4$-alkylaminosulfonyl.

Non-limiting examples include phenyl, naphthyl or tetrahydronaphthyl, each of which may optionally be substituted by 1-4 substituents, such as hydroxyl, cyano, $C_1$-$C_4$-alkyl, trifluoromethyl, $C_1$-$C_4$-alkenyl, $C_1$-$C_4$-alkynyl, $C_1$-$C_4$-alkoxy, halogen, $C_1$-$C_4$-alkylcarbonyl, carboxy, $C_1$-$C_4$-alkoxycarbonyl, carbamoyl, sulfonyl, sulfamoyi, alkylsulfamoyl, $C_1$-$C_4$-alkylaminosulfonyl.

Further non-limiting examples include phenyl, naphthyl or tetrahydronaphthyl, which may optionally be substituted by 1-4 substituents selected from cyano, $C_1$-$C_4$-alkyl, $C_1$-$C_4$-alkoxy, and halogen.

As used herein, the term "heterocyclyl" or "heterocyclo" or "heterocyclic ring" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl may include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrrolidine, pyrrolidine, tetrahydropyran, dihydropyran, oxathiolane, dithiolane, 1,3-dioxane, 1,3-dithiane, oxathiane, thiomorpholine, and the like.

The term "heterocyclyl" further refers to heterocyclic groups as defined herein substituted with 1 to 5 substituents independently selected from the groups consisting of $C_1$-$C_6$-alkyl, trifluoromethyl, $C_3$-$C_6$ cycloalkyl, halogen, hydroxy, $C_1$-$C_6$ alkoxy, acyl, $C_1$-$C_6$ alkyl-C(O)—O—, aryl-O—, heteroaryl-O—, amino, thiol, $C_1$-$C_6$ alkyl-S—, aryl-S—, nitro, cyano, carboxy, $C_1$-$C_6$ alkyl-O—C(O)—, carbamoyl, $C_1$-$C_6$ alkyl-S(O)—, sulfonyl, sulfonamido, and phenyl. "Heterocyclyl" may be optionally substituted one or more times by $C_1$-$C_6$-alkyl, trifluoromethyl, $C_3$-$C_6$ cycloalkyl, halogen, hydroxy, $C_1$-$C_6$ alkoxy, acyl, $C_1$-$C_6$ alkyl-C(O)—O—, aryl-O—, heteroaryl-O—, amino, thiol, $C_1$-$C_6$ alkyl-S—, aryl-S—, nitro, cyano, carboxy, $C_1$-$C_6$ alkyl-O—C(O)— or carbamoyl, especially optionally substituted one or more times by $C_1$-$C_6$-alkyl, trifluoromethyl, $C_3$-$C_6$ cycloalkyl, halogen, hydroxy, $C_1$-$C_6$ alkoxy, or acyl.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 membered bicycle) or a 5-7 membered ring system. The term "heteroaryl" may further refer to heteroaryl groups as defined herein substituted with 1 to 5 substituents independently selected from the groups consisting of hydroxyl, thiol, cyano, nitro, $C_1$-$C_4$-alkyl, $C_1$-$C_4$-alkenyl, $C_1$-$C_4$-alkynyl, $C_1$-$C_4$-alkoxy, $C_1$-$C_4$-thioalkyl, $C_1$-$C_4$-alkenyloxy, $C_1$-$C_4$-alkynyloxy, halogen, $C_1$-$C_4$-alkylcarbonyl, carboxy, $C_1$-$C_4$-alkoxycarbonyl, amino, $C_1$-$C_4$-alkylamino, di-$C_1$-$C_4$-alkylamino, $C_1$-$C_4$-alkylaminocarbonyl, di-$C_1$-$C_4$-alkylaminocarbonyl, $C_1$-$C_4$-alkylcarbonylamino, $C_1$-$C_4$-alkylcarbonyl($C_1$-$C_4$-alkyl)amino, carbamoyl, sulfonyl, sulfamoyl, alkylsulfamoyl, and $C_1$-$C_4$-alkylaminosulfonyl.

Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl, which may be optionally substituted by 1 to 4 substituents selected from hydroxyl, cyano, $C_1$-$C_4$-alkyl, $C_1$-$C_4$-alkenyl, $C_1$-$C_4$-alkynyl, $C_1$-$C_4$-alkoxy, halogen, $C_1$-$C_4$-alkyl carbonyl, carboxy, $C_1$-$C_4$-alkoxycarbonyl, carbamoyl, sulfonyl, sulfamoyl, alkylsulfamoyl, and $C_1$-$C_4$-alkylaminosulfonyl.

As used herein, the term "aryloxy" refers to an —O-aryl wherein aryl is defined herein.

As used herein, the term "heteroaryloxy" refers to an —O-heteroaryl group, wherein heteroaryl is defined herein.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of for example a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S). The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable effective. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen, phosphate/dihydrogen, phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^3H$, $^{13}C$, and $^{14}C$, are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by lymphocytes interactions or sphingosine-1-phosphate receptors, or (ii) associated with lymphocytes interactions or sphingosine-1-phosphate receptors activity, or (iii) characterized by activity (normal or abnormal) of lymphocytes interactions or sphingosine-1-phosphate receptors; or (2) reducing or inhibiting the activity of lymphocytes interactions or sphingosine-1-phosphate receptors. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of lymphocytes interactions or sphingosine-1-phosphate receptors.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is in need of a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Synthesis of the Compounds of the Invention

Compounds of the invention may be prepared by the reaction sequences outlined and described below for Schemes 1, 2, 3 and/or 4 and hence these represent further embodiments of the invention, i.e. for preparing a compound according to formula (I) and/or formula (II) as defined above.

Compounds of the invention may be prepared by a reaction sequence involving for example a reductive amination of an appropriate nitro-benzaldehyde with an appropriate amine, reduction of the aromatic nitro group, and reductive amination of the aniline with an appropriate ketone followed by a deprotection step as shown in Scheme 1 below:

Scheme 1:

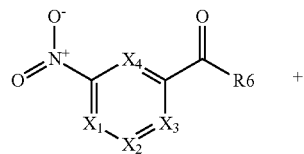

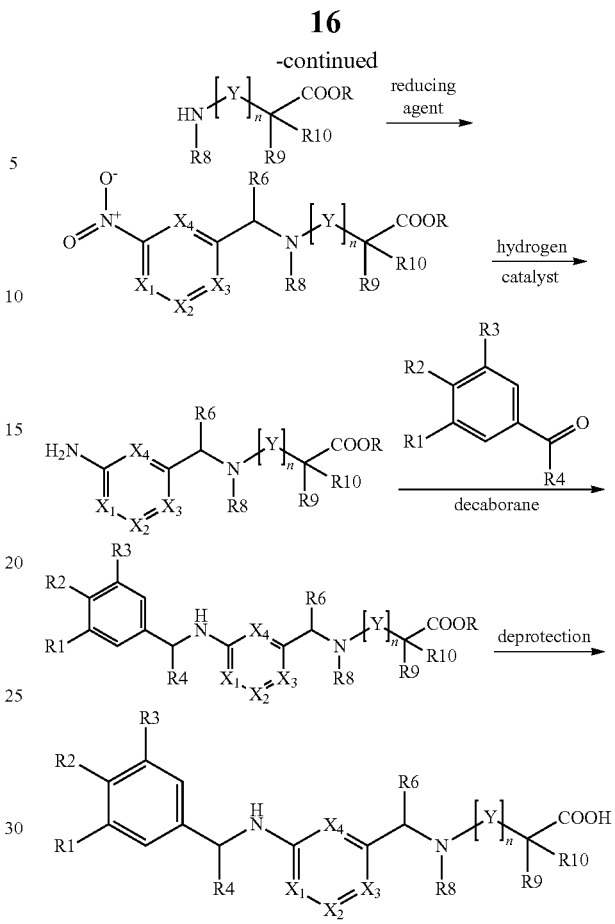

Alternatively, compounds of the invention may be prepared by a reaction sequence involving reductive amination of an appropriate ketone with an appropriate aniline followed by halogen metal exchange with an appropriate organolithium reagent and subsequent quenching with DMF, and either reductive amination with an appropriate amino ester or amino acid followed by an optional deprotection step or alkyl addition using an appropriate Grignard reagent, oxidation of the alcohol with an appropriate oxidizing agent, and reductive amination with an appropriate amino ester or amino acid followed by an optional deprotection step as shown in Scheme 2 below:

Scheme 2:

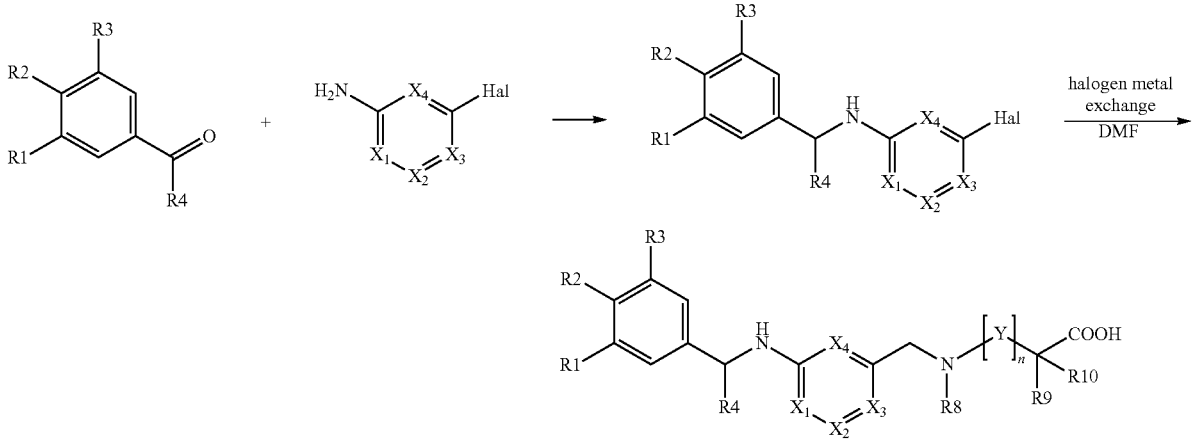

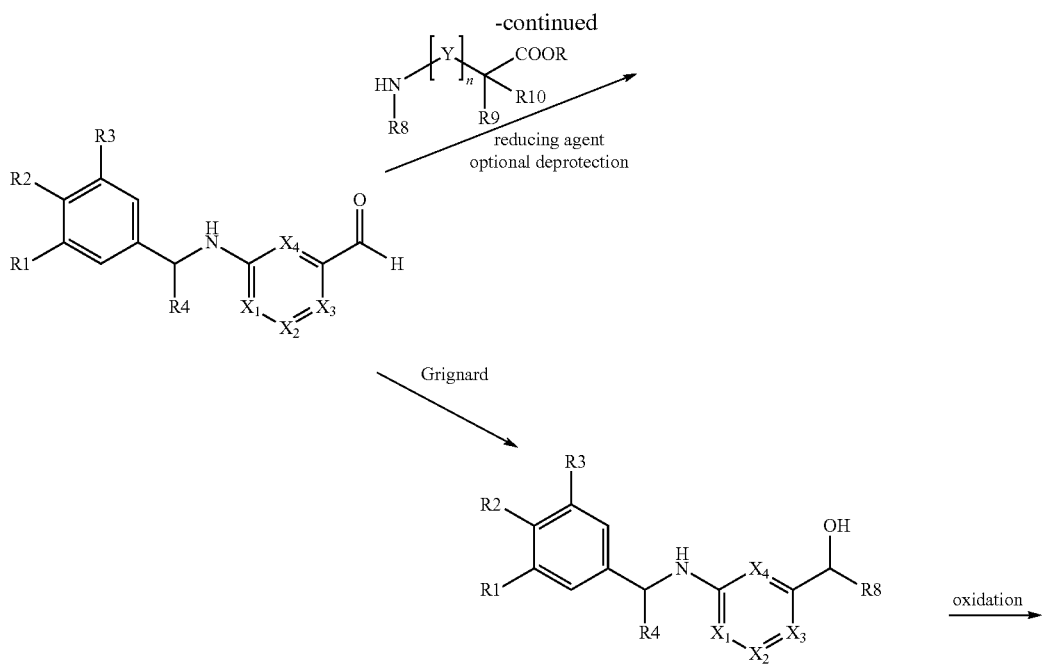

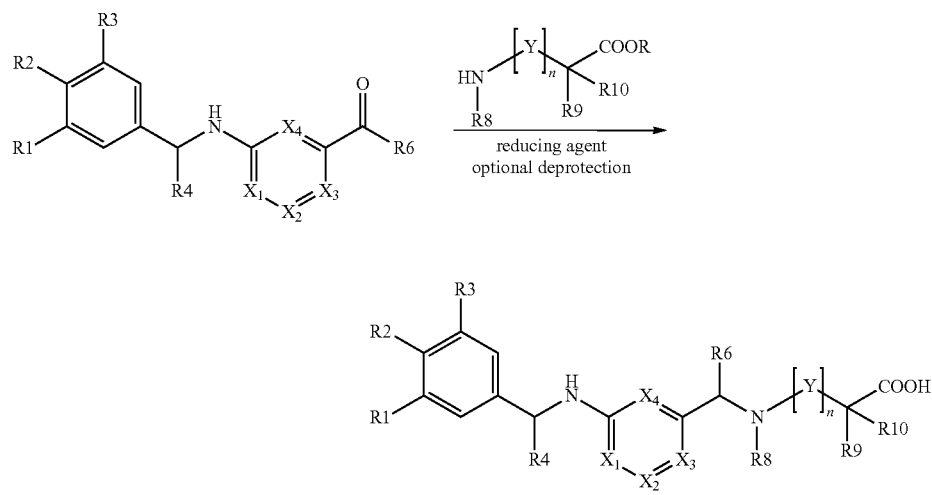

Alternatively, compounds of the invention may be prepared by a reaction sequence involving Buchwald coupling of an appropriate amine with an appropriate protected halobenzaldehyde or halo-pyridyl-carbaldehyde, deprotection, reductive amination with an appropriate amino ester or amino acid followed by an optional deprotection step as shown in Scheme 3 below:

Scheme 3:

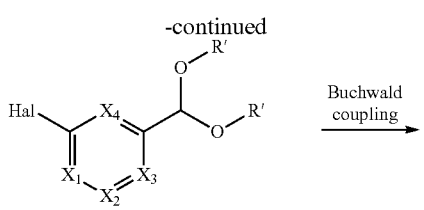

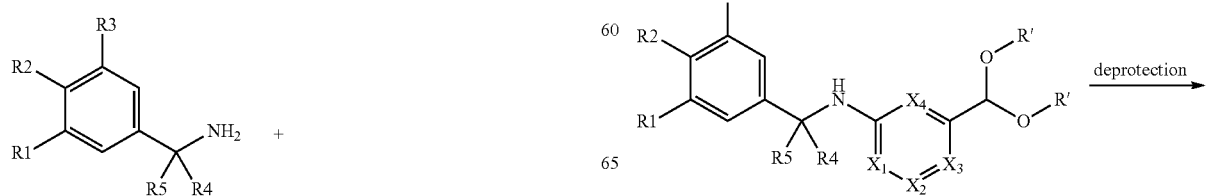

-continued

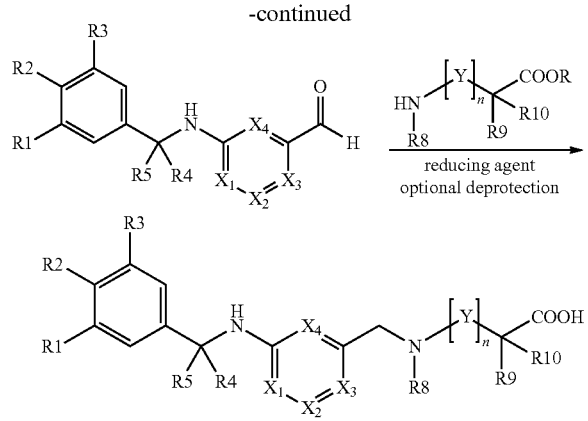

Alternatively, compounds of the invention may be prepared by a reaction sequence involving either reductive amination of an appropriate halo-benzaldehyde or halo-pyridyl-carbaldehyde with an appropriate amino ester or Lewis acid catalyzed Michael addition of an appropriate benzylamine with an appropriate α,β-unsaturated ester followed by Buchwald coupling with an appropriate amine and an optional deprotection step as shown in Scheme 4 below:

Galenic Aspects

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc. Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also Scheme 4:

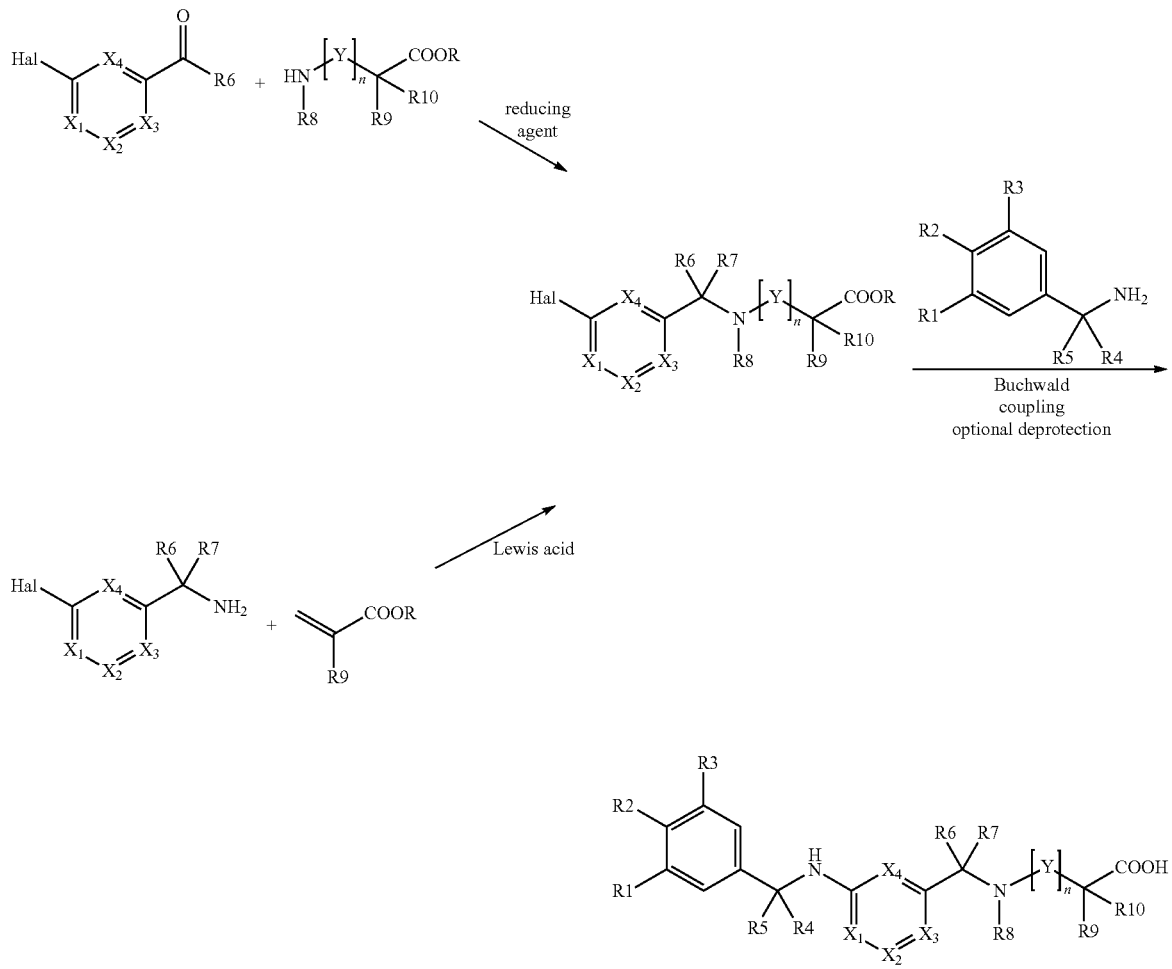

c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be desirable.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

EXPERIMENTAL SECTION

Abbreviations

Boc: tert-Butyloxycarbonyl
BINAP: 2,2'-Bis(diphenylphosphino)-1,1'-binaphthalene
dba: Dibenzylideneacetone
dppf: 1,1'-Bis(diphenylphosphino)ferrocene
DIPEA: Ethyl-diisopropyl-amine, Hünig's base, DIEA
DME: 1,2-Dimethoxy-ethane
DMF: N,N-Dimethylformamide
DMP: Dess-Martin periodinane
DMSO: Dimethylsulfoxide
EtOAc: Acetic acid ethyl ester
EtOH: Ethanol
HOAc: Acetic acid
HPLC: High pressure liquid chromatography
L: Liter
M: Molar
MeOH: Methanol
min: Minutes
mL: Milliliter
NaHMDS: Sodium hexamethyldisilazane
NaOAc: Sodium acetate
PEPPSI-IPr: (1,3-Bis(2,6-diisopropylphenyl)imidazolidene) (3-chloropyridyl) palladium(II) dichloride
Pd—C: Palladium on carbon
PS—$CNBH_3$: Polymer supported cyanoborohydride
rt: Retention time
TBAT: Tetrabutylammonium tri phenyldifluorosilicate
TBME: tert-Butylmethylether
TFA: Trifluoro-acetic acid
THF: Tetrahydrofuran
TMS-$CF_3$: (Trimethylsilyl)trifluoromethane (Ruppert's Reagent)
$TMSCHN_2$: Diazomethyl-trimethyl-silane
Xphos: 2-Dicyclohexylphosphino-2',6'-triisopropyl biphenyl $^1$H-NMR spectra were recorded on a Bruker 400 MHz or a Bruker 500 MHz NMR spectrometer. Significant peaks are tabulated in the order: multiplicity (s, singlet; d, doublet; t, triplet; q, quartet; m, multiplet; br, broad; v, very) and number of protons. Electron Spray ionization (ESI) mass spectra were recorded on an Agilent 1100 Series mass spectrometer. Mass spectrometry results are reported as the ratio of mass over charge.

Detailed analytical HPLC and UPLC chromatography methods referred to in the preparations and Examples below are outlined as follows:

LC/MS Method 1:
Waters Acquity UPLC instrument equipped with diode array detector, Waters SQD Single Stage Quadrupole mass spectrometer or Waters ZQ2000 mass spectrometer and ASCENTIS FusedCore (2.7 μm) 2.1×100 mm column. Peak detection is reported at 210 nm wavelength.
Solvent A: Water containing 3 mM ammonium acetate and 0.05% formic acid.
Solvent B: Acetonitrile containing 0.04% formic acid.
Flow rate at 1.4 mL/minute

| Gradient: | | |
|---|---|---|
| Time [minutes] | Solvent A [%] | Solvent B [%] |
| 0 | 98 | 2 |
| 5 | 2 | 98 |
| 5.5 | 2 | 98 |
| 5.6 | 98 | 2 |
| 6 | 98 | 2 |

LC/MS Method 2:
Waters Acquity UPLC instrument equipped with diode array detector, Waters SQD Single Stage Quadrupole mass spectrometer or Waters ZQ2000 mass spectrometer and Waters Acquity HSS T3 (1.8 μm) 2.1×50 mm column. Peak detection is reported at 210 nm wavelength.
Solvent A: Water containing 3 mM ammonium acetate and 0.05% formic acid.
Solvent B: Acetonitrile containing 0.04% formic acid.
Flow rate at 0.6 mL/minute

| Gradient: | | |
|---|---|---|
| Time [minutes] | Solvent A [%] | Solvent B [%] |
| 0 | 98 | 2 |
| 5 | 2 | 98 |
| 5.5 | 2 | 98 |
| 5.6 | 98 | 2 |
| 6 | 98 | 2 |

LC/MS Method 3:
HP1100 Agilent HPLC instrument equipped with PDA UV detector, Waters ZQ2000 mass spectrometer and Waters XBridge C18 (2.5 μm) 3×30 mm column. Peak detection is reported at 210 nm wavelength.
Solvent A: Water containing 5% (acetonitrile with 0.05% formic acid).
Solvent B: Acetonitrile containing 0.05% formic acid.

| Gradient: | | | |
|---|---|---|---|
| Time [minutes] | Solvent A [%] | Solvent B [%] | Flow rate [mL/min] |
| 0 | 90 | 10 | 0.6 |
| 1.5 | 5 | 95 | 0.7 |
| 2 | 5 | 95 | 0.7 |
| 3.0 | 90 | 10 | 0.6 |

LC/MS Method 4:
HP1100 Agilent HPLC instrument equipped with PDA UV detector, Waters ZQ2000 mass spectrometer and ASCENTIS FusedCore (2.7 μm) 2.1×100 mm column. Peak detection is reported at 210 nm wavelength.
Solvent A: Water containing 3.75 mM ammonium acetate and 0.05% formic acid.
Solvent B: Acetonitrile containing 0.04% formic acid.
Flow rate at 1.2 mL/minute

| Gradient: | | |
|---|---|---|
| Time [minutes] | Solvent A [%] | Solvent B [%] |
| 0 | 98 | 2 |
| 1.40 | 2 | 98 |
| 2.15 | 2 | 98 |
| 2.19 | 98 | 2 |

UPLC Method:

Waters Acquity UPLC instrument equipped with diode array detector and Waters Acquity UPLC® BEH C18 (1.7 μm) 2.1×50 mm column. Peak detection is reported at 210 nm wavelength.

Solvent A: water (1800 mL), acetonitrile (200 mL), tetramethylammonium hydroxide (40 mL, 10% in water), phosphoric acid (4 mL)

Solvent B: water (500 mL), acetonitrile (1500 mL), tetramethylammonium hydroxide (40 mL, 10% in water), phosphoric acid (4 mL)

Flow rate at 0.75 mL/minute

| Gradient: | | |
|---|---|---|
| Time [minutes] | Solvent A [%] | Solvent B [%] |
| 0 | 95 | 5 |
| 2 | 5 | 95 |
| 2.7 | 5 | 95 |
| 3 | 5 | 95 |

Preparative Chiral Separation:

Method A: Separation was performed using a Chiralcel OJ 10×50 cm (20 μm) and n-heptane/EtOH as mobile phase with a flow of 100 ml/min and UV detection (220 nm).

Analytical Chiral HPLC:

Method B: Analysis was performed using a Chiralcel OJ 250×4.6 mm (5 μm) and n-heptane/EtOH/MeOH as mobile phase with a flow of 0.9 ml/min and UV detection (220 nm).

All reagents, starting materials and intermediates utilized in these examples are available from commercial sources or are readily prepared by methods known to those skilled in the art.

Synthesis of Aryl Benzylamine Compounds

Compounds of the invention may be prepared by a reaction sequence involving for example a reductive amination of an appropriate nitro-benzaldehyde with an appropriate amine, reduction of the aromatic nitro group, and reductive amination of the aniline with an appropriate ketone followed by a deprotection step as shown in Scheme 1 below:

Scheme 1:

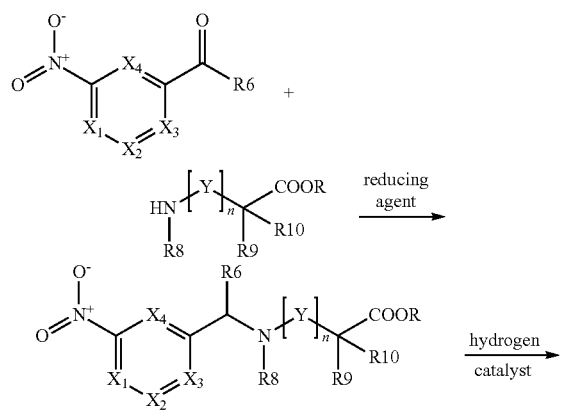

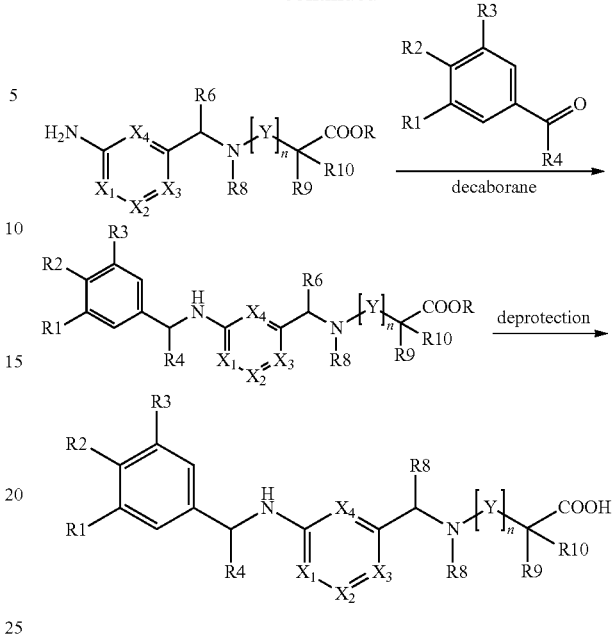

The following compounds were made in accordance to the above indicated reaction Scheme 1:

EXAMPLE 1

1-{3-[1-(4-Chloro-3-methyl-phenyl)-ethylamino]-benzyl}-azetidine-3-carboxylic acid

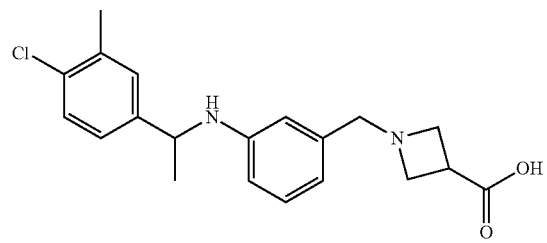 [SMILES: Cc1cc(C(C)Nc2cccc(CN3CC(C(=O)O)C3)c2)ccc1Cl]

1. Azetidine-3-carboxylic acid methyl ester hydrochloride, INT 1

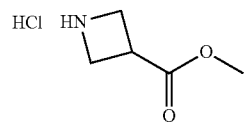

To a solution of 1-(tert-butoxycarbonyl)azetidine-3-carboxylic acid (8.00 g, 39.8 mmol) in MeOH (60 mL) was added 4 M HCl in dioxane (60 mL, 240.0 mmol). The mixture was refluxed for 2 hours. The mixture was concentrated to afford INT 1.

MS (ESI): 116 [M+H]$^+$, $^1$H-NMR (DMSO-d$_6$): δ (ppm) 9.61 (br s, 1H), 9.28 (br s, 1H), 4.13-3.95 (m, 4H), 3.76-3.60 (m, 1H), 3.68 (s, 3H).

2. 1-(3-Nitro-benzyl)-azetidine-3-carboxylic acid methyl ester, INT 2

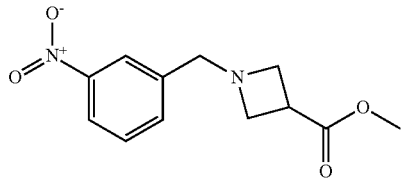 [SMILES: COC(=O)C1CN(Cc2cccc([N+](=O)[O-])c2)C1]

To a solution of amine INT 1 (6.00 g, 39.6 mmol) in CH$_2$Cl$_2$ (396 mL) and MeOH (50 mL) was added DIPEA (6.9 mL, 39.6 mmol). HOAc was added to adjust the pH of the solution to 4-5. 3-Nitrobenzaldehyde (6.58 g, 43.5 mmol) was added and the mixture was stirred at 40° C. for 1 hour. After cooling to room temperature, NaBH(OAc)$_3$ (16.78 g, 79.2 mmol) was added and the mixture was stirred at room temperature overnight. The mixture was quenched with saturated aqueous NaHCO$_3$. The aqueous layer was extracted with CH$_2$Cl$_2$ (2×). The combined organic layers were washed with brine, dried over MgSO$_4$, filtered and concentrated. The residue was purified by flash chromatography on silica gel (CH$_2$Cl$_2$/MeOH) to afford INT 2.

MS (ESI): 251 [M+H]$^+$, $^1$H-NMR (CDCl$_3$): δ (ppm) 8.18 (5, 1H), 8.13 (d, 1H), 7.65 (d, 1H), 7.50 (dd, 1H), 3.77-3.70 (m, 2H), 3.74 (s, 3H), 3.65-3.55 (m, 2H), 3.45-3.33 (m, 3H).

3. 1-(3-Amino-benzyl)-azetidine-3-carboxylic acid methyl ester, INT 3

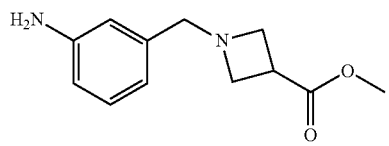 [SMILES: COC(=O)C1CN(Cc2cccc(N)c2)C1]

To a solution of INT 2 (250 mg, 0.99 mmol) in EtOH (10 mL) was added Pd—C 10% (25 mg). The mixture was stirred under 1 atm of H$_2$ for 1 hour. The mixture was quenched with CH$_2$Cl$_2$ and filtered through a pad of Celite. The filtrate was concentrated to give INT 3.

MS (ESI): 221 [M+H]$^+$, $^1$H-NMR (DMSO-d$_6$): δ (ppm) 6.92 (dd, 1H), 6.47 (s, 1H), 6.41 (d, 1H), 6.37 (d, 1H), 4.96 (s, 2H), 3.63 (s, 3H), 3.40-3.25 (m, 5H), 3.18-3.13 (m, 2H).

4. 1-{3-[1-(4-Chloro-3-methyl-phenyl)-ethylamino]-benzyl}-azetidine-3-carboxylic acid methyl ester, INT 4

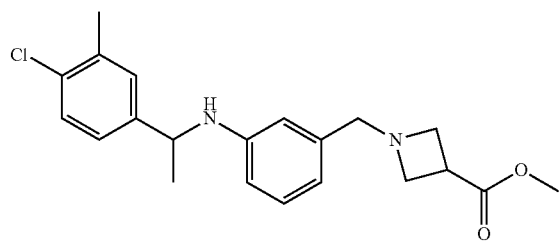 [SMILES: COC(=O)C1CN(Cc2cccc(NC(C)c3ccc(Cl)c(C)c3)c2)C1]

To a solution of INT 3 (220 mg, 0.99 mmol) and 1-(4-chloro-3-methyl-phenyl)-ethanone (202 mg, 1.20 mmol) in MeOH (10 mL) was added decaborane (85 mg, 0.70 mmol). The mixture was stirred at 60° C. overnight. More decaborane (85 mg, 0.70 mmol) was added and the mixture was stirred at 60° C. for an additional 3 hours. The mixture was concentrated. The residue was purified by chromatography on silica gel (CH$_2$Cl$_2$/MeOH) to afford INT 4.

MS (ESI): 373 [M+H]$^+$, $^1$H-NMR (CDCl$_3$): δ (ppm) 7.18 (d, 1H), 7.15 (d, 1H), 7.05 (dd, 1H), 6.98 (dd, 1H), 6.50 (d, 1H), 6.44 (s, 1H), 6.35 (dd, 1H), 4.36 (q, 1H), 4.07 (br s, 1H), 3.82-3.70 (m, 2H), 3.68 (s, 2H), 3.67 (s, 3H), 3.55-3.45 (m, 2H), 3.42-3.34 (m, 1H), 2.27 (s, 3H), 1.40 (d, 3H).

5. 1-{3-[1-(4-Chloro-3-methyl-phenyl)-ethylamino]-benzyl}-azetidine-3-carboxylic acid To a solution of INT 4 (85 mg, 0.23 mmol) in THF (2.2 mL) was added 1 M LiOH (1.1 mL, 1.14 mmol). The resulting mixture was stirred at room temperature for 19 hours. The mixture was acidified to pH 5 with 1 M HCl. The organic solvent was removed. More 1 M HCl was added to adjust the pH to 3. The mixture was extracted with EtOAc (3×). The combined organic layers were dried over MgSO$_4$, filtered and concentrated. The residue was purified by chromatography on silica gel (CH$_2$Cl$_2$/MeOH) to give Example 1.

MS (ESI): 359 [M+H]$^+$, $^1$H-NMR (DMSO-d$_6$): δ (ppm) 7.33 (s, 1H), 7.29 (d, 1H), 7.18 (d, 1H), 6.87 (dd, 1H), 6.43 (s, 1H), 6.33 (d, 1H), 6.28 (d, 1H), 6.08 (d, 1H), 4.39 (m, 1H), 3.38-3.20 (m, 4H), 3.10-3.00 (m, 3H), 2.27 (s, 3H), 1.36 (d, 3H).

EXAMPLE 2

1-{3-[1-(4-Chloro-3-methyl-phenyl)-propylamino]-benzyl}-azetidine-3-carboxylic acid

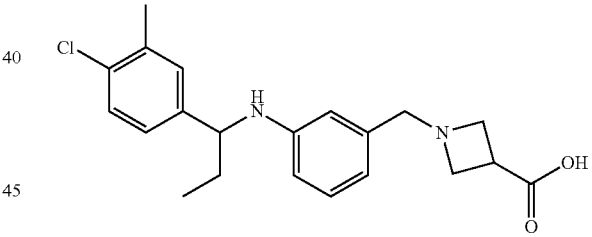

The title compound was prepared according to Scheme 1 following a procedure analogous to Example 1 using ketone INT 5 (synthesis below) in step 4.

LC/MS method 2: MS (ESI): 373 [M+H]$^+$, rt=1.99 min.

1. 1-(4-Chloro-3-methyl-phenyl)-propan-1-one, INT 5

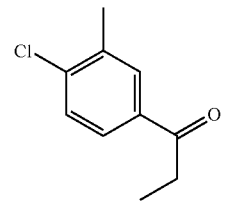

To a solution of 4-chloro-3-methylbenzoic acid (8.31 g, 48.7 mmol) in $CH_2Cl_2$ (50 mL) was added DMF (175 μm) and thionyl chloride (35.5 mL, 487 mmol) and the resulting mixture was refluxed for 1 hour. After cooling down, the mixture was evaporated to dryness and taken up in THF (50 mL). The resulting solution was cooled to 0° C. and triethylamine (13.5 mL, 97 mmol) was added followed by N,O-dimethylhydroxyl-amine hydrochloride (5.7 g, 58.4 mmol) and the resulting mixture was stirred at room temperature overnight. The mixture was diluted with $CH_2Cl_2$ and washed with 1 M $KHSO_4$, saturated aqueous $NaHCO_3$ and brine. The organic layer was dried over sodium sulfate, filtered and concentrated. The resulting crude Weinreb amide (10.4 g, 48.7 mmol) was taken up in THF (440 mL) and cooled to 0° C. under an argon atmosphere. Ethylmagnesium bromide (1 M in TBME, 97 ml, 97 mmol) was then slowly added and the resulting mixture was stirred for 2 hours at 0° C. The mixture was quenched with a saturated aqueous ammonium chloride solution. The THF was evaporated and the product was extracted with EtOAc. The organic layer was washed with brine, dried over sodium sulfate, filtered and concentrated. The residue was purified by chromatography on silica gel (cyclohexane/EtOAc) to give INT 5.

$^1$H-NMR ($CDCl_3$): δ (ppm) 7.93 (d, 1H), 7.76 (dd, 1H), 7.55 (d, 1H), 3.01 (q, 2H), 2.39 (s, 3H) 1.06 (t, 3H).

Alternatively, compounds of the invention may be prepared by a reaction sequence involving reductive amination of an appropriate ketone with an appropriate aniline followed by halogen metal exchange with an appropriate organolithium reagent and subsequent quenching with DMF, and either reductive amination with an appropriate amino ester or amino acid followed by an optional deprotection step or alkyl addition using an appropriate Grignard reagent, oxidation of the alcohol with an appropriate oxidizing agent, and reductive amination with an appropriate amino ester or amino acid followed by an optional deprotection step as shown in Scheme 2 below:

Scheme 2:

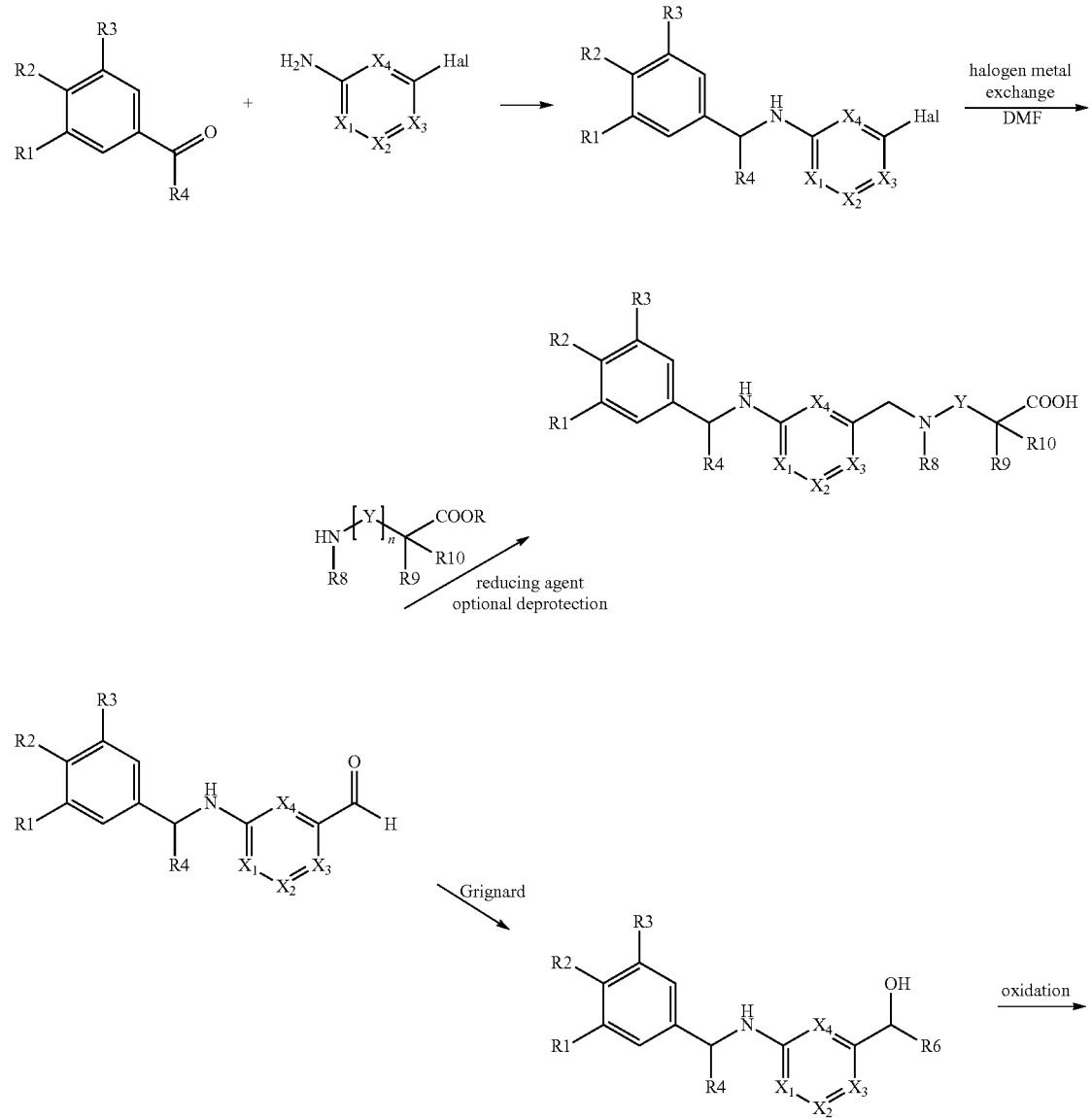

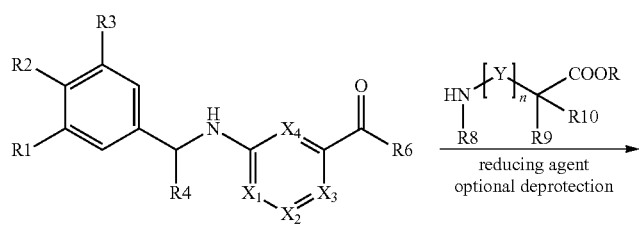 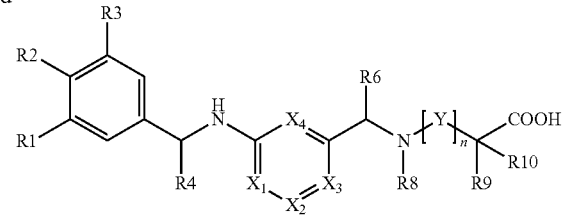

reducing agent
optional deprotection

The following compounds were made in accordance to the above indicated reaction Scheme 2:

EXAMPLE 3

1-{3-[(R)-1-(4-Chloro-3-methyl-phenyl)-propylamino]-benzyl}-azetidine-3-carboxylic acid

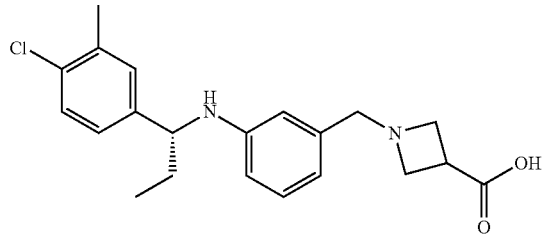 [SMILES: CCC(Nc1cccc(CN2CC(C(=O)O)C2)c1)c1ccc(Cl)c(C)c1]

1. (3-Bromo-phenyl)-[(R)-1-(4-chloro-3-methyl-phenyl)-propyl]-amine, INT 6

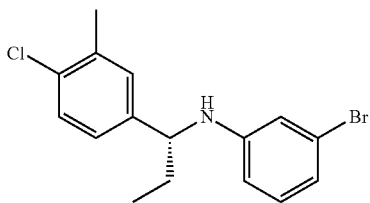 [SMILES: CC[C@@H](Nc1cccc(Br)c1)c1ccc(Cl)c(C)c1]

To a solution of INT 5 (360 g, 1.941 mol) and 3-bromoaniline (509 g, 2.957 mol) in toluene (3.5 L) was added p-toluenesulfonic acid monohydrate (18.8 g, 0.099 mol). The mixture, equipped with a Dean stark trap, was refluxed overnight. After 1.5 hours, 300 mL of turbid toluene was removed from the Dean stark trap. After 5 hours 150 mL of turbid toluene was removed from the Dean stark trap and dry toluene and molecular sieves 4 Å (20 g) were added. On the next day, more molecular sieves 4 Å (60 g) were added and the reaction mixture was refluxed for an additional 4 hours. The molecular sieves were filtered off and the filtrate was concentrated. The crude imine and (S)—N-(5-fluoro-2-hydroxybenzyl)-2-methylpropane-2-sulfinamide (68.5 g, 0.279 mol, prepared according to: Pei, Dong; Wang, Zhouyu; Wei, Siyu; Zhang, Yu; Sun, Jian. *Org. Lett.* (2006), 8 (25), 5913-5915.) were dissolved in CH$_2$Cl$_2$ (6.6 L) and the mixture was cooled to −26° C. Trichlorosilane (302 g, 2.233 mol) was added dropwise within 20 minutes and the resulting mixture was stirred overnight keeping the temperature between −25° C. and −22°

C. The mixture was poured onto saturated aqueous NaHCO$_3$ (7 L) and extracted with EtOAc. The combined organic layers were washed with brine and dried over sodium sulfate, filtered and concentrated. The residue was purified by chromatography on silica gel (cyclohexane/EtOAc). The resulting product was further purified by formation of the HCl salt and washing it with Et$_2$O. The resulting solid was dissolved in hot EtOH and cooled to room temperature while stirring. The resulting solid was filtered off and dried in vacuum. The salt was then liberated to give INT 6.

MS (ESI): 338 [M+H]$^+$, $^1$H-NMR (DMSO-d$_6$): δ (ppm) 7.35-7.31 (m, 2H), 7.18 (dd, 1H), 6.91 (dd, 1H), 6.70-6.68 (m, 1H), 6.58 (dd, 1H), 6.49-6.44 (m, 2H), 4.20 (q, 1H), 2.29 (s, 3H), 1.80-1.69 (m, 1H), 1.69-1.60 (m, 1H), 0.89 (t, 3H).

2. 3-[(R)-1-(4-Chloro-3-methyl-phenyl)-propylamino]-benzaldehyde, INT 7

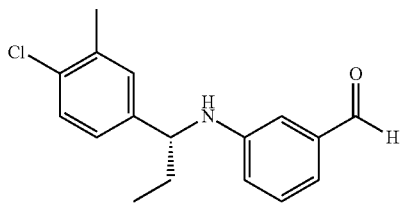 [SMILES: CC[C@@H](Nc1cccc(C=O)c1)c1ccc(Cl)c(C)c1]

To a solution of INT 6 (5.00 g, 14.8 mmol) in Et$_2$O (148 mL) at −78° C. was added tBuLi (1.7 M in pentane, 34.7 mL, 59.0 mmol) dropwise. The mixture was stirred at −78° C. for 40 minutes and DMF (2.5 mL) was added. The reaction mixture was stirred at −78° C. for an additional 30 minutes. The mixture was quenched with saturated aqueous NH$_4$Cl and extracted with Et$_2$O (2×). The combined organic layers were washed with brine, dried over MgSO$_4$, filtered and concentrated. The residue was purified by chromatography on silica gel (heptane/EtOAc) to afford INT 7.

MS (ESI): 288 [M+H]$^+$, $^1$H-NMR (CDCl$_3$): δ (ppm) 9.87 (s, 1H), 7.29 (d, 1H), 7.25 (d, 1H), 7.21 (5, 1H), 7.18 (d, 1H), 7.12 (d, 1H), 7.04 (s, 1H), 6.78 (d, 1H), 4.55 (br s, 1H), 4.24 (t, 1H), 2.37 (s, 3H), 1.92-1.75 (m, 2H), 0.98 (t, 3H).

3. 1-{3-[(R)-1-(4-Chloro-3-methyl-phenyl)-propylamino]-benzyl}-azetidine-3-carboxylic acid To a solution of INT 7 (700 mg, 2.43 mmol) and azetidine-3-carboxylic acid (248 mg, 2.92 mmol) in MeOH (24 mL) was added HOAc (0.14 mL, 2.43 mmol) followed by PS—CNBH$_3$ (2.5 mmol/g, 1.95 g, 4.86 mmol). The reaction mixture was stirred at room temperature for 3 days. The mixture was filtered over Celite. The filtrate was concentrated. The residue was purified by preparative HPLC (H$_2$O/CH$_3$CN) to give the title compound Example 3.

MS (ESI): 373 [M+H]+, 1H-NMR (DMSO-d6): δ (ppm) 7.33 (s, 1H), 7.30 (d, 1H), 7.19 (d, 1H), 6.88 (dd, 1H), 6.47 (S, 1H), 6.33 (d, 2H), 6.03 (d, 1H), 4.17 (m, 1H), 3.34 (5, 2H), 3.30-3.25 (m, 2H), 3.18-3.06 (m, 3H), 2.29 (s, 3H), 1.82-1.70 (m, 1H), 1.70-1.58 (m, 1H), 0.89 (t, 3H).

EXAMPLE 4

1-{5-[1-(4-Chloro-3-methyl-phenyl)-propylamino]-2-methyl-benzyl}-azetidine-3-carboxylic acid

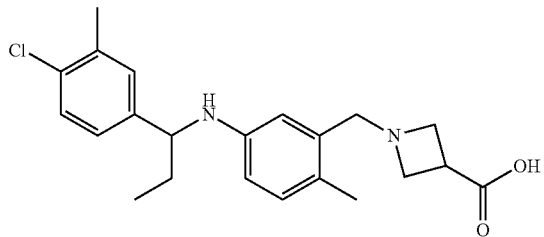 [SMILES: CCC(Nc1ccc(C)c(CN2CC(C(=O)O)C2)c1)c1ccc(Cl)c(C)c1]

1. (3-Bromo-4-methyl-phenyl)-[1-(4-chloro-3-methyl-phenyl)-propyl]-amine, INT 8

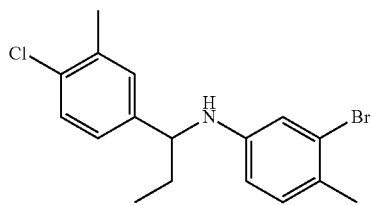 [SMILES: CCC(Nc1ccc(C)c(Br)c1)c1ccc(Cl)c(C)c1]

To a solution of INT 5 (3.00 g, 16.4 mmol) and 3-bromo-4-methylaniline (3.06 g, 16.4 mmol) in MeOH (164 mL) was added decaborane (1.00 g, 8.2 mmol). The reaction mixture was stirred at room temperature overnight. More decaborane (0.50 g, 4.1 mmol) was added. The mixture was stirred at 60° C. for 2 hours. The mixture was concentrated. The residue was purified by chromatography on silica gel (heptane/EtOAc) to afford INT 8.

MS (ESI): 352 [M+H]+, 1H-NMR (CDCl3): δ (ppm) 7.29 (d, 1H), 7.19 (s, 1H), 7.10 (d, 1H), 6.93 (d, 1H), 6.78 (s, 1H), 6.39 (d, 1H), 4.12 (t, 1H), 2.37 (s, 3H), 2.25 (s, 3H), 1.90-1.75 (m, 2H), 0.94 (t, 3H).

2. 5-[1-(4-Chloro-3-methyl-phenyl)-propylamino]-2-methyl-benzaldehyde, INT 9

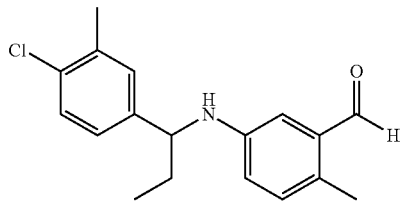

To a solution of INT 8 (2.20 g, 14.7 mmol) in Et2O (147 mL) at −78° C. was added tBuLi (1.7 M in pentane, 34.7 mL, 59.0 mmol) dropwise. The mixture was stirred at −78° C. for 40 min, then DMF (2.5 mL) was added. The reaction mixture was stirred at −78° C. for an additional 20 minutes. The mixture was quenched with saturated aqueous NH4Cl and extracted with Et2O (2×). The combined organic layers were washed with brine, dried over MgSO4, filtered and concentrated. The residue was purified by chromatography on silica gel (heptane/EtOAc) to afford INT 9.

MS (ESI): 302 [M+H]+, 1H-NMR (CDCl3): δ (ppm) 10.17 (s, 1H), 7.28 (d, 1H), 7.21 (s, 1H), 7.11 (d, 1H), 7.02 (s, 1H), 6.99 (d, 1H), 6.68 (d, 1H), 4.21 (t, 1H), 2.51 (s, 3H), 2.36 (s, 3H), 1.93-1.78 (m, 2H), 0.96 (t, 3H).

3. 1-{5-[1-(4-Chloro-3-methyl-phenyl)-propylamino]-2-methyl-benzyl}-azetidine-3-carboxylic acid To a solution of INT 9 (200 mg, 0.66 mmol) and azetidine-3-carboxylic acid (67 mg, 0.66 mmol) in MeOH (6.5 mL) was added HOAc (0.038 mL, 0.66 mmol) followed by NaCNBH3 (42 mg, 0.66 mmol). The reaction mixture was stirred at room temperature for 1 hour. The mixture was diluted with saturated aqueous NaHCO3 and extracted with CH2Cl2 (2×). The combined organic layers were washed with brine, dried over MgSO4, filtered and concentrated. The residue was purified by preparative HPLC (H2O/CH3CN) to afford the title compound Example 4.

LC/MS method 2: MS (ESI): 387 [M+H]+, rt=2.06 min. 1H-NMR (DMSO-d6): δ (ppm) 7.30 (s, 1H), 7.27 (d, 1H), 6.69 (d, 1H), 6.45 (s, 1H), 6.23 (d, 1H), 5.84 (d, 1H), 4.18-4.11 (m, 1H), 3.33 (s, 2H), 3.32-3.23 (m, 2H), 3.18-3.08 (m, 2H), 2.28 (s, 3H), 2.01 (s, 3H), 1.81-1.71 (m, 1H), 1.69-1.59 (m, 1H), 0.88 (t, 3H).

EXAMPLE 5

1-{3-[1-(4-Chloro-3-methyl-phenyl)-propylamino]-4-methyl-benzyl}-azetidine-3-carboxylic acid

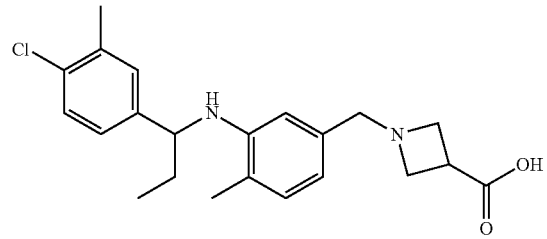 [SMILES: CCC(Nc1cc(CN2CC(C(=O)O)C2)ccc1C)c1ccc(Cl)c(C)c1]

The title compound was prepared according to Scheme 2 following a procedure analogous to Example 4 using 5-bromo-2-methylaniline in step 1.

LC/MS method 2: MS (ESI): 387 [M+H]+, rt=2.06 min.

EXAMPLE 6

1-(1-{3-[(R)-1-(4-Chloro-3-methyl-phenyl)-propylamino]-phenyl}-ethyl)-azetidine-3-carboxylic acid

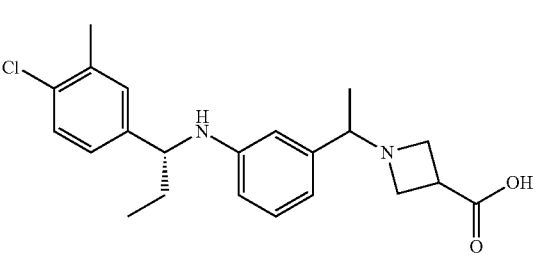 [SMILES: CC[C@@H](Nc1cccc(C(C)N2CC(C(=O)O)C2)c1)c1ccc(Cl)c(C)c1]

1. 1-{3-[(R)-1-(4-Chloro-3-methyl-phenyl)-propylamino]-phenyl}-ethanol, INT 10

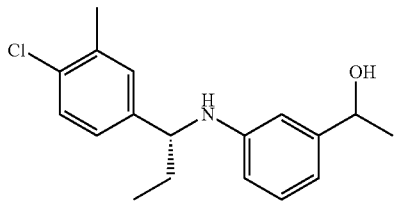 [SMILES: CC[C@@H](Nc1cccc(C(C)O)c1)c1ccc(Cl)c(C)c1]

To a solution of INT 7 (600 mg, 2.09 mmol) in THF (7 mL) at −20° C. was added methylmagnesium bromide (3 M in Et₂O, 0.83 mL, 2.50 mmol) dropwise. The reaction mixture was stirred at −20° C. for 1 hour. The mixture was quenched with saturated aqueous NH₄Cl and extracted with Et₂O (3×). The combined organic layers were washed with brine (2×), dried over MgSO₄, filtered and concentrated. The residue was purified by chromatography on silica gel (heptane/EtOAc) to give INT 10.

MS (ESI): 304 [M+H]⁺, ¹H-NMR (CDCl₃): δ (ppm) 7.29 (d, 1H), 7.22 (d, 1H), 7.12 (dd, 1H), 7.08 (dd, 1H), 6.66 (d, 1H), 6.62-6.58 (m, 1H), 6.41-6.38 (m, 1H), 4.80-4.73 (m, 1H), 4.20 (t, 1H), 4.14 (br s, 1H), 2.37 (s, 3H), 1.88-1.75 (m, 2H), 1.80 (br s, 1H), 1.44 (t, 3H), 0.97 (t, 3H).

2. 1-{3-[(R)-1-(4-Chloro-3-methyl-phenyl)-propylamino]-phenyl}-ethanone, INT 11

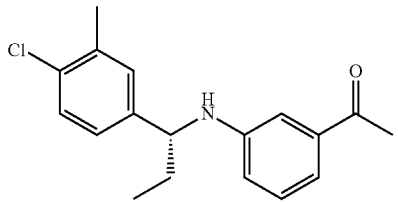 [SMILES: CC[C@@H](Nc1cccc(C(C)=O)c1)c1ccc(Cl)c(C)c1]

To a solution of INT 10 (446 mg, 1.47 mmol) in CH₂Cl₂ was added DMP (747 mg, 1.76 mmol). The reaction mixture was stirred at room temperature for 1 hour. The mixture was quenched with saturated aqueous NaHCO₃/saturated aqueous Na₂S₂O₃ 5/1 and diluted with CH₂Cl₂. The mixture was stirred vigorously until the organic layer was clear. The organic layer was washed with saturated aqueous NaHCO₃ and brine, dried over MgSO₄, filtered and concentrated. The residue was purified by chromatography on silica gel (heptane/CH₂Cl₂) to afford INT 11.

MS (ESI): 302 [M+H]⁺, ¹H-NMR (CDCl₃): δ (ppm) 7.19 (d, 1H), 7.15-7.11 (m, 2H), 7.07 (dd, 1H), 7.06-7.04 (m, 1H), 7.02 (dd, 1H), 6.59-6.55 (m, 1H), 4.16-4.11 (m, 2H), 2.42 (s, 3H), 2.27 (s, 3H), 1.80-1.67 (m, 2H), 0.88 (t, 3H).

3. 1-(1-{3-[(R)-1-(4-Chloro-3-methyl-phenyl)-propylamino]-phenyl}-ethyl)-azetidine-3-carboxylic acid To a solution of INT 11 (213 mg, 0.71 mmol) and azetidine-3-carboxylic acid (75 mg, 0.74 mmol) in MeOH (7 mL) was added HOAc (0.040 mL, 0.71 mmol) followed by NaCNBH₃ (44 mg, 0.71 mmol). The reaction mixture was stirred at room temperature for 40 hours. More azetidine-3-carboxylic acid (10 mg, 0.099 mol) and NaCNBH₃ (10 mg, 0.16 mmol) were added and the mixture was stirred at room temperature for an additional 4 hours. The mixture was concentrated. The residue was taken up in CH₂Cl₂ and washed with brine. The aqueous layer was extracted with CH₂Cl₂ and EtOAc. The combined organic layers were dried over MgSO₄, filtered and concentrated. The residue was purified by preparative HPLC (H₂O/CH₃CN) to afford the title compound Example 6.

LC/MS method 2: MS (ESI): 387 [M+H]⁺, rt=5.92 and 5.98 min (diastereomers). ¹H-NMR (DMSO-d₆): δ (ppm) 11.97 (br s, 1H), 7.31 (s, 1H), 7.29 (d, 1H), 7.17 (d, 1H), 6.85 (dd, 1H), 6.50 (d, 1H), 6.39-6.27 (m, 2H), 6.04 (t, 1H), 4.20-4.10 (m, 1H), 3.38-3.29 (m, 1H), 3.13-2.92 (m, 5H), 2.27 (s, 3H), 1.83-1.72 (m, 1H), 1.70-1.60 (m, 1H), 0.98 (d, 3H), 0.86 (t, 3H).

EXAMPLE 7

1-{3-[1-(4-Chloro-3-methyl-phenyl)-propylamino]-2-methyl-benzyl}-azetidine-3-carboxylic acid

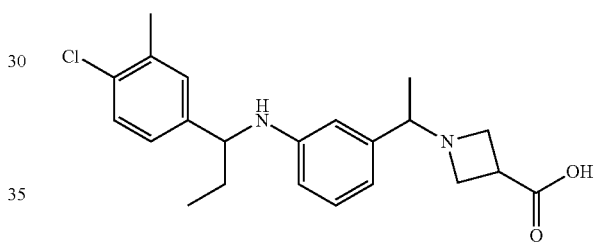

The title compound was prepared according to Scheme 2 following a procedure analogous to Example 4 using 3-bromo-2-methylaniline in step 1.

LC/MS method 2: MS (ESI): 387 [M+H]⁺, rt=2.15 min.

EXAMPLE 8

1-{3-[(R)-1-(4-Chloro-3-methyl-phenyl)-propylamino]-benzyl}-3-methyl-azetidine-3-carboxylic acid

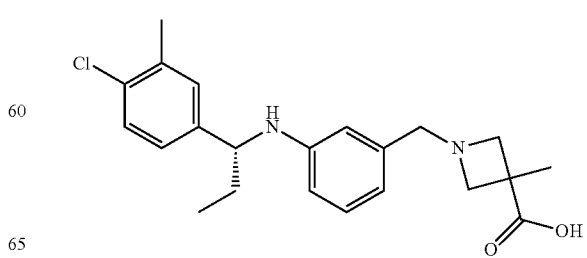

1. Azetidine-1,3-dicarboxylic acid 1-tert-butyl ester 3-methyl ester, INT 12

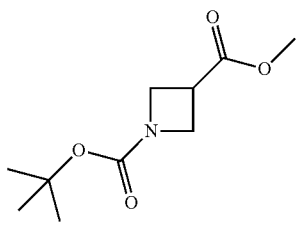

To a solution of Boc-azetidine-3-carboxylic acid (10.00 g, 49.7 mmol) in toluene (170 mL) and MeOH (85 mL) was added TMSCHN$_2$ (2.0 M in Et$_2$O, 32.3 mL, 64.6 mmol) dropwise. The reaction mixture was stirred at room temperature for 50 minutes. The mixture was concentrated to afford INT 12.

MS (ESI): 160 [M+H−tBu]$^+$. $^1$H-NMR (CDCl$_3$): δ (ppm) 4.08 (d, 4H), 3.73 (s, 3H), 3.37-3.29 (m, 1H), 1.42 (s, 9H).

2. 3-Methyl-azetidine-1,3-dicarboxylic acid 1-tert-butyl ester 3-methyl ester, INT 13

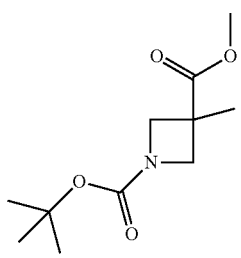

To a solution of INT 12 (2.50 g, 11.6 mmol) in THF (100 mL) at −78° C. was added NaHMDS (1.0 M in THF, 15.1 mL, 15.1 mmol). The mixture was stirred at −78° C. for 30 minutes. MeI (2.14 g, 15.1 mmol) was added and the reaction mixture was stirred at −78° C. for 2 hours. The mixture was quenched with saturated aqueous NH$_4$Cl and extracted with Et$_2$O (2×). The combined organic layers were washed with brine (2×), dried over MgSO$_4$, filtered and concentrated. The residue was purified by chromatography on silica gel (heptane/EtOAc) to give INT 13.

MS (ESI): 174 [M+H−tBu]$^+$. $^1$H-NMR (CDCl$_3$): δ (ppm) 4.13 (d, 2H), 3.66 (s, 3H), 3.58 (d, 2H), 1.45 (s, 3H), 1.36 (s, 9H).

3. 3-Methyl-azetidine-3-carboxylic acid methyl ester hydrochloride, INT 14

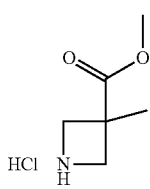

To a solution of INT 13 (1.66 g, 7.24 mmol) in CH$_2$Cl$_2$ was added HCl (2.0 M in Et$_2$O, 36.2 mL, 72.4 mmol). The reaction mixture was stirred at room temperature for 20 hours. The mixture was concentrated to afford INT 14.

MS (ESI): 130 [M+H]$^+$, $^1$H-NMR (DMSO-d$_6$): δ (ppm) 9.95 (br s, 1H), 9.27 (br s, 1H), 4.12 (d, 2H), 3.69-3.59 (m, 5H), 1.47 (s, 3H).

4. 1-{3-[(R)-1-(4-Chloro-3-methyl-phenyl)-propylamino]-benzyl}-3-methyl-azetidine-3-carboxylic acid methyl ester, INT 15

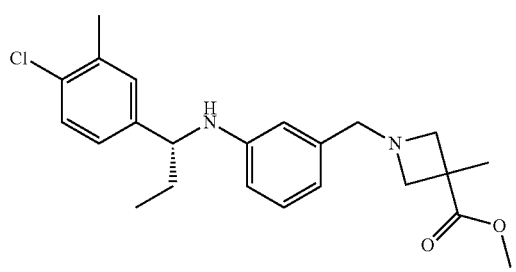 [SMILES: CC[C@@H](Nc1cccc(CN2CC(C)(C(=O)OC)C2)c1)c1ccc(Cl)c(C)c1]

To a mixture of INT 7 (250 mg, 0.87 mmol) and INT 14 (158 mg, 0.88 mmol) in MeOH (8.6 mL) was added DIPEA (0.18 mL, 1.04 mmol). Then HOAc (0.099 mL, 1.74 mmol) was added followed by NaCNBH$_3$ (55 mg, 0.87 mmol). The reaction mixture was stirred at room temperature for 4 hours. A solution of INT 14 (50 mg, 0.091 mmol), DIPEA (0.060 mL, 0.021 mmol) and HOAc (0.040 mL, 0.70 mmol) in MeOH (1.0 mL) was added. The mixture was stirred at room temperature for another hour. The mixture was concentrated. The residue was taken up in CH$_2$Cl$_2$ and washed with saturated aqueous NaHCO$_3$ and brine. The organic layer was dried over MgSO$_4$, filtered and concentrated. The residue was purified by chromatography on silica gel (heptane/EtOAc) to give INT 15.

MS (ESI): 401 [M+H]$^+$, $^1$H-NMR (CDCl$_3$): δ (ppm) 7.18 (d, 1H), 7.11 (s, 1H), 7.01 (d, 1H), 6.92 (dd, 1H), 6.45 (d, 1H), 6.35 (s, 1H), 6.28 (d, 1H), 4.09 (t, 1H), 3.63 (s, 3H), 3.43 (d, 1H), 3.37 (d, 1H), 3.34 (d, 1H), 3.30 (d, 1H), 2.99 (d, 1H), 2.92 (d, 1H), 2.26 (s, 3H), 1.76-1.64 (m, 2H), 1.43 (s, 3H), 0.86 (t, 3H).

5. 1-{3-[(R)-1-(4-Chloro-3-methyl-phenyl)-propylamino]-benzyl}-3-methyl-azetidine-3-carboxylic acid To a solution of INT 15 (158 mg, 0.39 mmol) in THF (3.9 mL) at 0° C. was added LiOH (1.0 M in H$_2$O, 1.97 mL, 1.97 mmol). The reaction mixture was stirred at room temperature for 5 hours. The mixture was acidified with 1 M HCl and concentrated. The residue was taken up in CH$_2$Cl$_2$/EtOAc and washed with brine. The aqueous layer was extracted with CH$_2$Cl$_2$/EtOAc (3×). The combined organic layers were dried over MgSO$_4$ and concentrated. The residue was purified by preparative HPLC (H$_2$O/CH$_3$CN) to afford the title compound Example 8.

MS (ESI): 387 [M+H]$^+$, $^1$H-NMR (CD$_3$OD): δ (ppm) 7.18-7.12 (m, 2H), 7.05 (dd, 1H), 6.96 (t, 1H), 6.52 (dd, 1H), 6.46-6.41 (m, 2H), 4.15-4.10 (m, 2H), 4.07 (d, 1H), 4.00 (s, 2H), 3.62-3.53 (m, 2H), 2.21 (s, 3H), 1.79-1.69 (m, 1H), 1.69-1.60 (m, 1H), 1.33 (s, 3H), 0.86 (t, 3H).

EXAMPLE 9

1-{3-[1-(4-Chloro-3-methyl-phenyl)-propylamino]-5-methyl-benzyl}-azetidine-3-carboxylic acid

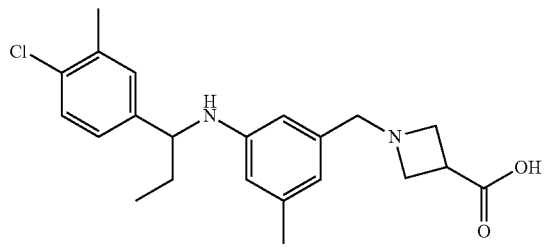 [SMILES: CCC(Nc1cc(C)cc(CN2CC(C(=O)O)C2)c1)c1ccc(Cl)c(C)c1]

The title compound was prepared according to Scheme 2 following a procedure analogous to Example 4 using 3-bromo-5-methylaniline in step 1.
LC/MS method 2: MS (ESI): 387 [M+H]+, rt=2.07 min.

EXAMPLE 10

1-(1-{5-[1-(4-Chloro-3-methyl-phenyl)-propylamino]-2-methyl-phenyl}-ethyl)-azetidine-3-carboxylic acid

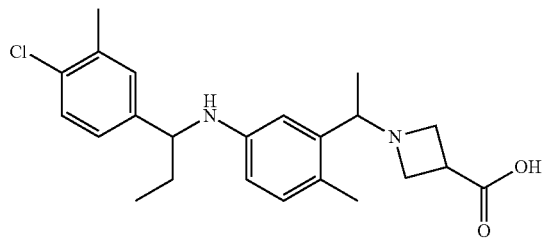 [SMILES: CCC(Nc1ccc(C)c(C(C)N2CC(C(=O)O)C2)c1)c1ccc(Cl)c(C)c1]

The title compound was prepared according to Scheme 2 following a procedure analogous to Example 6 using INT 9 in step 1.
LC/MS method 2: MS (ESI): 401 [M+H]+, rt=6.28 and 6.30 min (diastereomers).

EXAMPLE 11

(R)-1-{3-[(R)-1-(4-Chloro-3-methyl-phenyl-propylamino]-benzyl}-pyrrolidine-3-carboxylic acid

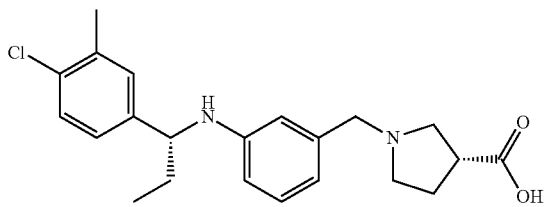 [SMILES: CC[C@@H](Nc1cccc(CN2CC[C@@H](C(=O)O)C2)c1)c1ccc(Cl)c(C)c1]

The title compound was prepared according to Scheme 2 following a procedure analogous to Example 3 using (R)-pyrrolidine-3-carboxylic acid in step 3.
LC/MS method 2: MS (ESI): 387 [M+H]+, rt=2.03 min.

EXAMPLE 12

(S)-1-{3-[(R)-1-(4-Chloro-3-methyl-phenyl)-propylamino]-benzyl}-pyrrolidine-3-carboxylic acid

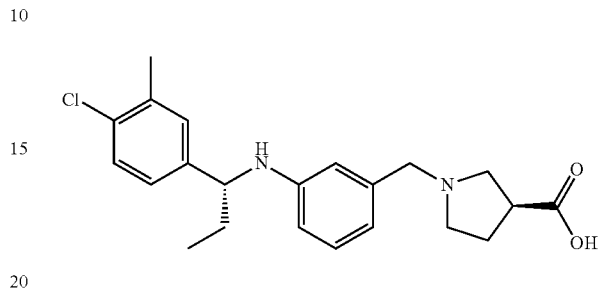

The title compound was prepared according to Scheme 2 following a procedure analogous to Example 3 using (S)-pyrrolidine-3-carboxylic acid in step 3.
LC/MS method 2: MS (ESI): 387 [M+H]+, rt=2.03 min.

EXAMPLE 13

1-(1-{3-[(R)-1-(4-Chloro-3-methyl-phenyl)-propylamino]-phenyl}-propyl)-azetidine-3-carboxylic acid

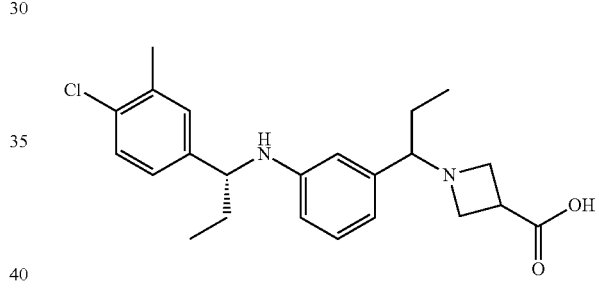

The title compound was prepared according to Scheme 2 following a procedure analogous to Example 6 using ethylmagnesium bromide in step 1.
LC/MS method 2: MS (ESI): 401 [M+H]+, rt=2.17 min.

EXAMPLE 14

(R)-1-{3-[1-(4-Chloro-3-methyl-phenyl)-propylamino]-2-methyl-benzyl}-pyrrolidine-3-carboxylic acid

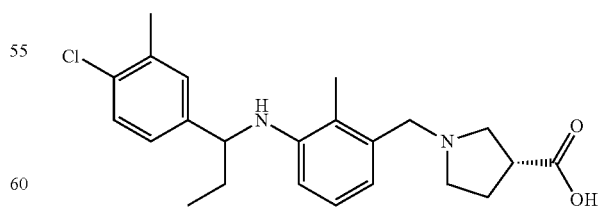

The title compound was prepared according to Scheme 2 following a procedure analogous to Example 4 using 3-bromo-2-methylaniline in step 1 and (R)-pyrrolidine carboxylic acid in step 3.
LC/MS method 2: MS (ESI): 401 [M+H]+, rt=2.17 min.

EXAMPLE 15

(R)-1-{3-[1-(4-Chloro-3-methyl-phenyl)-propylamino]-5-methyl-benzyl}-pyrrolidine-3-carboxylic acid

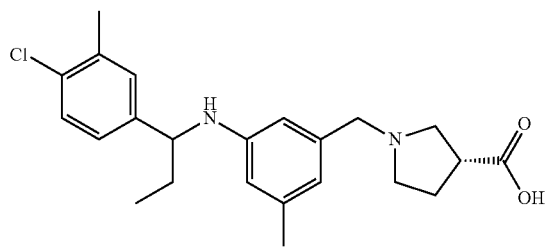 [SMILES: CCC(Nc1cc(C)cc(CN2CC[C@@H](C(=O)O)C2)c1)c1ccc(Cl)c(C)c1]

The title compound was prepared according to Scheme 2 following a procedure analogous to Example 4 using 3-bromo-5-methylaniline in step 1 and (R)-pyrrolidine carboxylic acid in step 3.
LC/MS method 2: MS (ESI): 401 [M+H]$^+$, rt=2.09 min.

EXAMPLE 16

1-{3-[(R)-1-(4-Chloro-3-methyl-phenyl)-propylamino]-benzyl}-3-ethyl-azetidine-3-carboxylic acid

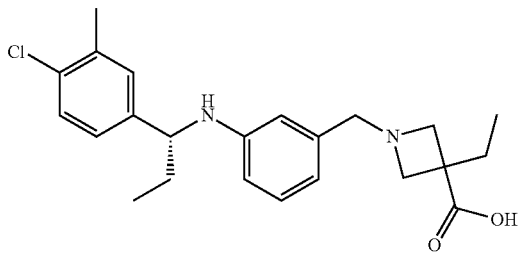 [SMILES: CC[C@@H](Nc1cccc(CN2CC(CC)(C(=O)O)C2)c1)c1ccc(Cl)c(C)c1]

The title compound was prepared according to Scheme 2 following a procedure analogous to Example 8 using iodoethane in step 2.
LC/MS method 2: MS (ESI): 401 [M+H]$^+$, rt=2.08 min.

EXAMPLE 17

1-{3-[1-(4-Chloro-3-methyl-phenyl)-2-methyl-propylamino]-benzyl}-azetidine-3-carboxylic acid

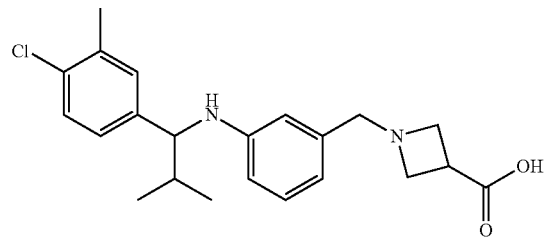 [SMILES: Cc1cc(C(Nc2cccc(CN3CC(C(=O)O)C3)c2)C(C)C)ccc1Cl]

The title compound was prepared according to Scheme 2 following a procedure analogous to Example 4 using ketone INT 16 (synthesis below) in step 1.
LC/MS method 2: MS (ESI): 387 [M+H]$^+$, rt=2.13 min.

1. 1-(4-chloro-3-methyl-phenyl)-2-methyl-propan-1-one, INT 16

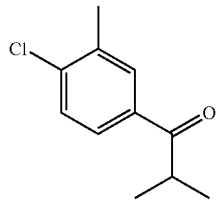

To a solution of 4-chloro-3-methyl-benzonitrile (5 g, 33 mmol) in benzene (100 mL) was slowly added isopropylmagnesium bromide (1 M in THF, 66 mL, 66 mmol) at room temperature. The solution was then heated to reflux for 3 hours. After cooling in an ice bath, the reaction mixture was carefully treated with 6 M HCl (52 mL). It was then heated to reflux for 2 hours with vigorous mechanical stirring. The mixture was allowed to cool to room temperature, diluted with Et$_2$O (100 mL) and washed with water and brine. The organic layer was dried over sodium sulfate, filtered and concentrated. The crude was purified by Kugelrohr distillation (110-130° C./0.1 Torr). Contaminated fractions were further purified by chromatography on silica gel (cyclohexane/EtOAc).
MS (ESI): 197 [M+H]$^+$, $^1$H-NMR (CDCl$_3$): δ (ppm) 7.84 (br s, 1H), 7.73 (d, 1H), 7.44 (d, 1H), 3.52 (m, 1H), 2.45 (s, 3H), 1.23 (d, 6H).

EXAMPLE 18

1-{3-[(R)-1-(4-Chloro-3,5-dimethyl-phenyl)-propylamino]-benzyl}-azetidine-3-carboxylic acid

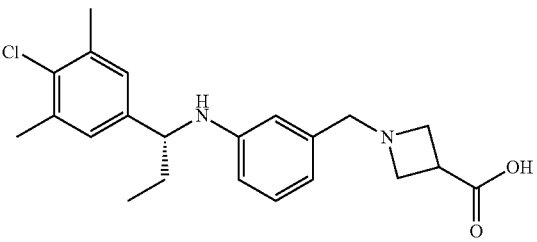 [SMILES: CC[C@@H](Nc1cccc(CN2CC(C(=O)O)C2)c1)c1cc(C)c(Cl)c(C)c1]

The title compound was prepared from bromide INT 19 (synthesis below) following a procedure analogous to steps 2 and 3 of Example 4.
LC/MS method 2: MS (ESI): 387 [M+H]$^+$, rt=2.31 min.

1. 1-(4-Chloro-3,5-dimethyl-phenyl)-propan-1-one, INT 17

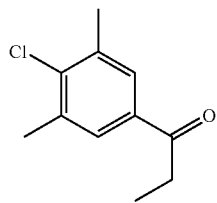

Ethylmagnesium bromide (3 M in Et$_2$O, 3.20 mL, 9.60 mmol) was slowly added to a solution of 4-chloro-3,5-dimethyl-benzonitrile (795 mg, 4.80 mmol) in benzene (20 mL) at room temperature. The mixture was then heated under reflux for 3 hours, cooled in an ice bath and carefully treated with 6 M HCl (7.68 mL, 46.1 mmol). This mixture was heated again under reflux for 2 hours. It was then allowed to cool to room temperature and extracted with EtOAc. The organic layer was washed with brine, dried over sodium sulfate, filtered and concentrated.

MS (ESI): 197 [M+H]$^+$, $^1$H-NMR (CDCl$_3$): δ (ppm) 7.67 (s, 2H), 2.96 (q, 2H), 2.43 (s, 6H), 1.21 (t, 3H).

2. (3-Bromo-phenyl)-[1-(4-chloro-3,5-dimethyl-phenyl)-propyl]-amine, INT 18

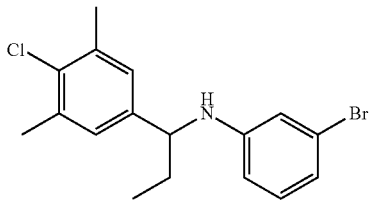 [SMILES: CCC(Nc1cccc(Br)c1)c1cc(C)c(Cl)c(C)c1]

To a solution of ketone INT 17 (910 mg, 4.63 mmol) and 3-bromoaniline (0.504 mL, 4.63 mmol) in MeOH (25 mL) was added decaborane (283 mg, 2.313 mmol) and the resulting mixture was stirred at room temperature overnight. The mixture was concentrated and purified by chromatography on silica gel (cyclohexane/EtOAc).

3. (3-Bromo-phenyl)-[(R)-1-(4-chloro-3,5-dimethyl-phenyl)-propyl]-amine, INT 19

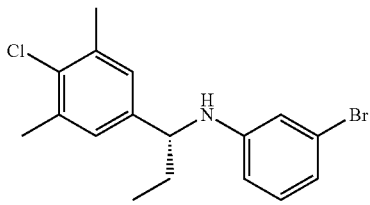 [SMILES: CC[C@@H](Nc1cccc(Br)c1)c1cc(C)c(Cl)c(C)c1]

The title compound was obtained by preparative chiral separation of intermediate INT 18 (Method A). Chiral HPLC method B: rt=6.28 min, n-heptane/EtOH/MeOH (80:10:10).

MS (ESI): 350 [M−H]$^−$, $^1$H-NMR (CDCl$_3$): δ (ppm) 7.0 (s, 2H), 6.91 (t, 1H), 6.74 (d, 1H), 6.66 (s, 1H), 6.38 (d, 1H), 4.07 (br m, 2H), 2.35 (s, 6H), 1.76 (m, 2H), 0.93 (t, 3H).

EXAMPLE 19

1-{3-[(R)-1-(4-Chloro-3,5-dimethyl-phenyl)-propylamino]-benzyl}-azetidine-3-carboxylic acid

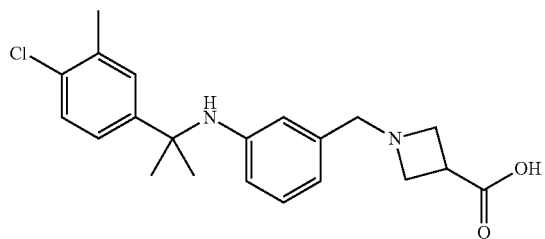 [SMILES: Cc1cc(C(C)(C)Nc2cccc(CN3CC(C(=O)O)C3)c2)ccc1Cl]

The title compound was prepared from iodide INT 23 (synthesis below) following a procedure analogous to steps 2 and 3 of Example 4.

LC/MS method 2: MS (ESI): 373 [M+H]$^+$, rt=1.94 min.

1. 2-(4-Chloro-3-methyl-phenyl)-propan-2-ol, INT 20

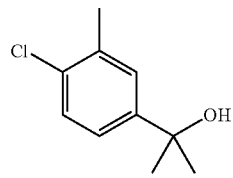

Methyl 4-chloro-3-methylbenzoate (12 g, 65 mmol) was dissolved in THF (250 mL) and cooled in an ice-bath. A solution of methylmagnesium bromide (3 M Et$_2$O, 87 mL, 260 mmol) was added slowly, then the ice bath was removed and the mixture was stirred at room temperature for 2 hours. To complete the reaction, the Et$_2$O was distilled off and the mixture was heated under reflux for 14 hours. The reaction was then cooled and quenched with MeOH and water, acidified with 2 M HCl and extracted twice with Et$_2$O. The organic layers were combined, dried over sodium sulfate, filtered and concentrated. The crude was purified by chromatography on silica gel (cyclohexane/EtOAc).

$^1$H-NMR (CDCl$_3$): δ (ppm) 7.34 (d, 1H), 7.28 (d, 1H), 7.21 (dd, 1H), 2.37 (s, 3H), 1.54 (s, 6H).

2. 4-(1-Azido-1-methyl-ethyl)-1-chloro-2-methyl-benzene, INT 21

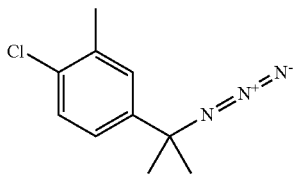

A flask was charged with sodium azide (4.22 g, 65 mmol) and chloroform (250 mL). The mixture was cooled in an ice-salt bath to −5° C. TFA (12.52 mL, 162 mmol) was added over 3 minutes, followed by a solution of the alcohol INT 20 (6 g, 32.5 mmol) in chloroform (10 mL) while the temperature was kept below 0° C. The formed slurry was stirred for one hour, then allowed to warm up to room temperature overnight. After that time, the thick slurry had turned into a cloudy solution. The mixture was treated with concentrated ammonia (25 mL) and water (50 mL). The chloroform layer was separated and the aqueous layer was extracted once more with chloroform. The combined organic extracts were washed with water and brine, dried over sodium sulfate, filtered and concentrated. The crude was purified by chromatography on silica gel (cyclohexane/CH$_2$Cl$_2$).

UPLC: rt=2.34 min. $^1$H-NMR (CDCl$_3$): δ (ppm) 7.31 (d, 1H), 7.29 (s, 1H), 7.19 (dd, 1H), 2.39 (s, 3H), 1.60 (d, 6H).

3. 1-(4-Chloro-3-methyl-phenyl)-1-methyl-ethylamine, INT 22

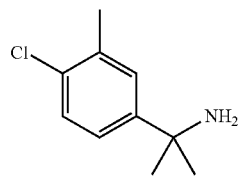

A solution of azide INT 21 (4.58 g, 21.84 mmol) in MeOH (100 mL) was hydrogenated at room temperature under atmospheric pressure for 6 hours in the presence of platinum dioxide hydrate (268 mg, 1.1 mmol). The mixture was filtered through Celite and concentrated. The crude was used without further purification.

UPLC: rt=0.75 min. $^1$H-NMR (CDCl$_3$): δ (ppm) 7.37 (d, 1H), 7.25 (m, 2H), 2.37 (s, 3H), 1.93 (br s, 2H), 1.47 (s, 6H).

4. [1-(4-Chloro-3-methyl-phenyl)-1-methyl-ethyl]-(3-iodo-phenyl)-amine, INT 23

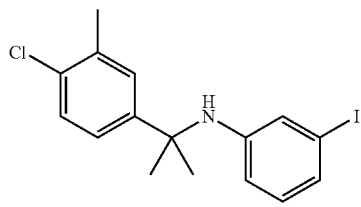 [SMILES: Cc1cc(C(C)(C)Nc2cccc(I)c2)ccc1Cl]

A suspension of amine INT 22 (2.8 g, 15.24 mmol) and potassium tert-butoxide (5.99 g, 53.4 mmol) in DME (25 mL) was purged with argon for 5 minutes. Then, PEPPSI-IPr® (207 mg, 0.305 mmol) and 1,3-diiodobenzene (5.03 g, 15.24 mmol) were added and the flask was closed. The mixture was stirred at room temperature over the weekend. The crude reaction mixture was treated with Et$_2$O (50 mL) and filtered. The residue was washed with more Et$_2$O (30 mL) and the combined filtrates were concentrated. The crude was purified by chromatography on silica gel (cyclohexane/CH$_2$Cl$_2$).

UPLC: rt=2.87 min. $^1$H-NMR (DMSO-d$_6$): δ (ppm) 7.15-7.35 (m, 3H), 6.93 (m, 1H), 6.78 (m, 1H), 6.67 (t, 1H), 6.16 (dd, 1H), 4.02 (br s, 1H), 2.36 (s, 3H), 1.59 (s, 6H).

EXAMPLE 20

1-{3-[(R)-1-(5-Chloro-naphthalen-2-yl)-propylamino]-benzyl}-azetidine-3-carboxylic acid

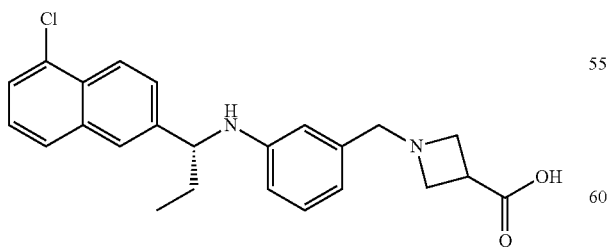

The title compound was prepared according to Scheme 2 following a procedure analogous to Example 3 using INT 28 (synthesis below) in step 1.

LC/MS method 2: MS (ESI): 409 [M+H]$^+$, rt=2.15 min.

1. 4-Allyloxy-benzonitrile, INT 24

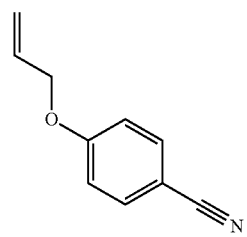

To a solution of 4-hydroxybenzonitrile (20.7 g, 169 mmol) and allyl bromide (27.1 g, 220 mmol) in DMF (620 mL) was added Cs$_2$CO$_3$ (66.7 g, 203 mmol) and water (0.67 mL). The resulting mixture was stirred at room temperature overnight and concentrated. The residue was partitioned between water and EtOAc and the aqueous layer was further extracted with EtOAc. The combined organic layers were washed with brine, dried over sodium sulfate, filtered and concentrated to give INT 24 which was used in the next step without further purification.

LC/MS method 3: MS (ESI): 160 [M+H]$^+$, rt=1.23 min. $^1$H-NMR (CDCl$_3$): δ (ppm) 7.58 (d, 2H), 6.96 (d, 2H), 6.08-5.98 (m, 1H), 5.42 (dd, 1H), 5.33 (dd, 1H), 4.59 (d, 1H).

2. 3-Allyl-4-hydroxy-benzonitrile, INT 25

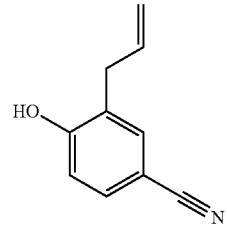

INT 24 (26.9 g, 169 mmol) was heated neat at 200° C. for 20 hours. After cooling down, the residue was purified by chromatography on silica gel (cyclohexane/EtOAc) to give INT 25.

LC/MS method 3: MS (ESI): 160 [M+H]$^+$, rt=1.11 min. $^1$H-NMR (CDCl$_3$): δ (ppm) 7.46-7.43 (m, 1H), 7.43 (s, 1H), 6.88 (d, 2H), 5.98 (m, 1H), 5.89 (s, 1H), 5.25-5.13 (m, 2H), (dd, 1H), 3.42 (d, 1H).

3. 2-Allyl-4-cyanophenyl 2,2,2-trichloroacetate, INT 26

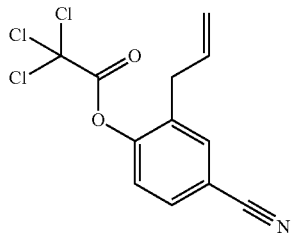 [SMILES: C=CCc1cc(C#N)ccc1OC(=O)C(Cl)(Cl)Cl]

To a solution of INT 25 (10.0 g, 62.8 mmol) in dichoromethane (450 mL) was added triethylamine (7.98 g, 79 mmol), followed by dropwise addition of trichloroacetyl chloride (14.42 g, 79 mmol) and the resulting mixture was stirred at room temperature overnight. The mixture was washed with saturated aqueous ammonium chloride and saturated aqueous sodium bicarbonate. The organic layer was dried over sodium sulfate, filtered and concentrated to give INT 26 which was used in the next step without further purification.

$^1$H-NMR (CDCl$_3$): δ (ppm) 7.65-7.62 (m, 2H), 7.33 (d, 1H), 5.89 (m, 1H), 5.89 (s, 1H), 5.21-5.18 (m, 1H), 5.14-5.08 (m, 1H), (dd, 1H), 3.42 (d, 1H).

4. 5-Chloro-naphthalene-2-carbonitrile, INT 27

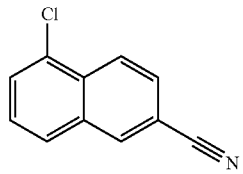 [SMILES: N#Cc1ccc2c(Cl)cccc2c1]

A solution of INT 26 (1.01 g, 3.6 mmol) in degassed 1,2-dichloroethane (20 mL) containing CuCl (14.3 mg, 0.144 mmol) and 1,3-bis(pyridin-2-ylmethyl)-1H-imidazol-3-ium chloride (41.3 mg, 0.144 mmol, prepared according to: Journal of Organometallic Chemistry (2001), Vol. 617-618, 546-560.) was irradiated in the microwave for 2 hours at 200° C. and concentrated. The residue was purified by flash chromatography on silica gel (cyclohexane/EtOAc) to give INT 27.

$^1$H-NMR (DMSO-d$_6$): δ (ppm) 8.72 (s, 1H), 8.32 (d, 1H), 8.10 (d, 1H), 7.97 (d, 1H), 7.93 (d, 1H), 7.69 (t, 1H).

5. 1-(5-Chloro-naphthalen-2-yl)-propan-1-one, INT 28

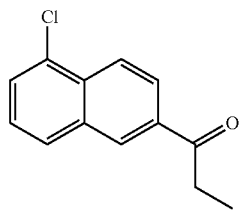

To a solution of INT 27 (2.27 g, 12.1 mmol) in benzene (37 mL) was added dropwise ethylmagnesium bromide (3 M in Et$_2$O, 8.07 mL, 24.2 mmol) and the resulting mixture was refluxed for 3 hours. The mixture was cooled to 0° C. and 6 M HCl (19.4 mL) was added dropwise and the mixture was refluxed for 2 hours. After cooling down, the organic layer was separated and the aqueous layer was extracted with EtOAc. The combined organic layers were washed with brine, dried over sodium sulfate, filtered and concentrated. The residue was purified by flash chromatography on silica gel (cyclohexane/EtOAc) to give INT 28.

LC/MS method 2: MS (ESI): 219 [M+H]$^+$, rt=2.85 min.
$^1$H-NMR (DMSO-d$_6$): δ (ppm) 8.76 (s, 1H), 8.24 (d, 1H), 8.15 (t, 1H), 8.14 (t, 1H), 7.84 (d, 1H), 7.61 (t, 1H).

Alternatively, agents of the invention may be prepared by a reaction sequence involving Buchwald coupling of an appropriate amine with an appropriate protected halobenzaldehyde or halo-pyridyl-carbaldehyde, deprotection, reductive amination with an appropriate amino ester or amino acid followed by an optional deprotection step as shown in Scheme 3 below:

Scheme 3:

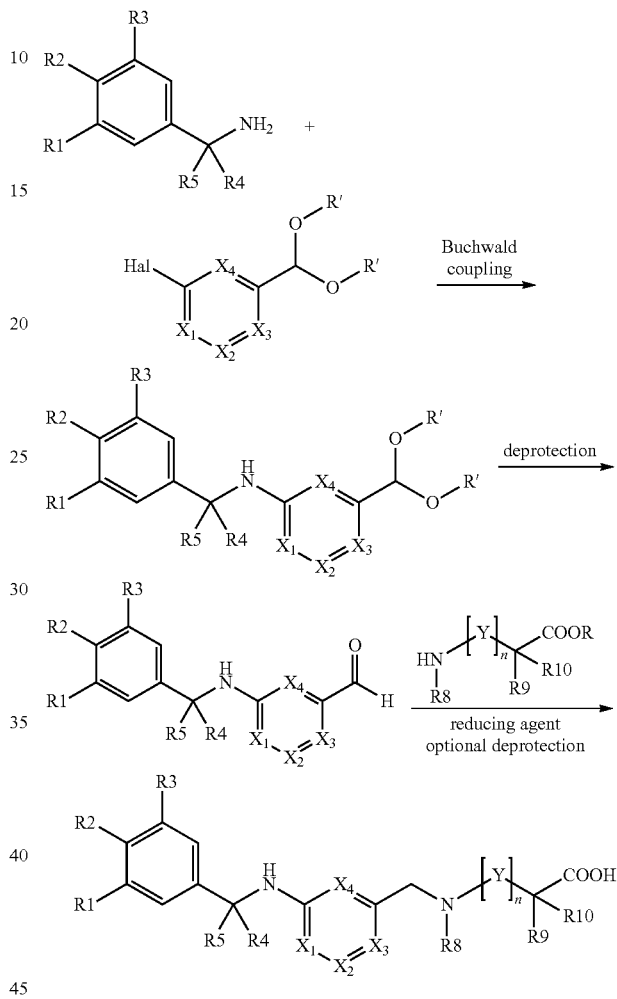

The following compounds were made in accordance to the above indicated reaction Scheme 3:

EXAMPLE 21

(R)-1-{5-[(S)-1-(4-Chloro-3-methyl-phenyl)-2,22-trifluoro-ethylamino]-2-methyl-benzyl}-pyrrolidine-3-carboxylic acid

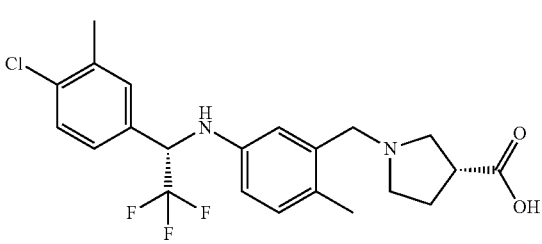 [SMILES: Cc1cc([C@H](Nc2ccc(C)c(CN3CC[C@@H](C(=O)O)C3)c2)C(F)(F)F)ccc1Cl]

1. (5-Bromo-2-methyl-phenyl)-methanol, INT 29

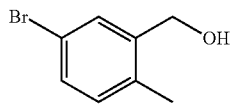

To a solution of 5-bromo-2-methylbenzoic acid (25.00 g, 116 mmol) in THF (250 mL) at 0° C. was added borane dimethyl sulfide complex (2.0 M in THF, 87 mL, 174 mmol) dropwise. The reaction mixture was stirred at room temperature for 16 hours. The mixture was cooled to 0° C. and quenched by dropwise addition of MeOH (100 mL) within 15 minutes. The mixture was stirred at 0° C. for 15 minutes and concentrated. The residue was taken up in EtOAc and washed with 1 M HCl, saturated aqueous NaHCO$_3$ and brine. The organic layer was dried over MgSO$_4$, filtered and concentrated to give INT 29.

MS (ESI): 199 [M−H]$^-$. $^1$H-NMR (CDCl$_3$): δ (ppm) 7.53 (d, 1H), 7.33 (dd, 1H), 7.04 (d, 1H), 4.65 (s, 2H), 2.28 (s, 3H), 2.00 (s, 1H).

2. 5-Bromo-2-methyl-benzaldehyde, INT 30

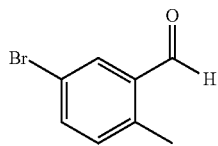

To a solution of INT 29 (19.3 g, 96 mmol) in dioxane (800 mL) was added manganese dioxide (50.2 g, 577 mmol). The reaction mixture was stirred at 80° C. for 3 h. The mixture was filtered over Celite and the filtrate was concentrated to give INT 30.

MS (ESI): 197 [M−H]$^-$. $^1$H-NMR (CDCl$_3$): δ (ppm) 10.23 (s, 1H), 7.92 (d, 1H), 7.60 (dd, 1H), 7.16 (d, 1H), 2.63 (s, 3H).

3. 2-(5-Bromo-2-methyl-phenyl)-[1,3]-dioxolane, INT 31

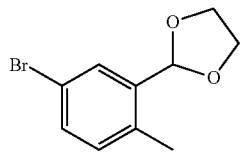

To a solution of INT 30 (17.3 g, 87 mmol) in toluene (505 mL) was added ethane-1,2-diol (24.3 mL, 436 mmol) followed by p-toluenesulfonic acid monohydrate (0.83 g, 4.36 mmol). The reaction mixture was stirred at 130° C. for 21 hours. The mixture was washed with saturated aqueous NaHCO$_3$ (2×) and brine (2×). The organic layer was dried over MgSO$_4$, filtered and concentrated. The residue was purified by Kugelrohr distillation to give INT 31.

MS (ESI): 243 [M+H]$^+$, $^1$H-NMR (CDCl$_3$): δ (ppm) 7.70 (d, 1H), 7.39 (dd, 1H), 7.06 (d, 1H), 5.91 (s, 1H), 4.18-4.03 (m, 4H), 2.38 (s, 3H).

4. [(S)-1-(4-Chloro-3-methyl-phenyl)-2,2,2-trifluoro-ethyl]-(3-[1,3]dioxolan-2-yl-4-methyl-phenyl)-amine, INT 32

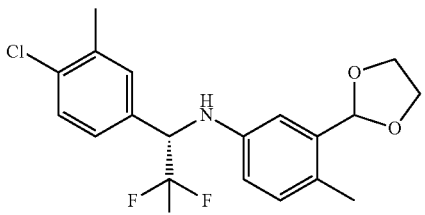

(S)-1-(4-Chloro-3-methyl-phenyl)-2,2,2-trifluoro-ethylamine hydrochloride (5.00 g, 19.22 mmol) was taken up in EtOAc and washed with saturated aqueous NaHCO$_3$, water (3×) and brine (2×). The organic layer was dried over MgSO$_4$, filtered and concentrated. To a solution of the residue and bromide INT 31 (6.08 g, 24.99 mmol) in toluene (83 mL) and tert-butanol (33 mL) was added XPhos (1.83 g, 3.84 mmol) followed by Cs$_2$CO$_3$ (18.79 g, 57.67 mmol). The mixture was degassed for 10 minutes and Pd(OAc)$_2$ (0.43 g, 1.92 mmol) was added. The reaction mixture was stirred at 100° C. for 4 hours. The mixture was diluted with EtOAc and washed with H$_2$O (3×). The aqueous layer was extracted with EtOAc. The combined organic layers were washed with brine (2×), dried over MgSO$_4$, filtered and concentrated. The residue was purified by chromatography on silica gel (heptane/EtOAc) to afford INT 32.

MS (ESI): 386 [M+H]$^+$, $^1$H-NMR (CDCl$_3$): δ (ppm) 7.37-7.32 (m, 2H), 7.22 (br d, 1H), 6.98 (d, 1H), 6.93 (d, 1H), 6.50 (dd, 1H), 5.90 (s, 1H), 4.87 (q, 1H), 4.30 (br s, 1H), 4.12-4.00 (m, 4H), 2.40 (s, 3H), 2.30 (s, 3H).

5. 5-[(S)-1-(4-Chloro-3-methyl-phenyl)-2,2,2-trifluoro-ethylamino]-2-methyl-benzaldehyde, INT 33

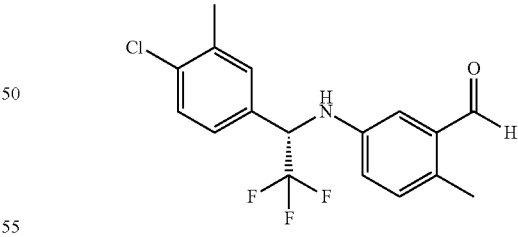

To a solution of acetal INT 32 (4.91 g, 12.73 mmol) in THF (127 mL) at 0° C. was added HCl (2 M in H$_2$O, 25.5 mL, 50.92 mmol). The reaction mixture was stirred at room temperature for 100 minutes. The mixture was diluted with EtOAc and washed with saturated aqueous NaHCO$_3$ (2×), water (2×) and brine (1×). The organic layer was dried over MgSO$_4$, filtered and concentrated to give INT 33.

MS (ESI): 342 [M+H]$^+$, $^1$H-NMR (CDCl$_3$): δ (ppm) 10.23 (s, 1H), 7.38 (d, 1H), 7.34 (s, 1H), 7.25 (d, 1H), 7.11 (d, 1H), 7.08 (d, 1H), 6.80 (dd, 1H), 4.92 (q, 1H), 4.43 (br s, 1H), 2.55 (s, 3H), 2.40 (s, 3H).

6. (R)-1-{5-[(S)-1-(4-Chloro-3-methyl-phenyl)-2,2,2-trifluoro-ethylamino]-2-methyl-benzyl}-pyrrolidine-3-carboxylic acid To a solution of aldehyde INT 33 (2.50 g, 7.32 mmol) and (R)-pyrrolidine-3-carboxylic acid (0.93 g, 8.05 mmol) in MeOH (74 mL) was added HOAc (0.42 mL, 7.32 mmol) followed by PS—CNBH$_3$ (2.5 mmol/g, 2.93 g, 7.32 mmol). The reaction mixture was stirred at room temperature overnight. The mixture was filtered through Celite. The filtrate was concentrated. The residue was taken up in EtOAc and washed with saturated aqueous NaHCO$_3$ and water. The aqueous layers were extracted with EtOAc (2×). The combined organic layers were washed with brine, dried over MgSO$_4$, filtered and concentrated. The residue was purified by chromatography on silica gel (CH$_2$Cl$_2$/MeOH) to afford the title compound Example 21.

LC/MS method 2: MS (ESI): 441 [M+H]$^+$, rt=1.93 min.
$^1$H-NMR (DMSO-d$_6$): δ (ppm) 11.65 (br s, 1H), 7.59 (s, 1H), 7.48-7.40 (m, 2H), 6.83 (d, 1H), 6.80 (s, 1H), 6.62 (dd, 1H), 6.46 (d, 1H), 5.50-5.40 (m, 1H), 3.44 (br s, 2H), 2.97-2.87 (m, 1H), 2.74-2.66 (m, 1H), 2.63-2.54 (m, 1H), 2.49-2.42 (m, 2H), 2.31 (s, 3H), 2.10 (s, 3H), 1.98-1.91 (m, 2H).

EXAMPLE 22

1-{5-[(R)-1-(4-Chloro-3-methyl-phenyl)-propylamino]-2-methyl-benzyl}-azetidine-3-carboxylic acid

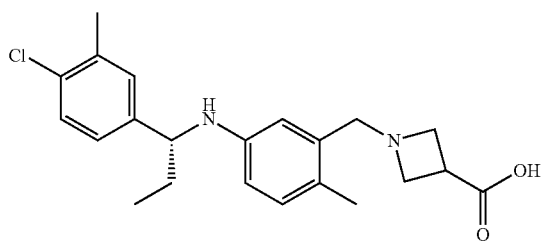 [SMILES: CC[C@@H](Nc1ccc(C)c(CN2CC(C(=O)O)C2)c1)c1ccc(Cl)c(C)c1]

The title compound was prepared according to Scheme 3 following a procedure analogous to Example 21 using (R)-1-(4-chloro-3-methyl-phenyl)-propylamine hydrochloride in step 4 and azetidine-3-carboxylic acid in step 6.
LC/MS method 2: MS (ESI): 387 [M+H]$^+$, rt=2.05 min.

EXAMPLE 23

(R)-1-{5-[(R)-1-(4-Chloro-3-methyl-phenyl)-propylamino]-2-methyl-benzyl}-pyrrolidine-3-carboxylic acid

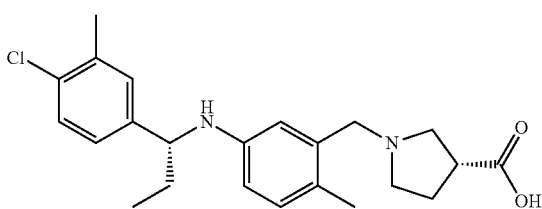

The title compound was prepared according to Scheme 3 following a procedure analogous to Example 21 using (R)-1-(4-chloro-3-methyl-phenyl)-propylamine hydrochloride in step 4.
LC/MS method 2: MS (ESI): 401 [M+H]$^+$, rt=2.07 min.

EXAMPLE 24

1-{3-[(R)-1-(4-Chloro-3-methyl-phenyl)-propylamino]-2-fluoro-benzyl}-azetidine-3-carboxylic acid

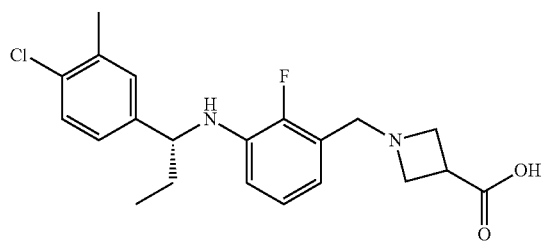 [SMILES: CC[C@@H](Nc1cccc(CN2CC(C(=O)O)C2)c1F)c1ccc(Cl)c(C)c1]

The title compound was prepared according to Scheme 3 following a procedure analogous to steps 3 to 6 of Example 21 using 3-bromo-2-fluoro-benzaldehyde in step 3, (R)-1-(4-chloro-3-methyl-phenyl)-propylamine hydrochloride in step 4 and azetidine-3-carboxylic acid in step 6.
LC/MS method 2: MS (ESI): 391 [M+H]$^+$, rt=2.08 min.

EXAMPLE 25

(R)-1-{3-[(R)-1-(4-Chloro-3-methyl-phenyl)-propylamino]-2-fluoro-benzyl}-pyrrolidine-3-carboxylic acid

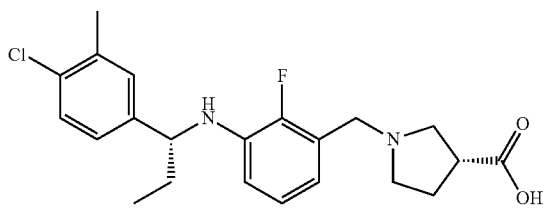 [SMILES: CC[C@@H](Nc1cccc(CN2CC[C@@H](C(=O)O)C2)c1F)c1ccc(Cl)c(C)c1]

The title compound was prepared according to Scheme 3 following a procedure analogous to steps 3 to 6 of Example 21 using 3-bromo-2-fluoro-benzaldehyde in step 3 and (R)-1-(4-chloro-3-methyl-phenyl)-propylamine hydrochloride in step 4.
LC/MS method 2: MS (ESI): 405 [M+H]$^+$, rt=2.12 min.

EXAMPLE 26

1-{3-[(R)-1-(4-Chloro-3-methyl-phenyl)-propylamino]-4-fluoro-benzyl}-azetidine-3-carboxylic acid

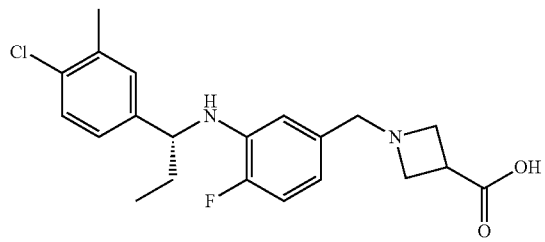

The title compound was prepared according to Scheme 3 following a procedure analogous to steps 3 to 6 of Example 21 using 3-bromo-4-fluoro-benzaldehyde in step 3, (R)-1-(4-chloro-3-methyl-phenyl)-propylamine hydrochloride in step 4 and azetidine-3-carboxylic acid in step 6.

LC/MS method 2: MS (ESI): 391 [M+H]+, rt=2.00 min.

EXAMPLE 27

(R)-1-{3-[(R)-1-(4-Chloro-3-methyl-phenyl)-propylamino]-4-fluoro-benzyl}-pyrrolidine-3-carboxylic acid

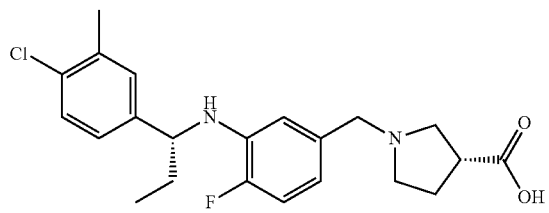 [SMILES: CC[C@@H](Nc1cc(CN2CC[C@@H](C(=O)O)C2)ccc1F)c1ccc(Cl)c(C)c1]

The title compound was prepared according to Scheme 3 following a procedure analogous to steps 3 to 6 of Example 21 using 3-bromo-4-fluoro-benzaldehyde in step 3 and (R)-1-(4-chloro-3-methyl-phenyl)-propylamine hydrochloride in step 4.

LC/MS method 2: MS (ESI): 405 [M+H]+, rt=2.02 min.

EXAMPLE 28

1-{5-[(R)-1-(4-Chloro-3-methyl-phenyl)-propylamino]-2-methyl-benzyl}-3-methyl-azetidine-3-carboxylic acid

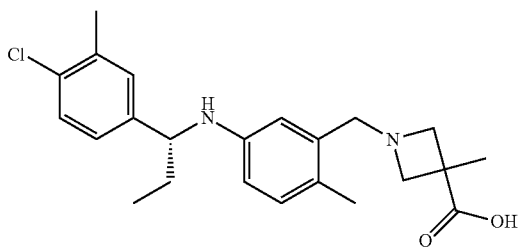 [SMILES: CC[C@@H](Nc1ccc(C)c(CN2CC(C)(C(=O)O)C2)c1)c1ccc(Cl)c(C)c1]

The title compound was prepared according to Scheme 3 following a procedure analogous to Example 21 using (R)-1-(4-chloro-3-methyl-phenyl)-propylamine hydrochloride in step 4 and INT 14 in step 6 followed by a LiOH-mediated deprotection.

LC/MS method 2: MS (ESI): 401 [M+H]+, rt=2.11 min.

EXAMPLE 29

(R)-1-{2-Chloro-5-[(S)-1-(4-chloro-3-methyl-phenyl)-2,2,2-trifluoro-ethylamino]-benzyl}-pyrrolidine-3-carboxylic acid

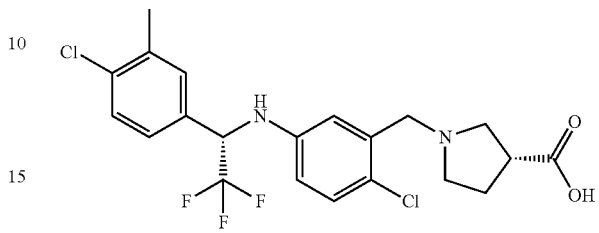

The title compound was prepared according to Scheme 3 following a procedure analogous to steps 2 to 6 of Example 21 using 5-bromo-2-chloro-benzylalcohol in step 2.

LC/MS method 2: MS (ESI): 461 [M+H]+, rt=2.07 min.

EXAMPLE 30

(R)-1-{3-[(S)-1-(4-Chloro-3-methyl-phenyl)-2,2,2-trifluoro-ethylamino]-2,6-dimethyl-benzyl}-pyrrolidine-3-carboxylic acid

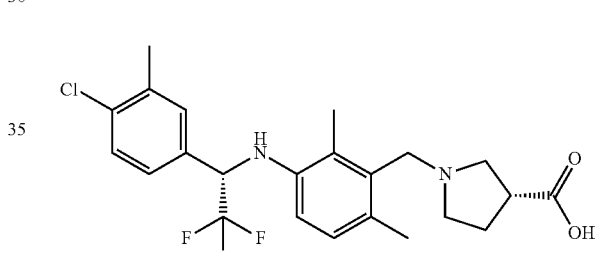

The title compound was prepared according to Scheme 3 following a procedure analogous to Example 21 using INT 34 (synthesis below) in step 1.

LC/MS method 2: MS (ESI): 455 [M+H]+, rt=2.17 min.

1. 3-Bromo-2,6-dimethyl-benzoic acid, INT 34

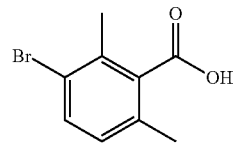

To a solution of 2,6-dimethylbenzoic acid (25.00 g, 166 mmol) in HOAc (432 mL) was added NaOAc (16.39 g, 200 mmol) followed by bromine (11.2 mL, 216 mmol). The reaction mixture was stirred at room temperature overnight. The mixture was poured onto ice water (800 mL) and stirred for 20 minutes. The solid was filtered off, washed with $H_2O$ and dried at 50° C. under vacuum to give INT 34.

MS (ESI): 227 [M−H]−. 1H-NMR (DMSO-$d_6$): δ (ppm) 13.40 (br s, 1H), 7.53 (d, 1H), 7.05 (d, 1H), 2.31 (s, 3H), 2.23 (s, 3H).

EXAMPLE 31

1-{3-[(S)-1-(4-Chloro-3-methyl-phenyl)-2,2,2-trifluoro-ethylamino]-2,6-dimethyl-benzyl}-azetidine-3-carboxylic acid

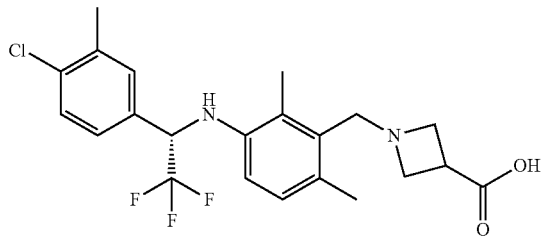 [SMILES: Cc1cc([C@H](Nc2ccc(C)c(CN3CC(C(=O)O)C3)c2C)C(F)(F)F)ccc1Cl]

The title compound was prepared according to Scheme 3 following a procedure analogous to Example 21 using INT 34 in step 1 and azetidine-3-carboxylic acid in step 6.

LC/MS method 2: MS (ESI): 441 [M+H]$^+$, rt=2.15 min.

EXAMPLE 32

(R)-1-{3-[(R)-1-(4-Chloro-3-methyl-phenyl)-propylamino]-2,6-dimethyl-benzyl}-pyrrolidine-3-carboxylic acid

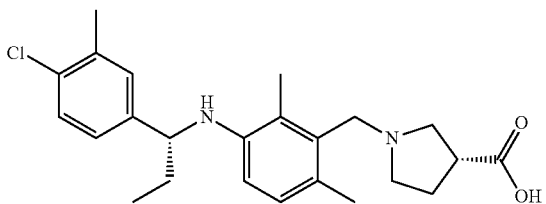 [SMILES: CC[C@@H](Nc1ccc(C)c(CN2CC[C@@H](C(=O)O)C2)c1C)c1ccc(Cl)c(C)c1]

The title compound was prepared according to Scheme 3 following a procedure analogous to Example 21 using INT 34 in step 1 and (R)-1-(4-chloro-3-methyl-phenyl)-propylamine hydrochloride in step 4.

LC/MS method 2: MS (ESI): 415 [M+H]$^+$, rt=2.32 min.

EXAMPLE 33

1-{3-[(R)-1-(4-Chloro-3-methyl-phenyl)-propylamino]-2,6-dimethyl-benzyl}-azetidine-3-carboxylic acid

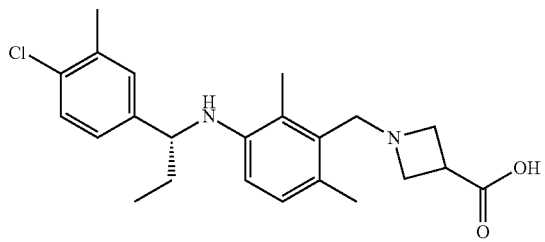 [SMILES: CC[C@@H](Nc1ccc(C)c(CN2CC(C(=O)O)C2)c1C)c1ccc(Cl)c(C)c1]

The title compound was prepared according to Scheme 3 following a procedure analogous to Example 21 using INT 34 in step 1, (R)-1-(4-chloro-3-methyl-phenyl)-propylamine hydrochloride in step 4 and azetidine-3-carboxylic acid in step 6.

LC/MS method 2: MS (ESI): 401 [M+H]$^+$, rt=2.26 min.

EXAMPLE 34

(R)-1-{5-[(S)-1-(4-Chloro-3-methyl-phenyl)-2,2,2-trifluoro-ethylamino]-2-ethyl-benzyl}-pyrrolidine-3-carboxylic acid

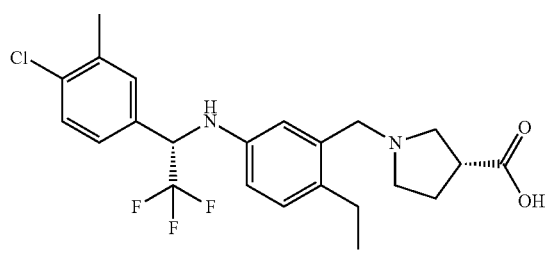 [SMILES: CCc1ccc(N[C@@H](c2ccc(Cl)c(C)c2)C(F)(F)F)cc1CN1CC[C@@H](C(=O)O)C1]

The title compound was prepared according to Scheme 3 following a procedure analogous to steps 3 to 6 of Example 21 using aldehyde INT 35 (synthesis below) in step 3.

LC/MS method 2: MS (ESI): 455 [M+H]$^+$, rt=2.19 min.

1. 5-Bromo-2-ethyl-benzaldehyde, INT 35

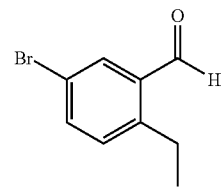

To a solution of 2-ethyl-benzaldehyde (5.00 g, 37.3 mmol) in CH$_2$Cl$_2$ (23 mL) was carefully added AlCl$_3$ (8.70 g, 65.2 mmol). The mixture was cooled to 0° C. and a solution of bromine (1.9 mL, 37.2 mmol) in CH$_2$Cl$_2$ (23 mL) was added over 6 hours. The reaction mixture was stirred at room temperature overnight. The mixture was poured onto an ice/water mixture and stirred for 10 minutes. The aqueous layer was extracted with EtOAc (2×). The combined organic layers were washed with 2 M HCl, saturated aqueous NaHCO$_3$ and brine, dried over MgSO$_4$, filtered and concentrated. The residue was purified by chromatography on silica gel (heptane/EtOAc) to afford INT 35.

MS (ESI): 211 [M−H]$^−$. $^1$H-NMR (CDCl$_3$): δ (ppm) 10.24 (s, 1H), 7.95 (d, 1H), 7.63 (dd, 1H), 7.20 (d, 1H), 3.01 (q, 2H), 1.28 (t, 3H).

Example 35

1-{5-[(S)-1-(4-Chloro-3-methyl-phenyl)-2,22-trifluoro-ethylamino]-2-ethyl-benzyl}-azetidine-3-carboxylic acid

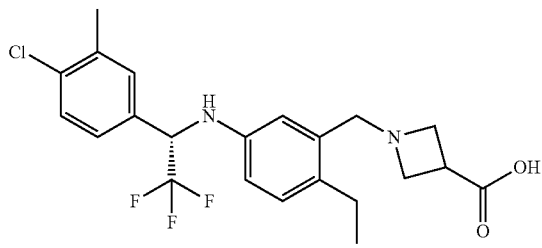 [SMILES: CCc1ccc(N[C@@H](c2ccc(Cl)c(C)c2)C(F)(F)F)cc1CN1CC(C(=O)O)C1]

The title compound was prepared according to Scheme 3 following a procedure analogous to steps 3 to 6 of Example 21 using aldehyde INT 35 in step 3 and azetidine-3-carboxylic acid in step 6.
LC/MS method 2: MS (ESI): 441 [M+H]$^+$, rt=2.16 min.

Example 36

(R)-1-{5-[(R)-1-(4-Chloro-3-methyl-phenyl)-propylamino]-2-ethyl-benzyl}-pyrrolidine-3-carboxylic acid

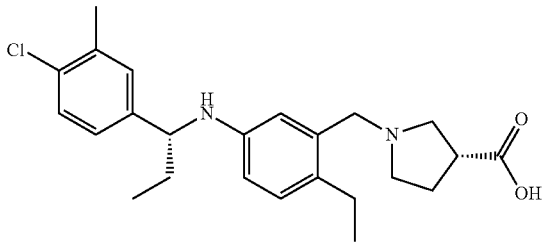 [SMILES: CCc1ccc(N[C@H](CC)c2ccc(Cl)c(C)c2)cc1CN1CC[C@@H](C(=O)O)C1]

The title compound was prepared according to Scheme 3 following a procedure analogous to steps 3 to 6 of Example 21 using aldehyde INT 35 in step 3 and (R)-1-(4-chloro-3-methyl-phenyl)-propylamine hydrochloride in step 4.
LC/MS method 2: MS (ESI): 415 [M+H]$^+$, rt=2.22 min.

Example 37

1-{5-[(R)-1-(4-Chloro-3-methyl-phenyl)-propylamino]-2-ethyl-benzyl}-azetidine-3-carboxylic acid

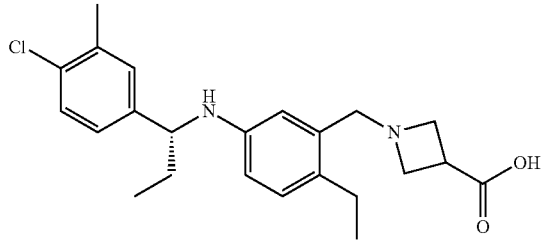 [SMILES: CCc1ccc(N[C@H](CC)c2ccc(Cl)c(C)c2)cc1CN1CC(C(=O)O)C1]

The title compound was prepared according to Scheme 3 following a procedure analogous to steps 3 to 6 of Example 21 using aldehyde INT 35 in step 3, (R)-1-(4-chloro-3-methyl-phenyl)-propylamine hydrochloride in step 4 and azetidine-3-carboxylic acid in step 6.
LC/MS method 2: MS (ESI): 401 [M+H]$^+$, rt=2.20 min.

Example 38

(R)-1-{2-Chloro-5-[(R)-1-(4-chloro-3-methyl-phenyl)-propylamino]-benzyl}-pyrrolidine-3-carboxylic acid

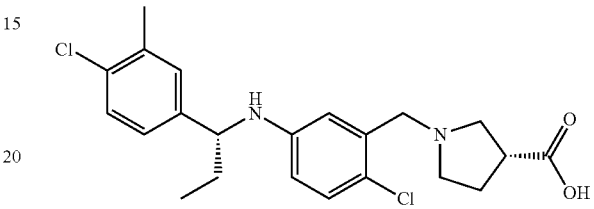

The title compound was prepared according to Scheme 3 following a procedure analogous to steps 2 to 6 of Example 21 using 5-bromo-2-chloro-benzylalcohol in step 2 and (R)-1-(4-chloro-3-methyl-phenyl)-propylamine hydrochloride in step 4.
LC/MS method 2: MS (ESI): 421 [M+H]$^+$, rt=2.13 min.

Example 39

1-{3-[(S)-1-(4-Chloro-3-methyl-phenyl)-2,2,2-trifluoro-ethylamino]-2-methyl-benzyl}-azetidine-3-carboxylic acid

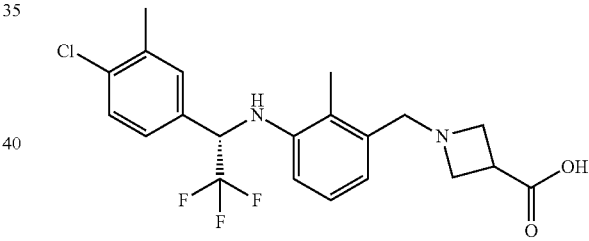

The title compound was prepared according to Scheme 3 following a procedure analogous to Example 21 using 3-bromo-2-methylbenzoic acid in step 1 and azetidine-3-carboxylic acid in step 6.
LC/MS method 2: MS (ESI): 427 [M+H]$^+$, rt=2.03 min.

Example 40

3-{3-[(S)-1-(4-Chloro-3-methyl-phenyl)-2,2,2-trifluoro-ethylamino]-2,6-dimethyl-benzylamino}-propionic acid

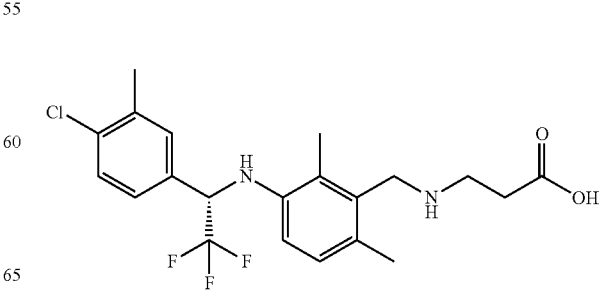

The title compound was prepared according to Scheme 3 following a procedure analogous to Example 21 using INT 34 in step 1 and 3-aminopropionic acid in step 6.

LC/MS method 2: MS (ESI): 429 [M+H]⁺, rt=2.13 min.

Example 41

1-{5-[(R)-1-(4-Chloro-3,5-dimethyl-phenyl)-propylamino]-2-methyl-benzyl}-azetidine-3-carboxylic acid

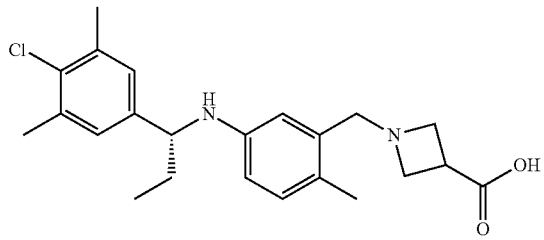 [SMILES: CC[C@@H](Nc1ccc(C)c(CN2CC(C(=O)O)C2)c1)c1cc(C)c(Cl)c(C)c1]

The title compound was prepared according to Scheme 3 following a procedure analogous to Example 21 using amine INT 38 (synthesis below) in step 4 and azetidine-3-carboxylic acid in step 6.

LC/MS method 2: MS (ESI): 401 [M+H]⁺, rt=2.20 min.

1. (R)-2-Methyl-propane-2-sulfinic acid 1-(4-chloro-3,5-dimethyl-phenyl)-meth-(E)-ylideneamide, INT 36

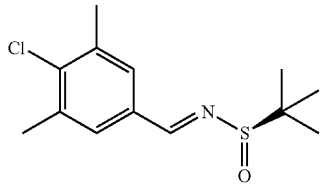 [SMILES: Cc1cc(/C=N/[S@](=O)C(C)(C)C)cc(C)c1Cl]

A solution of 4-chloro-3,5-dimethyl-benzaldehyde (6.04 g, 35.8 mmol) and (R)-2-methylpropane-2-sulfinamide (4.78 g, 39.4 mmol) in toluene (110 mL) was treated with titanium (IV) isopropoxide (15.74 mL, 53.7 mmol). The mixture was stirred at 50° C. for 24 hours. It was then quenched with 10% aqueous sodium bicarbonate solution (100 mL) and filtered through Celite. The filter cake was washed with Et₂O (250 mL). The organic layers were washed with water and brine, dried over sodium sulfate, filtered and concentrated. The crude was purified by chromatography on silica gel (cyclohexane/EtOAc).

UPLC: rt=2.32 min. ¹H-NMR (CDCl₃): δ (ppm) 8.49 (s, 1H), 7.56 (s, 2H), 2.44 (s, 6H), 1.26 (s, 9H).

2. (R)-2-Methyl-propane-2-sulfinic acid [(R)-1-(4-chloro-3,5-dimethyl-phenyl)-propyl]-amide, INT 37

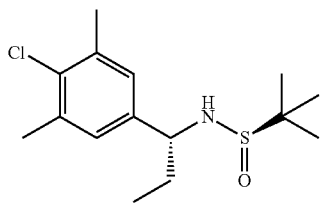 [SMILES: CC[C@@H](N[S@](=O)C(C)(C)C)c1cc(C)c(Cl)c(C)c1]

To a solution of dimethylzinc (1.7 M in toluene, 10.95 mL, 21.89 mmol) was added dropwise a solution of ethylmagnesium bromide (3 M Et₂O, 6.44 mL, 19.32 mmol) at room temperature and the mixture was stirred for 15 minutes.

In a separate flask a solution of INT 36 (3.5 g, 12.88 mmol) in THF (100 mL) was cooled in a dry ice bath under argon to −78° C. At this temperature the organozincate solution from above was added dropwise over a period of about 30 minutes. Stirring was continued for another 90 minutes before the resulting mixture was first quenched carefully with 10% ammonium chloride solution (40 mL), then water (50 mL). The reaction mixture was allowed to warm up to room temperature and was then extracted with Et₂O (200 mL). The organic layer was washed with water and brine, dried over sodium sulfate, filtered and concentrated. The crude was purified by chromatography on silica gel (cyclohexane/EtOAc).

UPLC: rt=2.06 min. ¹H-NMR (CDCl₃): δ (ppm) 7.01 (s, 2H), 4.16 (m, 1H), 3.30 (br d, 1H), 2.37 (s, 6H), 2.01 (m, 1H), 1.70 (m, 1H), 1.22 (s, 9H), 0.80 (t, 3H).

3. (R)-1-(4-Chloro-3,5-dimethyl-phenyl)-propylamine, INT 38

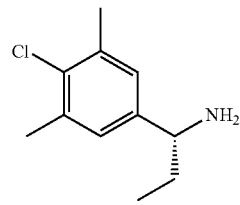

A solution of intermediate INT 37 (3.4 g, 11.26 mmol) in MeOH (75 mL) was treated with HCl (4 M in dioxane, 5.63 mL, 22.53 mmol) and stirred overnight. After evaporation of the solvents, a white solid was obtained which was washed with Et₂O. The solid was then dissolved in water, slightly acidified with 2 M HCl and washed with EtOAc. The aqueous layer was separated and the pH adjusted to about 11 using 2 M NaOH followed by extraction with Et₂O (3×). The Et₂O layers were combined, dried over sodium sulfate, filtered and concentrated.

UPLC: rt=1.00 min. ¹H-NMR (CDCl₃): δ (ppm) 7.05 (s, 2H), 3.75 (m, 1H), 2.39 (s, 6H), 2.06 (br s, 2H), 1.69 (m, 2H), 0.88 (t, 3H).

Example 42

(R)-1-{5-[(R)-1-(4-Chloro-3,5-dimethyl-phenyl)-propylamino]-2-methyl-benzyl}-pyrrolidine-3-carboxylic acid

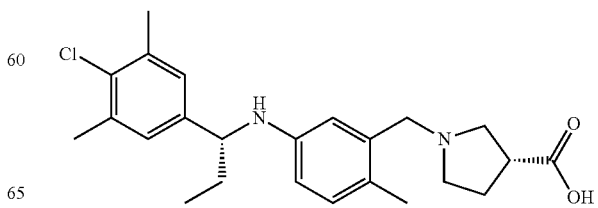

The title compound was prepared according to Scheme 3 following a procedure analogous to Example 21 using amine INT 38 in step 4.

LC/MS method 2: MS (ESI): 415 [M+H]⁺, rt=2.25 min.

Example 43

(R)-1-{2-Chloro-5-[(R)-1-(4-chloro-3,5-dimethyl-phenyl)-propylamino]-benzyl}-pyrrolidine-3-carboxylic acid

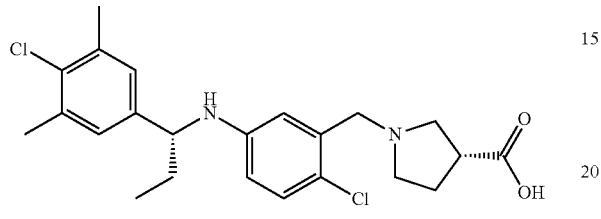

The title compound was prepared according to Scheme 3 following a procedure analogous to steps 2 to 6 of Example 21 using 5-bromo-2-chlorobenzylalcohol in step 2 and amine INT 38 in step 4.

LC/MS method 2: MS (ESI): 435 [M+H]⁺, rt=2.28 min.

Example 44

(R)-1-{5-[(R)-1-(4-Chloro-3,5-dimethyl-phenyl)-ethylamino]-2-methyl-benzyl}-pyrrolidine-3-carboxylic acid

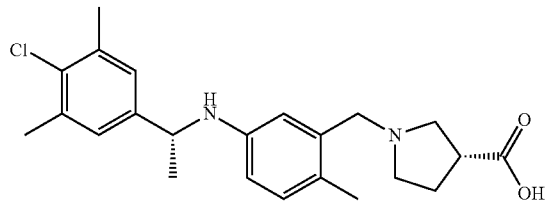 [SMILES: Cc1ccc(N[C@H](C)c2cc(C)c(Cl)c(C)c2)cc1CN1CC[C@@H](C(=O)O)C1]

The title compound was prepared according to Scheme 3 following a procedure analogous to Example 21 using amine INT 41 (synthesis below) in step 4.

LC/MS method 2: MS (ESI): 401 [M+H]⁺, rt=2.07 min.

1. (S)-2-Methyl-propane-2-sulfinic acid 1-(4-chloro-3,5-dimethyl-phenyl)-meth-(E)-ylideneamide, INT 39

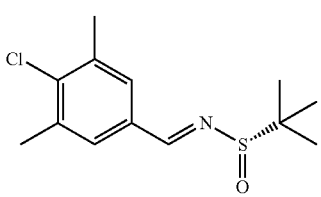 [SMILES: Cc1cc(/C=N/[S@@](=O)C(C)(C)C)cc(C)c1Cl]

A solution of 4-chloro-3,5-dimethyl-benzaldehyde (2 g, 11.86 mmol) and (S)-2-methylpropane-2-sulfinamide (1.58 g, 13.05 mmol) in toluene (35 mL) was treated with titanium (IV) isopropoxide (5.27 mL, 17.79 mmol). The mixture was stirred at 50° C. for 24 hours. It was then quenched with 10% sodium bicarbonate solution (50 mL) and extracted twice with EtOAc. The organic layers were washed with water and brine, dried over sodium sulfate, filtered and concentrated. The crude was purified by chromatography on silica gel (cyclohexane/EtOAc).

UPLC: rt=2.29 min. ¹H-NMR (CDCl₃): δ (ppm) 8.49 (s, 1H), 7.56 (s, 2H), 2.44 (s, 6H), 1.26 (s, 9H).

2. (S)-2-Methyl-propane-2-sulfinic acid [(R)-1-(4-chloro-3,5-dimethyl-phenyl)-ethyl]-amide, INT 40

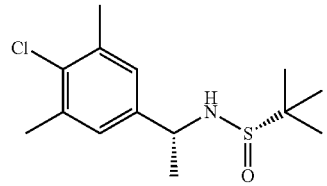 [SMILES: Cc1cc([C@@H](C)N[S@@](=O)C(C)(C)C)cc(C)c1Cl]

A solution of INT 39 (4 g, 14.72 mmol) in CH₂Cl₂ (150 mL) was cooled to −50° C. To this solution was added methylmagnesium bromide (3 M Et₂O, 9.8 mL, 29.4 mmol) at a rate that the temperature did not exceed −48° C. Stirring at this temperature was continued for 6 hours.

UPLC showed conversion of about 30%. The mixture was stored in a freezer at −25° C. for 3 days. Conversion was about 60%. Another portion of methylmagnesium bromide (3 M in Et₂O, 9.8 mL, 29.4 mmol) was added and the mixture was kept another 24 hours in the freezer. Hardly any change in conversion could be detected. Thus, the cold reaction mixture was quenched with saturated ammonium chloride solution. The organic layer was separated and the aqueous layer was extracted with EtOAc (250 mL). The combined organic extracts were washed with 5% ammonium chloride solution, water, 10% sodium bicarbonate solution and brine, dried over sodium sulfate, filtered and concentrated. The crude was purified by chromatography on silica gel (cyclohexane/EtOAc).

MS (ESI): 288.3 [M+H]⁺, ¹H-NMR (CDCl₃): δ (ppm) 7.03 (s, 2H), 4.47 (m, 1H), 3.28 (br s, 1H), 2.36 (s, 6H), 1.49 (d, 3H), 1.20 (s, 9H).

3. (R)-1-(4-Chloro-3,5-dimethyl-phenyl)-ethylamine, INT 41

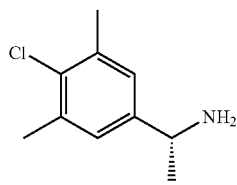

A solution of intermediate INT 40 (2.3 g, 8 mmol) in MeOH (50 mL) was treated with HCl (4 M in dioxane, 4 mL, 16 mmol) and stirred overnight. After evaporation of the solvents, a solid was obtained which was washed with Et₂O. The solid was then dissolved in water, slightly acidified with 2 M HCl and washed with EtOAc. The aqueous layer was separated and the pH adjusted to about 11 using 2 M NaOH followed by extraction with Et₂O (3×). The Et₂O layers were combined, dried over sodium sulfate, filtered and concentrated.

UPLC: rt=0.87 min. ¹H-NMR (CDCl₃): δ (ppm) 7.10 (s, 2H), 4.08 (m, 1H), 2.39 (s, 6H), 2.33 (br s, 2H), 1.41 (d, 3H).

Example 45

3-{5-[(R)-1-(4-Chloro-3,5-dimethyl-phenyl)-propylamino]-2-methyl-benzylamino}-propionic acid

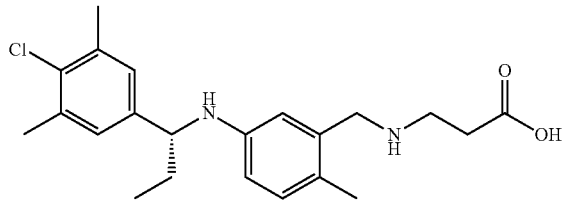 [SMILES: CC[C@@H](Nc1ccc(C)c(CNCCC(=O)O)c1)c1cc(C)c(Cl)c(C)c1]

The title compound was prepared according to Scheme 3 following a procedure analogous to Example 21 using amine INT 38 in step 4 and 3-amino-propionic acid tert-butyl ester in step 6, followed by a HCl/dioxane-induced ester cleavage.
LC/MS method 2: MS (ESI): 389 [M+H]$^+$, rt=2.21 min.

Example 46

(R)-1-{2-Chloro-5-[(R)-1-(4-chloro-3,5-dimethyl-phenyl)-ethylamino]-benzyl}-pyrrolidine-3-carboxylic acid

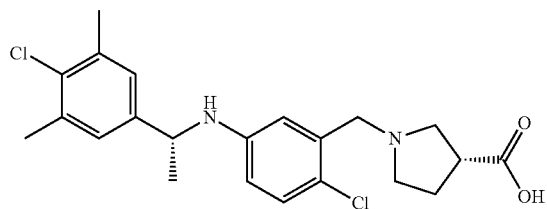 [SMILES: Cc1cc([C@@H](C)Nc2ccc(Cl)c(CN3CC[C@@H](C(=O)O)C3)c2)cc(C)c1Cl]

The title compound was prepared according to Scheme 3 following a procedure analogous to steps 2 to 6 of Example 21 using 5-bromo-2-chlorobenzylalcohol in step 2 and amine INT 41 in step 4.
LC/MS method 2: MS (ESI): 421 [M+H]$^+$, rt=2.09 min.

Example 47

3-{5-[(R)-1-(4-Chloro-3,5-dimethyl-phenyl)-ethylamino]-2-methyl-benzylamino}-propionic acid

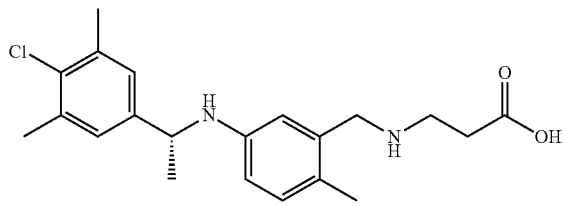 [SMILES: Cc1ccc(N[C@H](C)c2cc(C)c(Cl)c(C)c2)cc1CNCCC(=O)O]

The title compound was prepared according to Scheme 3 following a procedure analogous to Example 21 using amine INT 41 in step 4 and 3-amino-propionic acid tert-butyl ester in step 6, followed by a HCl/dioxane-induced ester cleavage.
LC/MS method 2: MS (ESI): 375 [M+H]$^+$, rt=2.08 min.

Example 48

3-{2-Chloro-5-[(R)-1-(4-chloro-3,5-dimethyl-Phenyl)-propylamino]-benzylamino}-propionic acid

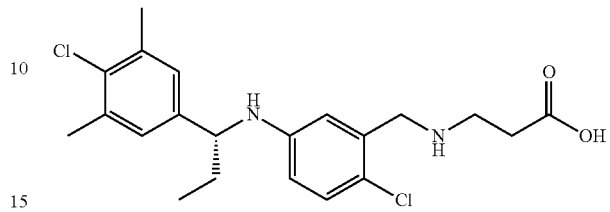

The title compound was prepared according to Scheme 3 following a procedure analogous to steps 2 to 6 of Example 21 using 5-bromo-2-chlorobenzylalcohol in step 2, amine INT 38 in step 4 and 3-amino-propionic acid tert-butyl ester in step 6, followed by a HCl/dioxane-induced ester cleavage.
LC/MS method 2: MS (ESI): 395 [M+H]$^+$, rt=2.08 min.

Example 49

(R)-3-(5-[(R)-1-(4-Chloro-3,5-dimethyl-phenyl)-propylamino)-2-methyl-benzylamino]-2-methyl-propionic acid

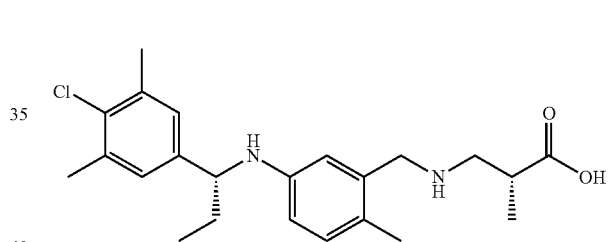

The title compound was prepared according to Scheme 3 following a procedure analogous to Example 21 using amine INT 38 in step 4 and (R)-3-amino-2-methyl-propionic acid methyl ester in step 6, followed by a LiOH-induced ester cleavage.
LC/MS method 1: MS (ESI): 403 [M+H]$^+$, rt=2.42 min.

Example 50

3-{5-[(S)-1-(4-Chloro-3,5-dimethyl-phenyl)-2,2,2-trifluoro-ethylamino]-2-methyl-benzylamino}-propionic acid

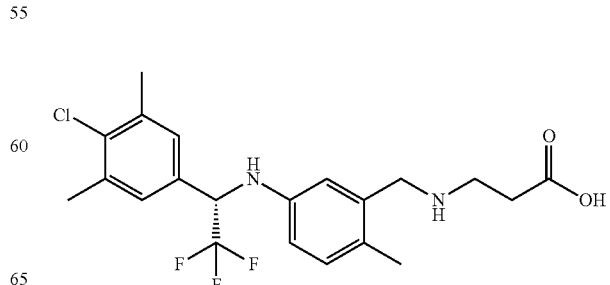

The title compound was prepared according to Scheme 3 following a procedure analogous to Example 21 using amine INT 43 (synthesis below) in step 4 and 3-amino-propionic acid tert-butyl ester in step 6, followed by an HCl/dioxane-induced ester cleavage.

LC/MS method 1: MS (ESI): 429.1 [M+H]$^+$, rt=2.27 min.

1. (R)-2-Methyl-propane-2-sulfinic acid [(S)-1-(4-chloro-3,5-dimethyl-phenyl)-2,2,2-trifluoro-ethyl]-amide, INT 42

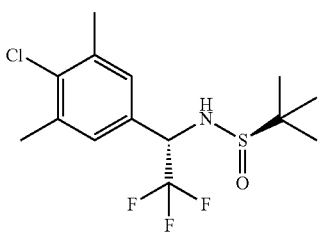 [SMILES: Cc1cc([C@H](N[S@](=O)C(C)(C)C)C(F)(F)F)cc(C)c1Cl]

A solution of TMS-CF$_3$ (0.737 mL, 4.99 mmol) in THF (15 mL) was added to a solution of TBAT (2.469 g, 4.57 mmol) and INT 36 (1.13 g, 4.16 mmol) in THF (60.0 mL) at −65° C. Stirring was continued for 3 hours. Another portion of TBAT (200 mg, 0.37 mmol) was added. After 2 more hours, more TMS-CF$_3$ (0.369 ml, 2.50 mmol) was added. The suspension became a clear solution which was quenched with saturated ammonium chloride solution, diluted with EtOAc and washed with water. The organic layer was dried over sodium sulfate, filtered and concentrated. The crude was purified by chromatography on silica gel (cyclohexane/EtOAc).

MS (ESI): 342 [M+H]$^+$, UPLC: rt=2.06 min.

2. (S)-1-(4-Chloro-3,5-dimethyl-phenyl)-2,2,2-trifluoro-ethylamine, INT 43

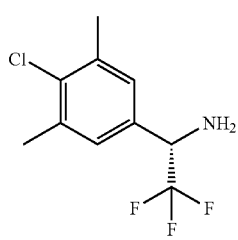

A solution of intermediate INT 42 (860 mg, 2.52 mmol) in MeOH (40 mL) was treated with HCl (4 M in dioxane, 1.26 mL, 5.04 mmol) and stirred over the weekend. After evaporation of the solvents, a solid was obtained which was triturated with Et$_2$O. The solid was then dissolved in water and the pH was adjusted to ~9 using 10% sodium carbonate solution. It was extracted twice with EtOAc. The combined extracts were dried over sodium sulfate, filtered and concentrated.

MS (ESI): 238 [M+H]$^+$, UPLC: rt=1.36 min.

Example 51

3-{2-Chloro-5-[(S)-1-(4-chloro-3,5-dimethyl-phenyl)-2,2,2-trifluoro-ethylamino]-benzylamino}-propionic acid

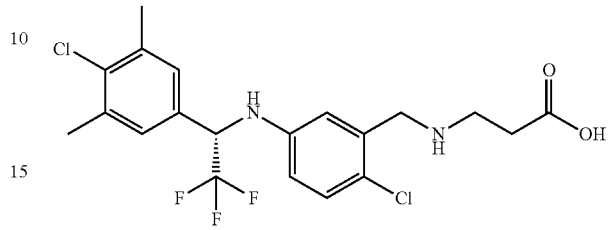

The title compound was prepared according to Scheme 3 following a procedure analogous to steps 2 to 6 of Example 21 using 5-bromo-2-chlorobenzylalcohol in step 2, amine INT 43 in step 4 and 3-amino-propionic acid tert-butyl ester in step 6, followed by a HCl/dioxane-induced ester cleavage.

LC/MS method 2: MS (ESI): 448.9 [M+H]$^+$, rt=2.19 min.

Example 52

3-{2-Chloro-5-[(S)-1-(4-chloro-3-methyl-phenyl)-2,2,2-trifluoro-ethylamino]-benzylamino}-propionic acid

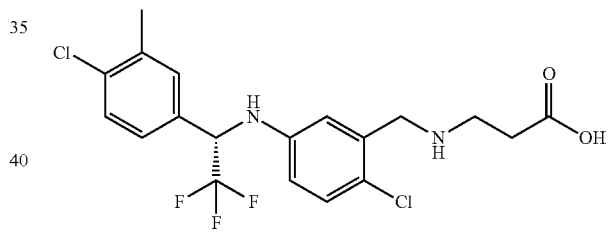

The title compound was prepared according to Scheme 3 following a procedure analogous to steps 2 to 6 of Example 21 using 5-bromo-2-chlorobenzylalcohol in step 2 and 3-amino-propionic acid in step 6.

LC/MS method 2: MS (ESI): 435 [M+H]$^+$, rt=2.09 min.

Example 53

3-{2-Chloro-5-[(R)-1-(4-chloro-3,5-dimethyl-phenyl)-propylamino]-benzylamino}-propionic acid

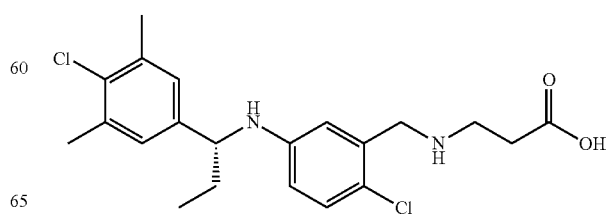

The title compound was prepared according to Scheme 3 following a procedure analogous to steps 2 to 6 of Example 21 using 5-bromo-2-chlorobenzylalcohol in step 2, amine INT 38 in step 4 and 3-amino-propionic acid in step 6.

LC/MS method 2: MS (ESI): 409 [M+H]$^+$, rt=2.24 min.

Example 54

1-{2-[(R)-1-(4-Chloro-3-methyl-phenyl)-propylamino]-5-fluoro-pyridin-4-ylmethyl}-azetidine-3-carboxylic acid

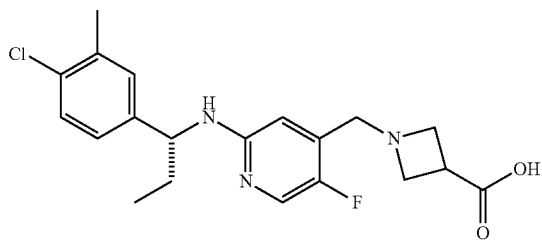

1. 2-Bromo-4-[1,3]dioxolan-2-yl-5-fluoro-pyridine, INT 44

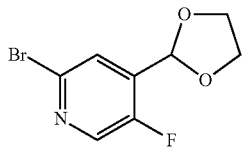

A mixture of 2-bromo-5-fluoroisonicotinaldehyde (495 mg, 2.43 mmol), ethylene glycol (0.27 mL, 4.85 mmol) and p-toluenesulfonic acid monohydrate (508 mg, 2.67 mmol) in toluene (13.5 mL) was refluxed for 4 hours. The mixture was concentrated and taken up in CH$_2$Cl$_2$, washed with 1 M NaOH, dried over sodium sulfate, filtered and concentrated. The crude product was purified by flash chromatography on silica gel (cyclohexane/EtOAc) to give INT 44.

LC/MS method 4: MS (ESI): 249 [M+H]$^+$, rt=0.89 min.
$^1$H-NMR (CDCl$_3$): δ (ppm) 8.25 (s, 1H), 7.62 (d, 1H), 6.04 (s, 1H), 4.18-4.09 (m, 4H).

2. [(R)-1-(4-Chloro-3-methyl-phenyl)-propyl]-(4-[1,3]dioxolan-2-yl-5-fluoro-pyridin-2-yl)-amine, INT 45

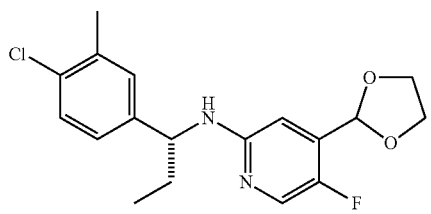 [SMILES: CC[C@@H](Nc1cc(C2OCCO2)c(F)cn1)c1ccc(Cl)c(C)c1]

To a solution of INT 44 (370 mg, 1.492 mmol), (R)-1-(4-chloro-3-methyl-phenyl)-propylamine hydrochloride (394 mg, 1.790 mmol) and sodium tert-butoxide (344 mg, 3.58 mmol) in degassed toluene (5.8 mL) was added Pd$_2$(dba)$_3$ (68.3 mg, 0.075 mmol) and BINAP (93 mg, 0.149 mmol) and the resulting mixture was stirred at 80° C. for 5 hours. The mixture was diluted in EtOAc, washed with saturated aqueous sodium bicarbonate, water and brine, dried over sodium sulfate, filtered and concentrated. The crude product was purified by flash chromatography on silica gel (cyclohexane/EtOAc) to give INT 46.

LC/MS method 4: MS (ESI): 351 [M+H]$^+$, rt=1.31 min.
$^1$H-NMR (CDCl$_3$): δ (ppm) 7.91 (d, 1H), 7.26 (d, 1H), 7.19-7.17 (m, 1H), 7.08 (dd, 1H), 6.32 (d, 1H), 5.93 (s, 1H), 4.83 (d, 1H), 4.43 (q, 1H), 4.01-3.91 (m, 4H), 2.34 (s, 3H), 1.90-1.73 (m, 2H), 0.94 (t, 3H).

3. 2-[(R)-1-(4-Chloro-3-methyl-phenyl)-propylamino]-5-fluoro-pyridine-4-carbaldehyde, INT 46

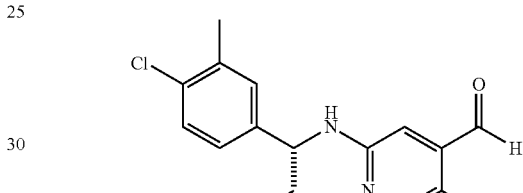

INT 45 (500 mg, 1.43 mmol) was dissolved in THF (20 mL) and HBr (33% in AcOH, 15 eq) was added. The resulting mixture was stirred at 70° C. until completion of the reaction. The mixture was quenched with saturated aqueous sodium bicarbonate and extracted with EtOAc. The organic layer was washed with saturated aqueous sodium bicarbonate, water and brine, dried over sodium sulfate and concentrated. The crude product was purified by flash chromatography on silica gel (cyclohexane/EtOAc) to give INT 46.

LC/MS method 4: MS (ESI): 307 [M+H]$^+$, rt=1.36 min.
$^1$H-NMR (CDCl$_3$): δ (ppm) 10.23 (s, 1H), 8.13 (d, 1H), 7.27 (d, 1H), 7.17 (d, 1H), 7.08 (dd, 1H), 6.53 (d, 1H), 5.00 (d, 1H), 4.44 (q, 1H), 2.35 (s, 3H), 1.89-1.75 (m, 2H), 0.95 (t, 3H).

4. 1-{2-[(R)-1-(4-Chloro-3-methyl-phenyl)-propylamino]-5-fluoro-pyridin-4-ylmethyl}-azetidine-3-carboxylic acid To a solution of INT 46 (288 mg, 0.94 mmol) and azetidine-3-carboxylic acid (114 mg, 1.13 mmol) in MeOH (9 mL) was added AcOH (0.054 mL, 0.989 mmol) followed by PS—CNBH$_3$ (3.5 mmol/g, 540 mg, 1.88 mmol). The reaction mixture was stirred at room temperature for 16 hours. The mixture was filtered through Celite. The filtrate was concentrated and the residue was purified by preparative HPLC (H$_2$O/CH$_3$CN) to give 54.

LC/MS method 2: MS (ESI): 392 [M+H]$^+$, rt=1.80 min.
$^1$H-NMR (DMSO-d$_6$): δ (ppm) 7.72 (s, 1H), 7.28 (d, 1H), 7.27 (s, 1H), 7.15 (d, 1H), 6.93 (d, 1H), 6.49 (d, 1H), 4.62 (q, 1H), 3.37 (m, 2H), 3.22 (m, 2H), 2.27 (s, 3H), 1.73 (m, 1H), 1.64 (m, 1H), 0.84 (t, 3H).

Example 55

(R)-1-{5-Chloro-2-[(R)-1-(4-chloro-3-methyl-phenyl)-propylamino]-pyridin-4-ylmethyl}-pyrrolidine-3-carboxylic acid

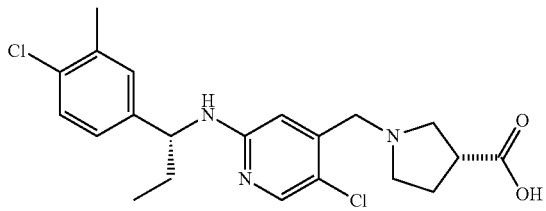

The title compound was prepared following a procedure analogous to Example 54 using 2-bromo-5-chloroisonicotinaldehyde and 1,3-propanediol in step 1 and (R)-pyrrolidine-3-carboxylic acid in step 4.

LC/MS method 2: MS (ESI): 422 [M+H]$^+$, rt=1.96 min.

Example 56

(R)-1-{5-[(R)-1-(4-Chloro-3-methyl-phenyl)-propylamino]-2-methyl-pyridin-3-ylmethyl}-pyrrolidine-3-carboxylic acid

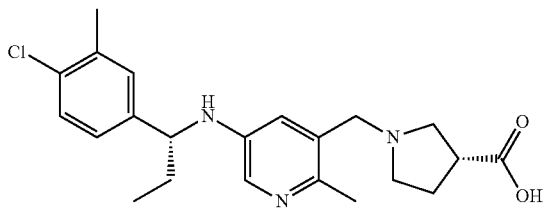 [SMILES: CC[C@@H](Nc1cnc(C)c(CN2CC[C@@H](C(=O)O)C2)c1)c1ccc(Cl)c(C)c1]

1. 5-Bromo-2-chloro-3-dimethoxymethyl-pyridine, INT 47

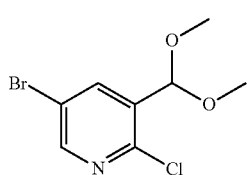

A mixture of 5-bromo-2-chloronicotinaldehyde (981 mg, 2.43 mmol), trimethylorthoformate (1.46 mL, 13.4 mmol) and p-toluenesulfonic acid monohydrate (42.3 mg, 0.222 mmol) in MeOH (18 mL) was refluxed for 16 hours. The mixture was diluted in CH$_2$Cl$_2$ and washed with 10% aqueous potassium carbonate and brine, dried over sodium sulfate, filtered and concentrated. The crude product was used in the next step without further purification.

LC/MS method 2: MS (ESI): 267 [M+H]$^+$, rt=2.23 min. $^1$H-NMR (DMSO-d$_6$): δ (ppm) 8.59 (d, 1H), 8.06 (d, 1H), 5.50 (s, 1H), 3.32 (2d, 6H).

2. (6-Chloro-5-dimethoxymethyl-pyridin-3-yl)-[(R)-1-(4-chloro-3-methyl-phenyl)-propyl]-amine, INT 48

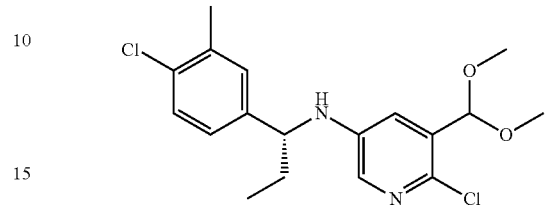

The title compound was prepared by a similar procedure to INT 45 starting from INT 47. LC/MS method 2: MS (ESI): 369 [M+H]$^+$, rt=3.10 min. $^1$H-NMR (DMSO-d$_6$): δ (ppm) 7.59 (d, 1H), 7.32 (m, 2H), 7.32 (s, 1H), 7.18 (dd, 1H), 7.09 (d, 1H), 5.30 (s, 1H), 4.25 (t, 1H), 4.72 (q, 1H), 3.29 (s, 3H), 3.12 (s, 3H), 2.28 (s, 3H), 1.83-1.58 (m, 2H), 0.88 (t, 3H).

3. [(R)-1-(4-Chloro-3-methyl-phenyl)-propyl]-(5-dimethoxymethyl-6-methyl-pyridin-3-yl)-amine, INT 49

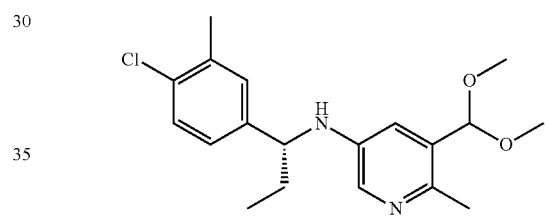

A mixture of INT 48 (250 mg, 0.677 mmol) and Pd(dppf)Cl$_2$·CH$_2$Cl$_2$ (16.6 mg, 0.020 mmol) was dissolved in degassed dioxane (7 mL) and ZnMe$_2$ (2 M in toluene, 1.02 mL, 2.04 mmol) was added. The mixture was stirred in a sealed vessel at 100° C. overnight. After cooling down, the mixture was quenched with a few drops of MeOH and the mixture was diluted with EtOAc, washed with saturated aqueous sodium bicarbonate and brine, dried over sodium sulfate and concentrated. The crude product was purified by flash chromatography (cyclohexane/EtOAc) to give INT 49.

LC/MS method 4: MS (ESI): 349 [M+H]$^+$, rt=1.09 min. $^1$H-NMR (CDCl$_3$): δ (ppm) 7.76 (d, 1H), 7.27 (d, 1H), 7.16 (d, 1H), 7.08-7.02 (m, 1H), 7.00 (d, 1H), 5.30 (s, 1H), 4.18 (q, 1H), 3.96 (d, 1H), 3.32 (s, 3H), 3.14 (s, 3H), 2.38 (s, 3H), 2.33 (s, 3H), 1.90-1.72 (m, 2H), 0.94 (t, 3H).

4. 5-[(R)-1-(4-Chloro-3-methyl-phenyl)-propylamino]-2-methyl-pyridine-3-carbaldehyde, INT 50

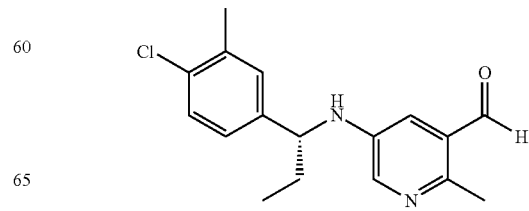

INT 49 (184 mg, 0.527 mmol) was heated at 80° C. in 1 M HCl (2.6 mL) for 2 hours. The mixture was cooled down and diluted with saturated aqueous sodium bicarbonate. The mixture was extracted with EtOAc and the organic layer was washed with brine, dried over sodium sulfate and concentrated. The product was used in the next step without further purification.

LC/MS method 4: MS (ESI): 303 [M+H]$^+$, rt=1.17 min.

5. (R)-1-{5-[(R)-1-(4-Chloro-3-methyl-phenyl)-propylamino]-2-methyl-pyridin-3-ylmethyl}-pyrrolidine-3-carboxylic acid The title compound was prepared from INT 50 by a procedure analogous to step 4 of 54 using (R)-pyrrolidine-3-carboxylic acid.

LC/MS method 2: MS (ESI): 402 [M+H]$^+$, rt=1.41 min.

Example 57

1-{5-Chloro-2-[(R)-1-(4-chloro-3-methyl-phenyl)-propylamino]-pyridin-4-ylmethyl}-3-methyl-pyrrolidine-3-carboxylic acid

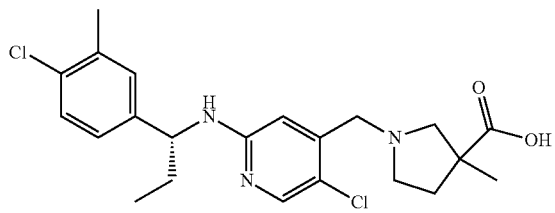 [SMILES: CC[C@@H](Nc1cc(CN2CCC(C)(C(=O)O)C2)c(Cl)cn1)c1ccc(Cl)c(C)c1]

1. 2-Bromo-5-chloro-4-dimethoxymethyl-pyridine, INT 51

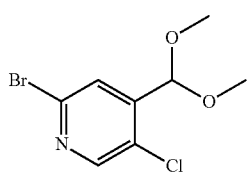

A mixture of 2-bromo-5-chloronicotinaldehyde (3.00 g, 13.6 mmol), trimethylorthoformate (4.48 mL, 40.8 mmol) and p-toluenesulfonic acid monohydrate (129 mg, 0.680 mmol) in MeOH (55 mL) was refluxed for 16 hours. The mixture was diluted in CH$_2$Cl$_2$ and washed with 10% aqueous potassium carbonate and brine, dried over sodium sulfate, filtered and concentrated. The crude product was used in the next step without further purification. LC/MS method 2: MS (ESI): 267 [M+H]$^+$, rt=2.22 min. $^1$H-NMR (DMSO-d$_6$): δ (ppm) 8.53 (s, 1H), 7.65 (S, 1H), 5.53 (s, 1H), 3.31 (2d, 6H).

2. (5-Chloro-4-dimethoxymethyl-pyridin-2-yl)-[(R)-1-(4-chloro-3-methyl-phenyl)-propyl]-amine, INT 52

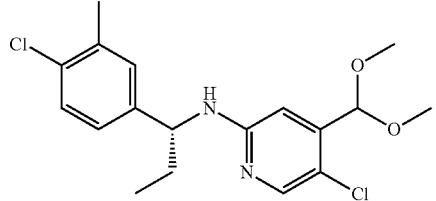 [SMILES: CC[C@@H](Nc1cc(C(OC)OC)c(Cl)cn1)c1ccc(Cl)c(C)c1]

The title compound was prepared by a procedure analogous to INT 45 starting from INT 51.

LC/MS method 2: MS (ESI): 369 [M+H]$^+$, rt=3.07 min. $^1$H-NMR (DMSO-d$_6$): δ (ppm) 7.86 (s, 1H), 7.26 (d, 1H), 7.30 (m, 2H), 7.28 (s, 1H), 7.14 (d, 1H), 6.74 (s, 1H), 5.32 (s, 1H), 4.72 (q, 1H), 3.28 (s, 3H), 3.24 (s, 3H), 2.27 (s, 3H), 1.75-1.62 (m, 2H), 0.84 (t, 3H).

3. 5-[(R)-1-(4-Chloro-3-methyl-phenyl)-propylamino]-2-methyl-pyridine-3-carbaldehyde, INT 53

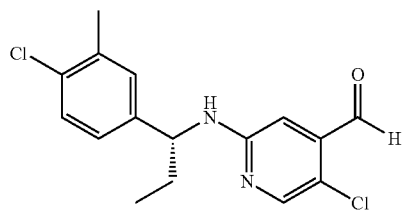

INT 52 (200 mg, 0.542 mmol) was heated at 80° C. in 1 M HCl (2.7 mL) for 2 hours. The mixture was cooled down and diluted with saturated aqueous sodium bicarbonate. The mixture was extracted with EtOAc and the organic layer was washed with brine, dried over sodium sulfate and concentrated. The product was used in the next step without further purification.

LC/MS method 2: MS (ESI): 323 [M+H]$^+$, rt=3.07 min.

4. 1-{5-Chloro-2-[(R)-1-(4-chloro-3-methyl-phenyl)-propylamino]-pyridin-4-ylmethyl}-3-methyl-pyrrolidine-3-carboxylic acid To a solution of INT 53 (263 mg, 0.814 mmol) and 3-methyl-pyrrolidine-3-carboxylic acid (105 mg, 0.814 mmol) in MeOH (7 mL) was added AcOH (48.9 mg, 0.814 mmol) followed by PS—CNBH$_3$ (3.5 mmol/g, 462 mg, 1.62 mmol). The reaction mixture was stirred at room temperature for 16 hours. The mixture was filtered through Celite. The filtrate was concentrated and the residue was purified by preparative HPLC (H$_2$O/CH$_3$CN) to give 57.

LC/MS method 2: MS (ESI): 436 [M+H]$^+$, rt=2.13 min. $^1$H-NMR (DMSO-d$_6$): δ (ppm) 12.35 (br s, 1H), 7.81 (2s, 1H), 7.30 (d, 1H), 7.29 (dd, 1H), 7.29 (d, 1H), 7.16 (m, 1H), 7.14 (m, 1H), 6.61 (2s, 1H), 4.63 (m, 1H), 3.48 (d, 1H), 2.91 (dd, 1H), 2.59-2.39 (m, 2H), 2.36-2.22 (m, 2H), 2.27 (s, 3H), 1.79-1.70 (m, 1H), 1.70-1.62 (m, 1H), 1.57-1.50 (m, 1H), 1.26 (2s, 3H), 0.85 (t, 3H).

Example 58

3-({5-Chloro-2-[(R)-1-(4-chloro-3-methyl-phenyl)-propylamino]-pyridin-4-ylmethyl}-amino)-propionic acid

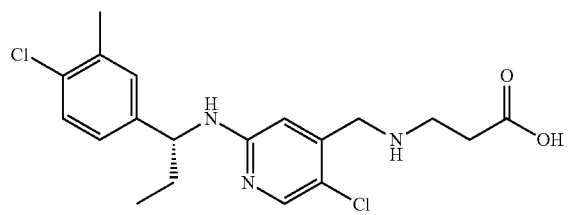 [SMILES: CC[C@@H](Nc1cc(CNCCC(=O)O)c(Cl)cn1)c1ccc(Cl)c(C)c1]

The title compound was prepared by a procedure analogous to Example 57 using 3-amino-propionic acid tert-butyl ester hydrochloride in step 4 and with an additional HCl-induced deprotection step.

LC/MS method 2: MS (ESI): 396 [M+H]$^+$, rt=1.94 min. $^1$H-NMR (DMSO-d$_6$): δ (ppm) 9.16 (br s, 2H), 7.97 (s, 1H), 7.52 (d, 1H), 7.31 (s, 1H), 7.30 (d, 1H), 7.17 (dd, 1H), 6.70 (s, 1H), 4.73 (m, 1H), 4.12 (t, 2H), 3.20 (m, 2H), 2.71 (t, 2H), 2.28 (s, 3H), 1.81-1.65 (m, 2H), 0.86 (t, 3H).

Example 59

(R)-1-{5-Chloro-2-[(R)-1-(4-chloro-3,5-dimethyl-phenyl)-propylamino]-pyridin-4-ylmethyl}-pyrrolidine-3-carboxylic acid

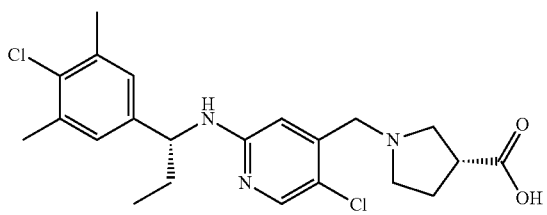 [SMILES: CC[C@@H](Nc1cc(CN2CC[C@@H](C(=O)O)C2)c(Cl)cn1)c1cc(C)c(Cl)c(C)c1]

The title compound was prepared by a procedure analogous to Example 57 using INT 38 in step 2 and (R)-pyrrolidine-3-carboxylic acid in step 4.

LC/MS method 2: MS (ESI): 436 [M+H]$^+$, rt=2.13 min.

Example 60

(R)-1-{2-[(R)-1-(4-Chloro-3-methyl-phenyl)-propylamino]-5-methyl-pyridin-4-ylmethyl}-pyrrolidine-3-carboxylic acid

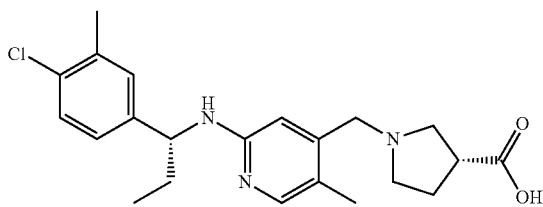 [SMILES: CC[C@@H](Nc1cc(CN2CC[C@@H](C(=O)O)C2)c(C)cn1)c1ccc(Cl)c(C)c1]

1. (5-Chloro-4-dimethoxymethyl-pyridin-2-yl)-[(R)-1-(4-chloro-3-methyl-phenyl)-propyl]-amine, INT 54

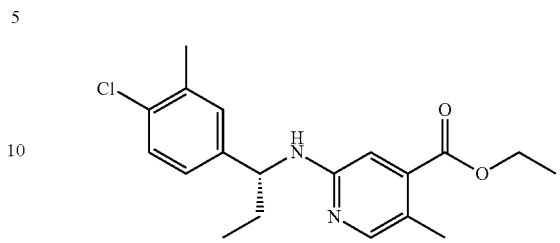

To a solution of 2-chloro-5-methylpyridine-4-carboxylic acid ethyl ester (750 mg, 3.76 mmol), (R)-1-(4-chloro-3-methyl-phenyl)-propylamine hydrochloride (992 mg, 4.51 mmol) and sodium tert-butoxide (867 mg, 9.02 mmol) in degassed toluene (54 mL) was added Pd$_2$(dba)$_3$ (172 mg, 0.188 mmol) and BINAP (234 mg, 0.378 mmol) and the resulting mixture was stirred at 50° C. for 5 hours. The mixture was diluted with EtOAc, washed with saturated aqueous sodium bicarbonate, water and brine, dried over sodium sulfate, filtered and concentrated. The crude product was purified by flash chromatography on silica gel (cyclohexane/EtOAc) to give INT 54.

LC/MS method 4: MS (ESI): 347 [M+H]$^+$, rt=1.36 min. $^1$H-NMR (CDCl$_3$): δ (ppm) 7.96 (s, 1H), 7.26 (d, 1H), 7.19 (d, 1H), 7.09 (dd, 1H), 6.67 (s, 1H), 4.85 (t, 1H), 4.46 (q, 1H), 2.34 (5, 3H), 2.32 (s, 3H), 1.91-1.75 (m, 2H), 1.34 (t, 3H), 0.95 (t, 3H).

2. 5-[(R)-1-(4-Chloro-3-methyl-phenyl)-propylamino]-2-methyl-pyridine-3-carbaldehyde, INT 55

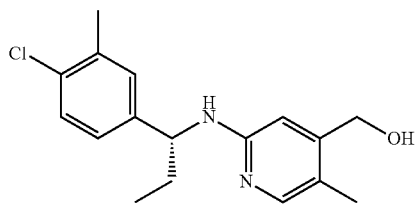 [SMILES: CC[C@@H](Nc1cc(CO)c(C)cn1)c1ccc(Cl)c(C)c1]

INT 54 (380 mg, 1.096 mmol) was dissolved in THF and cooled to 0° C. LiAlH$_4$ (1 M in THF, 3.29 mL, 3.29 mmol) was added dropwise and the mixture was stirred at the same temperature for 1 hour. The mixture was quenched with water and 1 M NaOH. The mixture was extracted with EtOAc, washed with saturated aqueous sodium bicarbonate and brine, dried over sodium sulfate, filtered and concentrated. The product was used in the next step without further purification.

LC/MS method 2: MS (ESI): 305 [M+H]$^+$, rt=1.69 min. $^1$H-NMR (DMSO-d$_6$): δ (ppm) 7.55 (s, 1H), 7.30 (d, 1H), 7.28 (d, 1H), 7.15 (dd, 1H), 6.71 (d, 1H), 6.61 (s, 1H), 4.72 (q, 1H), 4.32 (s, 2H), 2.28 (s, 3H), 1.92 (s, 3H), 1.74-1.62 (m, 2H), 0.86 (t, 3H).

3. 2-[(R)-1-(4-Chloro-3-methyl-phenyl)-propylamino]-5-methyl-pyridine-4-carbaldehyde, INT 56

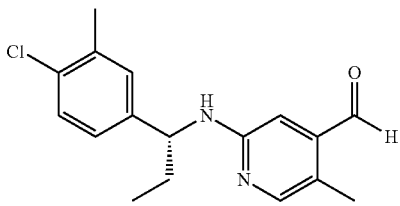 [SMILES: CC[C@@H](Nc1cc(C=O)c(C)cn1)c1ccc(Cl)c(C)c1]

Oxalyl chloride (0.232 mL, 2.70 mmol) was dissolved in CH$_2$Cl$_2$ (15 mL) and the solution was cooled to −78° C. A solution of DMSO (0.383 mL, 5.40 mmol) in CH$_2$Cl$_2$ (3 mL) was added dropwise and the mixture was stirred for 10 minutes at this temperature. Then, a solution of INT 55 (329 mg, 1.079 mmol) in CH$_2$Cl$_2$ (3 mL) was added dropwise and the mixture was stirred for 1 hour at this temperature. NEt$_3$ (0.932 mL, 6.69 mmol) was added and the mixture was stirred further at −78° C. for 1 hour and the mixture was quenched with water. The mixture was poured onto 10% aqueous KHSO$_4$ and extracted with EtOAc. The organic layer was washed with saturated aqueous sodium bicarbonate solution and brine, dried over sodium sulfate, filtered and concentrated. The product was used in the next step without further purification.

LC/MS method 4: MS (ESI): 303 [M+H]$^+$, rt=1.26 min.

4. (R)-1-{2-[(R)-1-(4-Chloro-3-methyl-phenyl)-propylamino]-5-methyl-pyridin-4-ylmethyl}-pyrrolidine-3-carboxylic acid The title compound was prepared following a procedure analogous to step 4 of Example 54 using INT 56 and (R)-pyrrolidine-3-carboxylic acid.

LC/MS method 2: MS (ESI): 402 [M+H]$^+$, rt=1.48 min.

Alternatively, agents of the invention may be prepared by a reaction sequence involving either reductive amination of an appropriate halo-benzaldehyde or halo-pyridyl-carbaldehyde with an appropriate amino ester or Lewis acid catalyzed Michael addition of an appropriate benzylamine with an appropriate aβ-unsaturated ester followed by Buchwald coupling with an appropriate amine and an optional deprotection step as shown in Scheme 4 below:

Scheme 4:

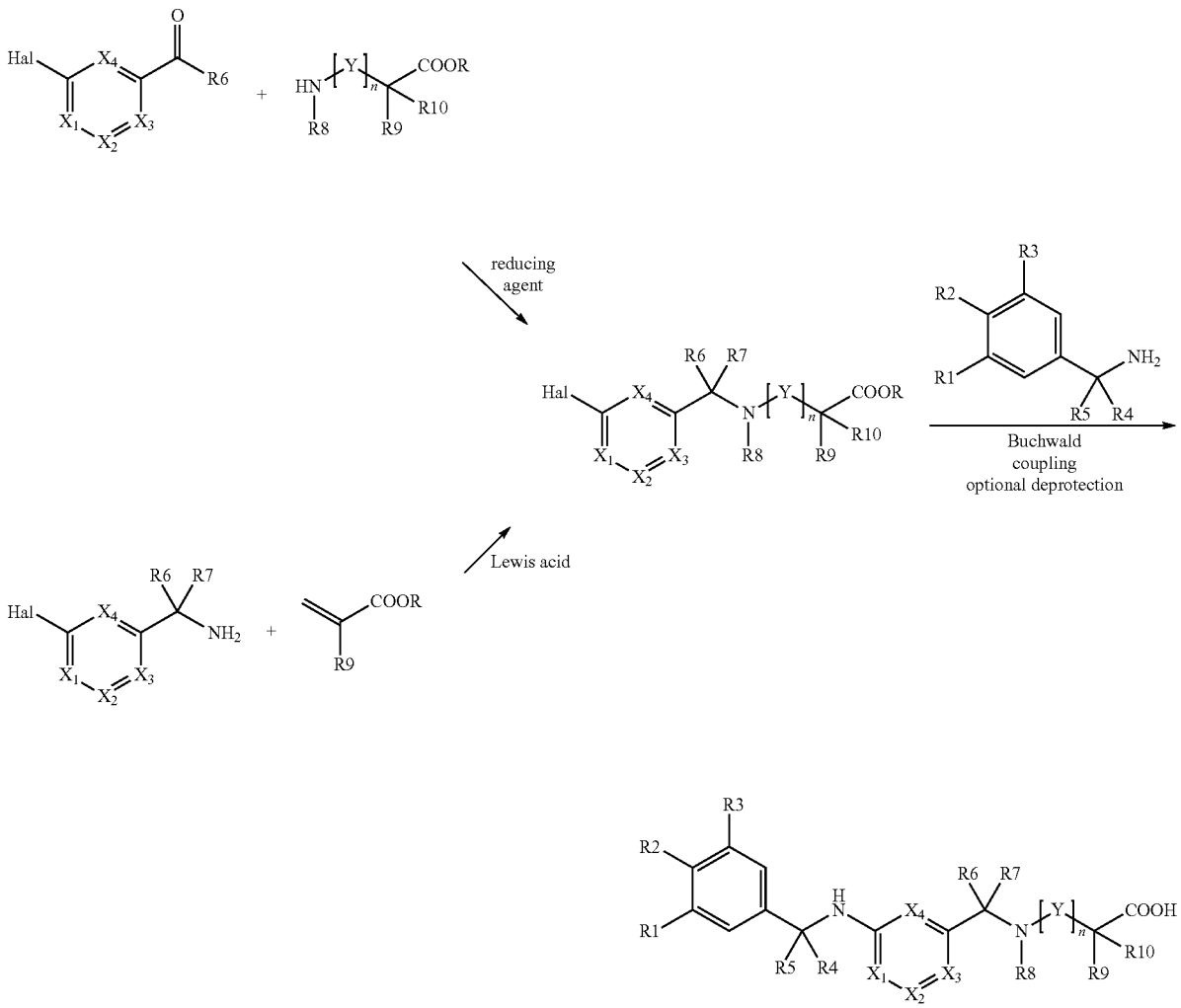

The following compounds were made in accordance to the above indicated reaction Scheme 4:

Example 61

1-{2-Chloro-5-[(R)-1-(4-chloro-3,5-dimethyl-phenyl)-propylamino]-benzyl}-azetidine-3-carboxylic acid

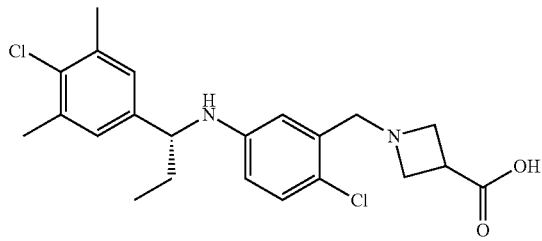 [SMILES: CC[C@@H](Nc1ccc(Cl)c(CN2CC(C(=O)O)C2)c1)c1cc(C)c(Cl)c(C)c1]

1. 1-(5-Bromo-2-chloro-benzyl)azetidine-3-carboxylic acid tert-butyl ester, INT 57

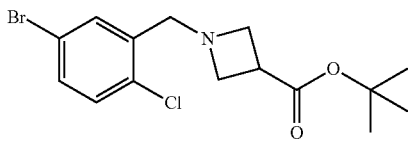 [SMILES: CC(C)(C)OC(=O)C1CN(Cc2cc(Br)ccc2Cl)C1]

A mixture of 5-bromo-2-chloro-benzaldehyde (2 g, 9.11 mmol) and azetidine-3-carboxylic acid tert-butyl ester hydrochloride (1.765 g, 9.11 mmol) in dichloroethane (50 mL) was stirred at room temperature for 10 minutes. To this mixture was added sodium triacetoxy-borohydride (3.86 g, 18.23 mmol) in 3 portions over a period of 10 minutes and the cloudy mixture was stirred overnight. The reaction mixture was diluted with $CH_2Cl_2$ (100 mL) and washed twice with 10% sodium bicarbonate solution, twice with water then brine. The organic layer was dried over sodium sulfate, filtered and concentrated. The crude was purified by chromatography on silica gel (cyclohexane/EtOAc).

MS (ESI): 360 [M+H]$^+$, UPLC: rt=1.17 min. $^1$H-NMR (CDCl$_3$): δ (ppm) 7.55 (s, 1H), 7.29 (d, 1H), 7.18 (d, 1H), 3.68 (s, 2H), 3.61 (t, 2H), 3.35 (t, 2H), 3.28 (m, 1H), 1.46 (s, 9H).

2. 1-{2-Chloro-5-[(R)-1-(4-chloro-3,5-dimethyl-phenyl)-propylamino]-benzyl}-azetidine-3-carboxylic acid tert-butyl ester, INT 58

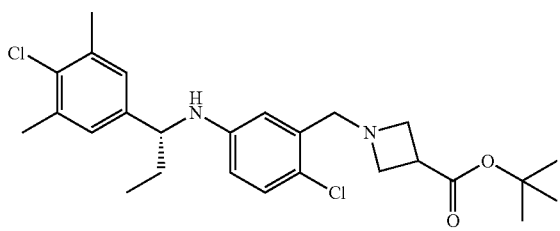 [SMILES: CC[C@@H](Nc1ccc(Cl)c(CN2CC(C(=O)OC(C)(C)C)C2)c1)c1cc(C)c(Cl)c(C)c1]

A mixture of INT 57 (250 mg, 0.693 mmol), amine INT 38 (137 mg, 0.693 mmol) and cesium carbonate (678 mg, 2.079 mmol) in toluene (4.5 mL) and tert-butanol (1.8 mL) was purged with argon for 10 minutes. Then, XPhos (66.1 mg, 0.139 mmol) and palladium acetate (15.56 mg, 0.069 mmol) were added, the vial was closed and heated at 100° C. for 3 hours. The reaction mixture was then diluted with EtOAc (35 mL) and washed with water and brine. The organic layer was dried over sodium sulfate, filtered and concentrated.

The crude was purified by chromatography on silica gel (cyclohexane/EtOAc).

LC/MS method 2: MS (ESI): 477 [M+H]$^+$, rt=2.91 min. $^1$H-NMR (DMSO-d$_6$): δ (ppm) 7.14 (s, 2H), 6.94 (d, 1H), 6.52 (s, 1H), 6.37 (d, 1H), 6.25 (d, 1H), 4.08 (m, 1H), 3.39 (s, 2H), 3.29 (overlapping m, 1H), 3.1-3.25 (m, 3H), 2.98 (m, 1H), 2.27 (s, 6H), 1.74 (m, 1H), 1.62 (m, 1H), 1.40 (s, 9H), 0.86 (t, 3H).

3. 1-{2-Chloro-5-[(R)-1-(4-chloro-3,5-dimethyl-phenyl)-propylamino]-benzyl}-azetidine-3-carboxylic acid A solution of INT 58 (206 mg, 0.431 mmol) in $CH_2Cl_2$ (5 mL) was treated with HCl (4 M in dioxane, 0.43 mL, 1.726 mmol) and stirred at room temperature overnight. The mixture contained some starting material, so another portion of HCl (4 M in dioxane, 0.50 ml, 2.00 mmol) was added and stirring continued for 4 hours. Excess of HCl gas was removed by a stream of argon. The mixture was neutralized with 10% sodium bicarbonate solution then treated with 10% ammonium chloride solution and extracted first with $CH_2Cl_2$ then with EtOAc. The combined organic layers were dried over sodium sulfate, filtered and concentrated. The title compound was purified by preparative UPLC (H$_2$O/CH$_3$CN).

LC/MS method 2: MS (ESI): 421 [M+H]$^+$, rt=2.25 min. $^1$H-NMR (DMSO-d$_6$): δ (ppm) 7.13 (s, 2H), 6.94 (d, 1H), 6.56 (s, 1H), 6.35 (d, 1H), 6.27 (d, 1H), 4.08 (m, 1H), 3.41 (s, 2H), 3.05-3.4 (overlapping m, 5H), 2.26 (s, 6H), 1.75 (m, 1H), 1.63 (m, 1H), 0.86 (t, 3H).

Example 62

1-{2-Chloro-5-[(R)-1-(4-chloro-3-methyl-phenyl)-propylamino]-benzyl}-azetidine-3-carboxylic acid

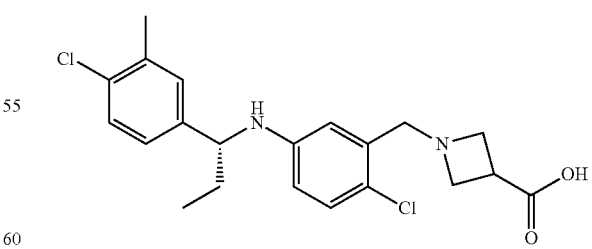

The title compound was prepared according to Scheme 4 following a procedure analogous to Example 61 using (R)-1-(4-chloro-3-methyl-phenyl)propylamine hydrochloride in step 2.

LC/MS method 2: MS (ESI): 407 [M+H]$^+$, rt=2.10 min.

Example 63

1-{2-Chloro-5-[(R)-1-(4-chloro-3-methyl-phenyl)-2-methyl-propylamino]-benzyl}-azetidine-3-carboxylic acid

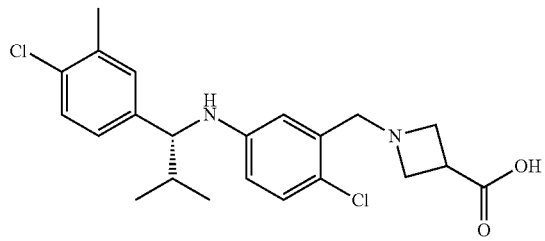 [SMILES: Cc1cc([C@H](Nc2ccc(Cl)c(CN3CC(C(=O)O)C3)c2)C(C)C)ccc1Cl]

The title compound was prepared according to Scheme 4 following a procedure analogous to Example 61 using amine INT 60 (synthesis below) in step 2.

LC/MS method 2: MS (ESI): 421 [M+H]$^+$, rt=2.24 min.

1. (S)-2-Methyl-propane-2-sulfinic acid [(R)-1-(4-chloro-3-methyl-phenyl)-2-methyl-propyl]-amide, INT 59

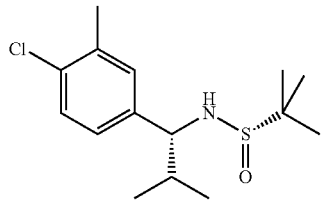 [SMILES: Cc1cc([C@H](N[S@@](=O)C(C)(C)C)C(C)C)ccc1Cl]

A solution of the imine INT 65 (1.33 g, 5.16 mmol) in CH$_2$Cl$_2$ (30 mL) was cooled to −50° C. To this solution was added isopropylmagnesium bromide (2 M in THF, 5.16 mL, 10.32 mmol) at a rate that the temperature did not exceed −48° C. and stirring at this temperature was continued for 1 hour. The cooling bath was removed and the reaction mixture was allowed to warm up to room temperature overnight. It was quenched with saturated ammonium chloride solution and extracted with EtOAc. The organic layer was washed with water and brine, dried over sodium sulfate, filtered and concentrated. The crude mixture of diastereomers was purified by chromatography on silica gel (cyclohexane/EtOAc). The (S,S)-isomer eluted first, followed by the desired (S,R)-isomer.

MS (ESI): 302 [M+H]$^+$, $^1$H-NMR (CDCl$_3$): δ (ppm) 7.28 (d, 1H), 7.03 (s, 1H), 7.01 (d, 1H), 4.09 (br d, 1H), 3.45 (br s, 1H), 2.36 (5, 3H), 1.94 (m, 1H), 1.19 (s, 9H), 0.98 (d, 3H), 0.80 (d, 3H).

2. (R)-1-(4-Chloro-3-methyl-phenyl)-2-methyl-propylamine, INT 60

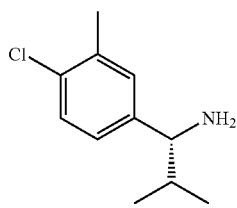

A solution of intermediate INT 59 (330 mg, 1.09 mmol) in MeOH (8 mL) was treated with HCl (4 M in dioxane, 0.55 mL, 2.2 mmol) and stirred overnight. After evaporation of the solvents, a solid was obtained. The solid was then dissolved in 2 M HCl (30 mL) and washed with EtOAc. The aqueous layer was separated and the pH adjusted to about 11 using 2 M NaOH followed by extraction with CH$_2$Cl$_2$ (3×). The organic extracts were combined, dried over sodium sulfate, filtered and concentrated.

UPLC: rt=0.93 min. $^1$H-NMR (CDCl$_3$): δ (ppm) 7.27 (d, 1H), 7.18 (s, 1H), 7.07 (d, 1H), 3.60 (d, 1H), 3.07 (v br s, 2H), 2.36 (s, 3H), 1.90 (m, 1H), 0.98 (d, 3H), 0.77 (d, 3H).

Example 64

1-{2-Chloro-5-[(R)-1-(4-chloro-3,5-dimethyl-phenyl)-2-methyl-propylamino]-benzyl}-azetidine-3-carboxylic acid

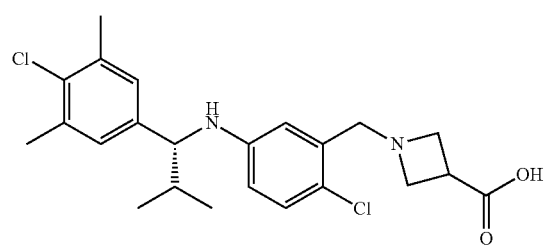 [SMILES: Cc1cc([C@H](Nc2ccc(Cl)c(CN3CC(C(=O)O)C3)c2)C(C)C)cc(C)c1Cl]

The title compound was prepared according to Scheme 4 following a procedure analogous to Example 61 using amine INT 62 (synthesis below) in step 2.

LC/MS method 2: MS (ESI): 435 [M+H]$^+$, rt=2.41 min.

1. (R)-2-Methyl-propane-2-sulfinic acid [(R)-1-(4-chloro-3,5-dimethyl-phenyl)-2-methyl-propyl]-amide, INT 61

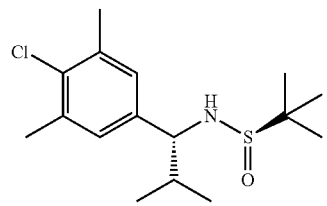 [SMILES: Cc1cc([C@H](N[S@](=O)C(C)(C)C)C(C)C)cc(C)c1Cl]

To a solution of dimethylzinc (1.7 M in toluene, 20.69 mL, 41.4 mmol) was added dropwise a solution of isopropylmagnesium chloride (2 M in THF, 18.4 mL, 36.8 mmol) at room temperature and the mixture was stirred for 1 hour.

In a separate flask a solution of imine INT 36 (5 g, 18.4 mmol) in THF (140 mL) was cooled in a dry ice bath under argon to −78° C. At this temperature the organozincate solution from above was added dropwise over a period of about 30 minutes. Stirring was continued for another hour before the resulting mixture was first quenched carefully with 10% ammonium chloride solution (40 mL), then water (50 mL). The reaction mixture was allowed to warm up to room temperature and was then extracted with Et$_2$O (3×). The organic layers were washed with water and brine, dried over sodium sulfate, filtered and concentrated. The crude was purified by chromatography on silica gel (cyclohexane/EtOAc).

UPLC: rt=2.28 min.

2. (R)-1-(4-Chloro-3,5-dimethyl-phenyl)-2-methyl-propylamine hydrochloride, INT 62

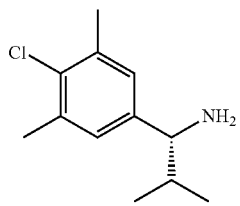

A solution of intermediate INT 61 (4.53 g, 14.34 mmol) in MeOH (75 mL) was treated with HCl (4 M in dioxane, 7.17 mL, 28.7 mmol) and stirred overnight. After evaporation of the solvents, a solid was obtained which was washed with Et$_2$O. The solid was then dissolved in 10% sodium carbonate solution and extracted twice with EtOAc. The combined organic layers were dried over sodium sulfate, filtered and concentrated. The crude amine was dissolved in Et$_2$O and treated with an excess of an ethereal solution of HCl (2 M). The suspension was concentrated to yield the title compound.

UPLC: rt=1.05 min. $^1$H-NMR (CDCl$_3$): δ (ppm) 7.02 (s, 2H), 3.54 (d, 1H), 2.76 (v br s, 3H) 2.36 (s, 6H), 1.87 (m, 1H), 0.97 (d, 3H), 0.77 (d, 3H).

Example 65

1-{2-Chloro-5-[(S)-1-(4-chloro-3-methyl-phenyl)-2,2,2-trifluoro-ethylamino]-benzyl}-3-methyl-azetidine-3-carboxylic acid

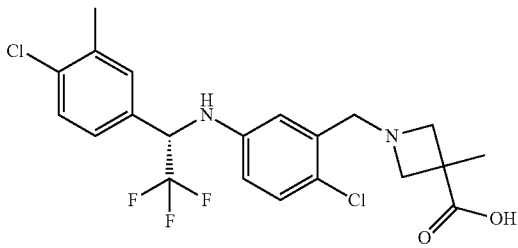 [SMILES: Cc1cc([C@H](Nc2ccc(Cl)c(CN3CC(C)(C(=O)O)C3)c2)C(F)(F)F)ccc1Cl]

The title compound was prepared according to Scheme 4 following a procedure analogous to Example 61 using 3-methyl-azetidine-3-carboxylic acid methyl ester hydrochloride (INT 14) in step 1 and (S)-1-(4-chloro-3-methyl-phenyl)-2,2,2-trifluoro-ethylamine hydrochloride in step 2, followed by a LiOH-mediated ester cleavage.

LC/MS method 2: MS (ESI): 461 [M+H]$^+$, rt=2.09 min.

Example 66

1-{2-Chloro-5-[(R)-1-(4-chloro-3,5-dimethyl-phenyl)-propylamino]-benzyl}-3-methyl-azetidine-3-carboxylic acid

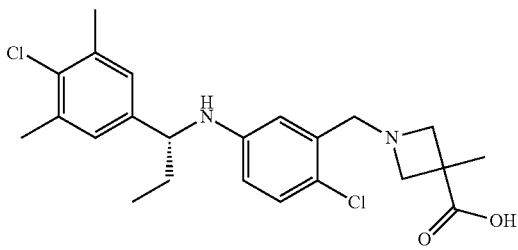 [SMILES: CC[C@@H](Nc1ccc(Cl)c(CN2CC(C)(C(=O)O)C2)c1)c1cc(C)c(Cl)c(C)c1]

The title compound was prepared according to Scheme 4 following a procedure analogous to Example 61 using 3-methyl-azetidine-3-carboxylic acid methyl ester hydrochloride (INT 14) in step 1 and INT 38 in step 2, followed by a LiOH-mediated ester cleavage.

LC/MS method 2: MS (ESI): 435 [M+H]$^+$, rt=2.29 min.

Example 67

1-{3-[(S)-1-(4-Chloro-3-methyl-phenyl)-2,2,2-trifluoro-ethylamino]-benzyl}-azetidine-3-carboxylic acid

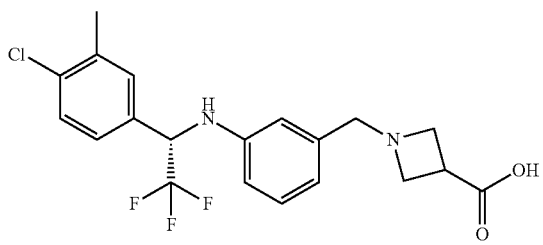 [SMILES: Cc1cc([C@H](Nc2cccc(CN3CC(C(=O)O)C3)c2)C(F)(F)F)ccc1Cl]

The title compound was prepared according to Scheme 4 following a procedure analogous to Example 61 using 3-bromobenzaldehyde in step 1 and (S)-1-(4-chloro-3-methyl-phenyl)-2,2,2-trifluoro-ethylamine hydrochloride in step 2.

LC/MS method 2: MS (ESI): 413 [M+H]$^+$, rt=2.11 min.

Example 68

1-{3-[(S)-1-(4-Chloro-3-methyl-phenyl)-2,2,2-trifluoro-ethylamino]-benzyl}-azetidine-3-carboxylic acid

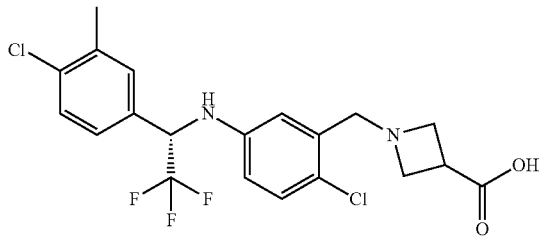 [SMILES: Cc1cc([C@H](Nc2ccc(Cl)c(CN3CC(C(=O)O)C3)c2)C(F)(F)F)ccc1Cl]

The title compound was prepared according to Scheme 4 following a procedure analogous to Example 61 using (S)-1-(4-chloro-3-methyl-phenyl)-2,2,2-trifluoro-ethylamine hydrochloride in step 2.

LC/MS method 2: MS (ESI): 447 [M+H]$^+$, rt=2.03 min.

Example 69

1-{5-[(S)-1-(4-Chloro-3-methyl-phenyl)-2,2,2-trifluoro-ethylamino]-2-trifluoromethyl-benzyl}-azetidine-3-carboxylic acid

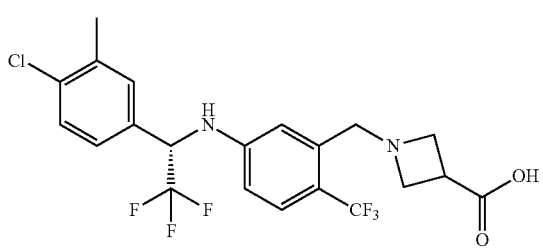

The title compound was prepared according to Scheme 4 following a procedure analogous to Example 61 using 5-chloro-2-trifluoromethyl-benzaldehyde in step 1 and (S)-1-(4-chloro-3-methyl-phenyl)-2,2,2-trifluoro-ethylamine hydrochloride in step 2.

LC/MS method 2: MS (ESI): 481 [M+H]$^+$, rt=2.21 min.

Example 70

1-{5-[(S)-1-(4-Chloro-3-methyl-phenyl)-2,2,2-trifluoro-ethylamino]-2-methyl-benzyl}-azetidine-3-carboxylic acid

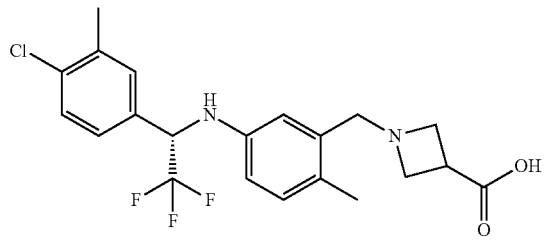 [SMILES: Cc1cc([C@H](Nc2ccc(C)c(CN3CC(C(=O)O)C3)c2)C(F)(F)F)ccc1Cl]

The title compound was prepared according to Scheme 4 following a procedure analogous to Example 61 using 5-bromo-2-methyl-benzaldehyde (INT 30) in step 1 and (S)-1-(4-chloro-3-methyl-phenyl)-2,2,2-trifluoro-ethylamine hydrochloride in step 2.

LC/MS method 2: MS (ESI): 427 [M+H]$^+$, rt=2.01 min.

Example 71

1-{5-[(S)-1-(4-Chloro-3-methyl-phenyl)-2,2,2-trifluoro-ethylamino]-2-fluoro-benzyl}-azetidine-3-carboxylic acid

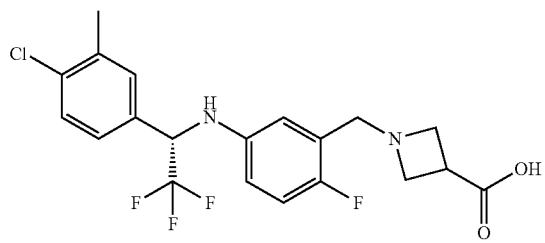 [SMILES: Cc1cc([C@H](Nc2ccc(F)c(CN3CC(C(=O)O)C3)c2)C(F)(F)F)ccc1Cl]

The title compound was prepared according to Scheme 4 following a procedure analogous to Example 61 using 5-bromo-2-fluoro-benzaldehyde in step 1 and (S)-1-(4-chloro-3-methyl-phenyl)-2,2,2-trifluoro-ethylamine hydrochloride in step 2.

LC/MS method 2: MS (ESI): 427 [M+H]$^+$, rt=2.01 min.

Example 72

1-{2-Chloro-5-[(S)-1-(4-chloro-3-methyl-phenyl)-2,2,2-trifluoro-ethylamino]-benzyl}-pyrrolidine-3-carboxylic acid

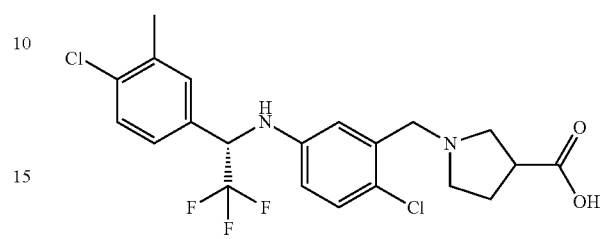

The title compound was prepared according to Scheme 4 following a procedure analogous to Example 61 using pyrrolidine-3-carboxylic acid ethyl ester in step 1 and (S)-1-(4-chloro-3-methyl-phenyl)-2,2,2-trifluoro-ethylamine hydrochloride in step 2, followed by a LiOH-mediated ester cleavage.

LC/MS method 2: MS (ESI): 461 [M+H]$^+$, rt=2.08 min.

Example 73

3-((S)-1-{3-[(S)-1-(4-Chloro-3-methyl-phenyl)-2,2,2-trifluoro-ethylamino]-phenyl}-ethylamino)-propionic acid

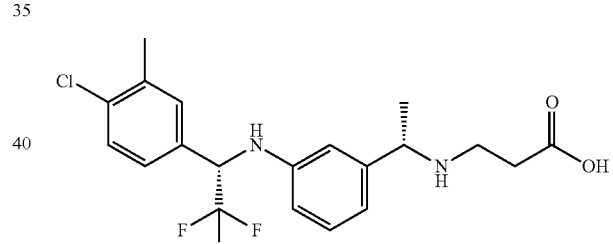

The title compound was prepared according to Scheme 4 following a procedure analogous to steps 2 and 3 of Example 61 using INT 63 (synthesis below) and (S)-1-(4-chloro-3-methyl-phenyl)-2,2,2-trifluoro-ethylamine hydrochloride in step 2 followed by a TFA-mediated ester cleavage.

1. 3-[(S)-1-(3-Bromo-phenyl)-ethylamino]-propionic acid tert-butyl ester, INT 63

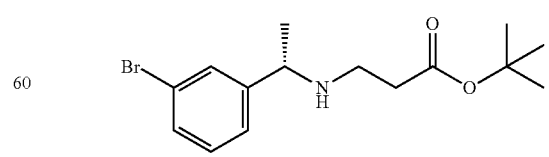

A solution of (S)-1-(3-bromo-phenyl)-ethylamine (0.3 g, 1.5 mmol) and acrylic acid tert-butyl ester (0.19 g, 1.50 mmol) in ethanol (1.3 mL) was stirred at 55° C. for 2.5 hours.

The solvent was concentrated and the crude residue was purified by chromatography on silica gel (heptane/EtOAc).

LC/MS method 2: MS (ESI): 415 [M+H]$^+$, rt=5.87 min. UPLC: rt=1.14 min. $^1$H-NMR (DMSO-d$_6$): δ (ppm) 7.53 (s, 1H), 7.40 (d, 1H), 7.32 (d, 1H), 3.68 (q, 1H), 2.34-2.08 m (4H), 1.21 (d, 3H).

Example 74

1-{6-[(R)-1-(4-Chloro-3-methyl-phenyl)-propylamino]-pyridin-2-ylmethyl}-azetidine-3-carboxylic acid

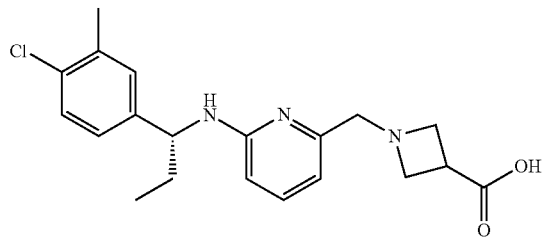 [SMILES: CC[C@@H](Nc1cccc(CN2CC(C(=O)O)C2)n1)c1ccc(Cl)c(C)c1]

1. 1-(5-Bromo-2-chloro-benzyl)-azetidine-3-carboxylic acid tert-butyl ester, INT 64

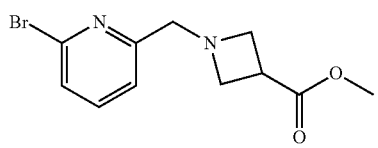 [SMILES: COC(=O)C1CN(Cc2cccc(Br)n2)C1]

To a mixture of 6-bromopyridine-2-carbaldehyde (368 mg, 1.98 mmol) and azetidine-3-carboxylic acid methyl ester hydrochloride (300 mg, 1.98 mmol) in MeOH (10 mL) was added AcOH (0.113 mL, 1.98 mmol) followed by PS—CNBH$_3$ (3.5 mmol/g, 1.13 g, 3.96 mmol). The reaction mixture was stirred at room temperature for 48 hours. The mixture was filtered through Celite. The filtrate was concentrated and purified by chromatography on silica gel (cyclohexane/EtOAc) to give INT 64.

LC/MS method 2: MS (ESI): 285 [M+H]$^+$, rt=0.77 min. $^1$H-NMR (DMSO-d$_6$): δ (ppm) 7.70 (t, 1H), 7.49 (d, 1H), 7.35 (d, 1H), 3.62 (5, 3H), 3.62 (s, 2H), 3.46 (t, 2H), 3.34-3.28 (m, 3H).

2. 1-(6-[(R)-1-(4-Chloro-3-methyl-phenyl)-propylamino]-pyridin-2-ylmethyl)-azetidine-3-carboxylic acid To a solution of INT 64 (300 mg, 1.052 mmol), (R)-1-(4-chloro-3-methyl-phenyl)-propylamine (232 mg, 1.263 mmol) and sodium tert-butoxide (243 mg, 2.53 mmol) in degassed toluene (5 mL) were added Pd$_2$(dba)$_3$ (19.27 mg, 0.021 mmol) and BINAP (26.2 mg, 0.042 mmol) and the resulting mixture was stirred at 70° C. for 16 hours. Another portion of Pd$_2$(dba)$_3$ (19.27 mg, 0.021 mmol) and BINAP (26.2 mg, 0.042 mmol) were added and the mixture was further stirred at 70° C. overnight. After cooling down, EtOH (2 mL) and water (5 mL) were then added, followed by LiOH (25.2 mg, 1.052 mmol) and the mixture was stirred at room temperature for 30 min. The pH was set to 5-6 and the mixture was extracted with CH$_2$Cl$_2$. The organic layer was dried over sodium sulfate, filtered and concentrated. The crude product was purified by flash chromatography (Reverse phase C18, H$_2$O/CH$_3$CN) to give 74.

LC/MS method 2: MS (ESI): 374 [M+H]$^+$, rt=1.85 min. $^1$H-NMR (DMSO-d$_6$): δ (ppm) 7.31 (s, 1H), 7.28 (d, 1H), 7.24 (d, 1H), 7.17 (d, 1H), 6.86 (d, 1H), 6.34 (d, 1H), 6.28 (d, 1H), 4.65 (q, 1H), 3.44-3.30 (m, 4H), 3.24-3.10 (m, 3H), 2.27 (s, 3H), 1.80-1.71 (m, 1H), 1.70-1.61 (m, 1H), 0.84 (t, 3H).

Example 75

1-{2-[(R)-1-(4-Chloro-3-methyl-phenyl)-propylamino]-pyridin-4-ylmethyl}-azetidine-3-carboxylic acid

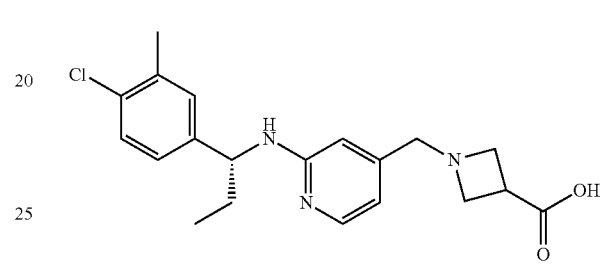

The title compound was prepared following a procedure analogous to Example 74 using 2-bromoisonicotinaldehyde in step 1.

LC/MS method 2: MS (ESI): 374 [M+H]$^+$, rt=1.41 min.

Example 76

1-(3-{[(R)-(4-Chloro-3-methyl-phenyl)-cyclobutyl-methyl]-amino}-benzyl)-azetidine-3-carboxylic acid

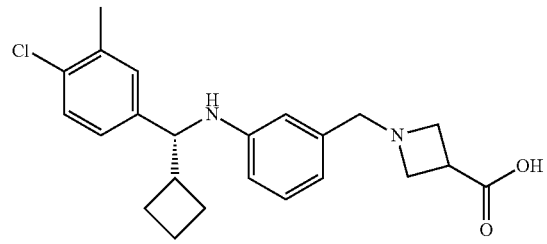 [SMILES: Cc1cc([C@H](Nc2cccc(CN3CC(C(=O)O)C3)c2)C2CCC2)ccc1Cl]

The title compound was prepared following a procedure analogous to Example 74 using 3-bromobenzaldehyde in step 1 and INT 68 (synthesis below) in step 2.

LC/MS method 4: MS (ESI): 399 [M+H]$^+$, rt=1.00 min.

1. (S)-2-Methyl-propane-2-sulfinic acid 1-4-chloro-3-methyl-phenyl)-meth-(E)-ylideneamide, INT 65

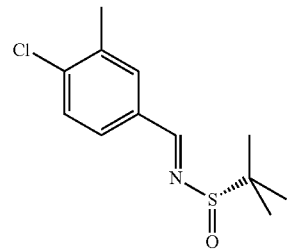 [SMILES: Cc1cc(/C=N/[S@@](=O)C(C)(C)C)ccc1Cl]

A mixture of 4-chloro-3-methylbenzaldehyde (10.7 g, 69.2 mmol), (S)-2-methylpropane-2-sulfinamide (9.23 g, 76 mmol) and Ti(OiPr)$_4$ (29.5 g, 104 mmol) in toluene (180 mL) was stirred at 50° C. overnight. The reaction was cooled down and quenched with saturated aqueous NaHCO$_3$. The resulting precipitate was filtered over Celite and washed with EtOAc. The organic layer was washed with saturated aqueous NaHCO$_3$ and the aqueous layers extracted with EtOAc. The combined organic layers were washed with brine, dried over sodium sulfate, filtered and concentrated to give the crude product which was purified by chromatography on silica gel (cyclohexane/EtOAc) to give INT 65.

LC/MS method 2: MS (ESI): 285 [M+H]$^+$, rt=0.77 min. $^1$H-NMR (CDCl$_3$): δ (ppm) 8.52 (s, 1H), 7.71 (d, 1H), 7.61 (dd, 1H), 7.44 (d, 1H), 2.44 (s, 3H), 1.26 (s, 9H).

2. (S)-2-Methyl-propane-2-sulfinic acid [(R)-(4-chloro-3-methyl-phenyl)-cyclobutyl-methyl]-amide, INT 66 and (S)-2-Methyl-propane-2-sulfinic acid [(S)-(4-chloro-3-methyl-phenyl)-cyclobutyl-methyl]-amide, INT 67

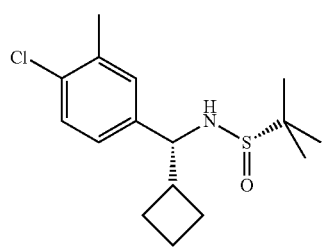

INT 66

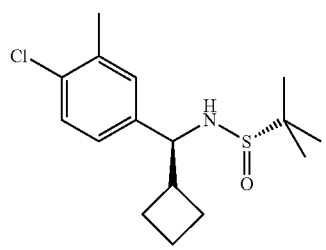

INT 67

To a solution of INT 65 (1 g, 3.88 mmol) in CH$_2$Cl$_2$ (25 mL) at −50° C. was added dropwise cyclobutyl magnesium chloride (0.5 M in THF) (15.52 mL, 7.76 mmol) and the resulting mixture was allowed to warm up slowly to room temperature overnight. The mixture was then quenched with saturated aqueous NH$_4$Cl and extracted with EtOAc. The organic layer was washed with brine, dried over sodium sulfate, filtered and concentrated. The crude product was purified by chromatography on silica gel (cyclohexane/EtOAc) to give INT 66 and INT 67.

INT 66: LC/MS method 3: MS (ESI): 314 [M+H]$^+$, rt=1.55 min. $^1$H-NMR (CDCl$_3$): δ (ppm) 7.27 (d, 1H), 7.12 (d, 1H), 7.03 (dd, 1H), 4.21 (d, 1H), 3.28 (s, 1H), 2.55 (m, 1H), 2.35 (s, 3H), 2.13 (m, 1H), 1.94-1.78 (m, 3H), 1.76-1.67 (m, 2H), 1.17 (s, 9H).

INT 67: LC/MS method 3: MS (ESI): 314 [M+H]$^+$, rt=1.55 min. $^1$H-NMR (CDCl$_3$): δ (ppm) 7.28 (d, 1H), 7.14 (d, 1H), 7.05 (dd, 1H), 4.18 (dd, 1H), 3.32 (d, 1H), 2.70 (m, 1H), 2.36 (s, 3H), 2.62-2.14 (m, 1H), 2.00-1.89 (m, 1H), 1.89-1.79 (m, 1H), 1.80-1.68 (m, 2H), 1.64 (q, 1H), 1.20 (s, 9H).

3. (3a) (R)-1-(4-Chloro-3-methyl-phenyl)-1-cyclobutyl-methylamine, INT 68

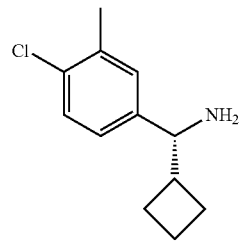

To a solution of INT 66 (94 mg, 0.299 mmol) in MeOH (1 mL) was added HCl (4 M in dioxane, 0.150 mL, 0.600 mmol) and the mixture was stirred at room temperature overnight. The mixture was then concentrated and the INT 68 was crystallized from Et$_2$O.

$^1$H-NMR (DMSO-d$_6$): δ (ppm) 8.48 (br s, 3H), 7.48 (d, 1H), 7.46 (d, 1H), 7.33 (dd, 1H), 4.17 (d, 1H), 2.78 (m, 1H), 2.34 (s, 3H), 2.14-2.04 (m, 1H), 2.04-1.95 (m, 1H), 1.86-1.70 (m, 2H), 1.65 (q, 2H).

4. (3b) (S)-1-(4-Chloro-3-methyl-phenyl)-1-cyclobutyl-methylamine, INT 69

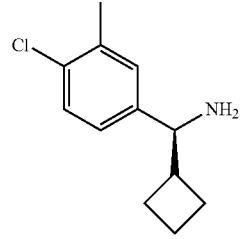

To a solution of INT 67 (260 mg, 0.828 mmol) in MeOH (1 mL) was added HCl (4 M in dioxane, 0.414 mL, 1.66 mmol) and the mixture was stirred at room temperature overnight. The mixture was then concentrated and the INT 69 was crystallized from Et$_2$O.

$^1$H-NMR (DMSO-d$_6$): δ (ppm) 8.48 (br s, 3H), 7.48 (d, 1H), 7.46 (d, 1H), 7.33 (dd, 1H), 4.17 (d, 1H), 2.78 (m, 1H), 2.34 (5, 3H), 2.14-2.04 (m, 1H), 2.04-1.95 (m, 1H), 1.86-1.70 (m, 2H), 1.65 (q, 2H).

Example 77

1-(3-{[(S)-(4-Chloro-3-methyl-phenyl)-cyclobutyl-methyl]-amino}-benzyl)-azetidine-3-carboxylic acid

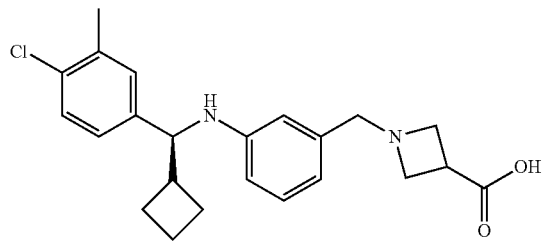 [SMILES: Cc1cc([C@@H](Nc2cccc(CN3CC(C(=O)O)C3)c2)C2CCC2)ccc1Cl]

The title compound was prepared following a procedure analogous to Example 74 using 3-bromobenzaldehyde in step 1 and INT 69 in step 2.

LC/MS method 2: MS (ESI): 399 [M+H]+, rt=2.19 min.

Example 78

1-{4-[(R)-1-(4-Chloro-3-methyl-phenyl)-propylamino]-pyridin-2-ylmethyl}-azetidine-3-carboxylic acid

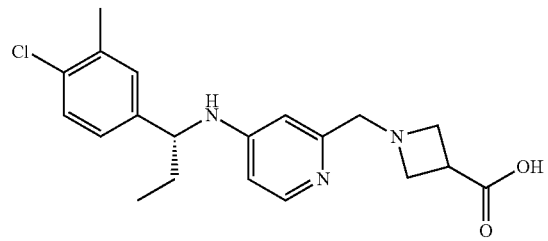

1. 1-(4-Bromo-pyridin-2-ylmethyl)-azetidine-3-carboxylic acid Pert-butyl ester, INT 70

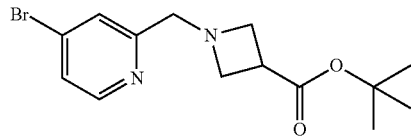 [SMILES: CC(C)(C)OC(=O)C1CN(Cc2cc(Br)ccn2)C1]

A mixture of 4-bromopyridine-2-carbaldehyde (768 mg, 3.51 mmol) and azetidine-3-carboxylic acid tert-butyl ester hydrochloride (680 mg, 3.51 mmol) in 1,2-dichloroethane (35 mL) was stirred at room temperature for 45 minutes. NaBH(OAc)$_3$ (1.49 g, 7.02 mmol) was then added and the mixture was stirred at room temperature for 18 hours. The mixture was diluted in CH$_2$Cl$_2$ and washed with saturated aqueous sodium bicarbonate, water and brine, dried over sodium sulfate, filtered and concentrated. The crude was purified by chromatography on silica gel (heptane/EtOAc) to give INT 70.

LC/MS method 3: MS (ESI): 328 [M+H]+, rt=0.89 min. $^1$H-NMR (DMSO-d$_6$): δ (ppm) 8.37 (d, 1H), 7.55 (m, 2H), 7.53 (m, 2H), 3.65 (s, 2H), 3.45 (t, 2H), 3.25 (q, 2H), 2.50 (m, 1H), 1.41 (s, 9H).

2. 1-{4-[(R)-1-(4-Chloro-3-methyl-phenyl)-propylamino]-pyridin-2-ylmethyl}-azetidine-3-carboxylic acid To a solution of INT 70 (200 mg, 0.611 mmol), (R)-1-(4-chloro-3-methyl-phenyl)-propylamine (135 mg, 0.733 mmol) and sodium tert-butoxide (141 mg, 1.467 mmol) in degassed toluene (3 mL) were added Pd$_2$(dba)$_3$ (28.0 mg, 0.031 mmol) and BINAP (38.1 mg, 0.061 mmol) and the resulting mixture was stirred at 70° C. overnight. Another portion of Pd$_2$(dba)$_3$ (28.0 mg, 0.031 mmol) and BINAP (38.1 mg, 0.061 mmol) were added and the mixture was further stirred at 70° C. overnight. The solvent was evaporated and the crude product treated with TFA (2 ml) and the resulting mixture stirred at room temperature for 1 hour. The TFA was evaporated, water was added and the pH was set to 7. The aqueous layer was extracted with CH$_2$Cl$_2$. The aqueous layer containing the product was lyophilized. The mixture obtained was suspended in DMSO and the solid was filtered off. The filtrate was purified by flash chromatography (Reverse phase C18, H$_2$O/CH$_3$CN) to give 78.

LC/MS method 2: MS (ESI): 374 [M+H]+, rt=1.42 min. $^1$H-NMR (DMSO-d$_6$): δ (ppm) 7.81 (d, 1H), 7.31 (d, 1H), 7.30 (s, 1H), 7.15 (d, 1H), 7.01 (d, 1H), 6.43 (s, 1H), 6.26 (s, 1H), 4.26 (q, 1H), 3.40 (AB, 2H), 3.37-3.10 (m, 5H), 2.28 (s, 3H), 1.79-1.70 (m, 1H), 1.69-1.61 (m, 1H), 1.087 (t, 3H).

Example 79

1-{5-Chloro-2-[(R)-1-(4-chloro-3-methyl-phenyl)-propylamino]-pyridin-4-ylmethyl}-azetidine-3-carboxylic acid

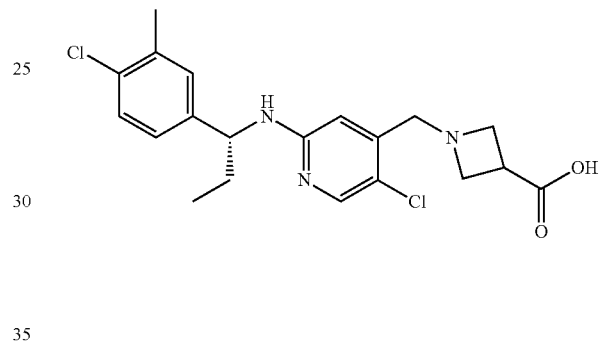

The title compound was prepared following a procedure analogous Example 78 using 2-bromo-5-chloropyridine-4-carboxaldehyde in step 1.

LC/MS method 2: MS (ESI): 408 [M+H]+, rt=1.94 min.

Example 80

3-{5-[(R)-1-(4-Chloro-3,5-dimethyl-phenyl)-propylamino]-2-methyl-benzylamino}-2,2-dimethyl-propionic acid

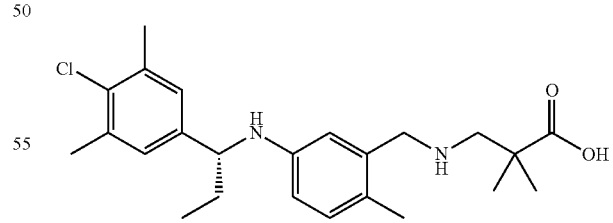

The title compound was prepared according to Scheme 3 following a procedure analogous to Example 21 using amine INT 38 (synthesis see Example 41) in step 4 and 3-amino-2,2-dimethyl-propionic acid in step 6.

LC/MS method 2: MS (ESI): 417 [M+H]+, rt=2.19 min.

Example 81

(S)-3-{5-[(R)-1-(4-Chloro-3,5-dimethyl-phenyl)-propylamino]-2-methyl-benzylamino}-2-methyl-propionic acid

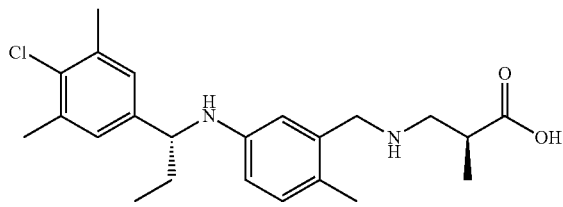 [SMILES: CC[C@@H](Nc1ccc(C)c(CNC[C@H](C)C(=O)O)c1)c1cc(C)c(Cl)c(C)c1]

The title compound was prepared according to Scheme 3 following a procedure analogous to Example 21 using amine INT 38 (synthesis see Example 41) in step 4 and (S)-3-amino-2-methyl-propionic acid in step 6.
LC/MS method 2: MS (ESI): 403 [M+H]$^+$, rt=2.18 min.

Example 82

3-({5-[(R)-1-(4-Chloro-3,5-dimethyl-phenyl)-propylamino]-2-methyl-benzyl}-methyl-amino)-propionic acid

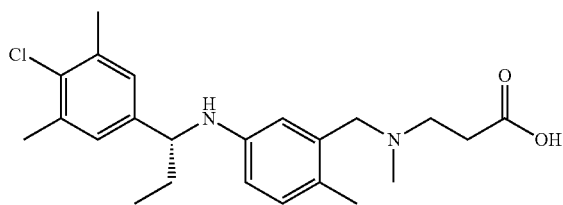 [SMILES: CC[C@@H](Nc1ccc(C)c(CN(C)CCC(=O)O)c1)c1cc(C)c(Cl)c(C)c1]

The title compound was prepared according to Scheme 3 following a procedure analogous to Example 21 using amine INT 38 (synthesis see Example 41) in step 4 and 3-methylamino-propionic acid in step 6.
LC/MS method 2: MS (ESI): 403 [M+H]$^+$, rt=2.58 min.

Example 83

1-{5-[(S)-1-(4-Chloro-3-methyl-phenyl)-2,2,2-trifluoro-ethylamino]-2-methyl-benzyl}-3-methyl-pyrrolidine-3-carboxylic acid

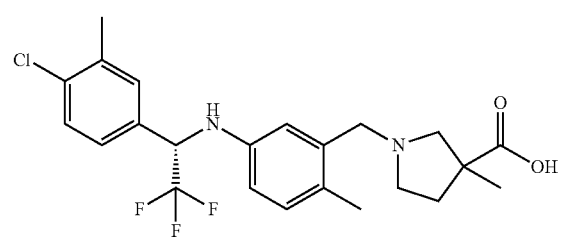 [SMILES: Cc1cc([C@H](Nc2ccc(C)c(CN3CCC(C)(C(=O)O)C3)c2)C(F)(F)F)ccc1Cl]

The title compound was prepared according to Scheme 3 following a procedure analogous to Example 21 using 3-methyl-pyrrolidine-3-carboxylic acid in step 6.
LC/MS method 2: MS (ESI): 455 [M+H]$^+$, rt=2.34 min.

Example 84

(R)-1-{5-Chloro-2-[(S)-1-(4-chloro-3-methyl-phenyl)-2,2,2-trifluoro-ethylamino]-pyridin-4-ylmethyl}-pyrrolidine-3-carboxylic acid

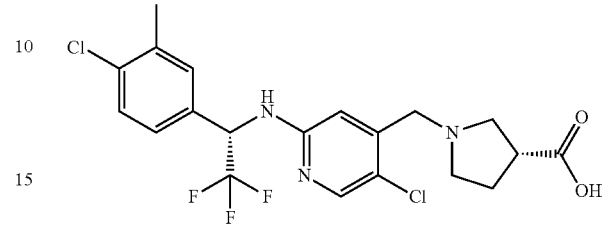

The title compound was prepared according to Scheme 3 following a procedure analogous to Example 57 using INT51 and (S)-1-(4-Chloro-3-methyl-phenyl)-2,2,2-trifluoro-ethylamine hydrochloride in step 2 and (R)-pyrrolidine-3-carboxylic acid in step 4.
LC/MS method 4: MS (ESI): 462 [M+H]$^+$, rt=0.95 min.

Example 85

3-({5-Chloro-2-[(S)-1-(4-chloro-3-methyl-phenyl)-2,2,2-trifluoro-ethylamino]-pyridin-4-ylmethyl}-amino)-propionic acid

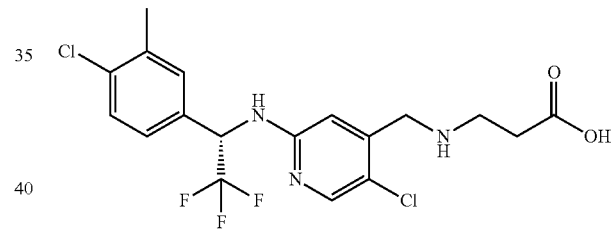

The title compound was prepared according to Scheme 3 following a procedure analogous to Example 57 using INT51 and (S)-1-(4-Chloro-3-methyl-phenyl)-2,2,2-trifluoro-ethylamine hydrochloride in step 2 and 3-amino-propionic acid in step 4.
LC/MS method 4: MS (ESI): 436 [M+H]$^+$, rt=0.91 min.

Example 86

1-{5-Chloro-2-[(R)-1-(4-chloro-3-methyl-phenyl)-propylamino]-pyridin-4-ylmethyl}-3-methyl-pyrrolidine-3-carboxylic acid

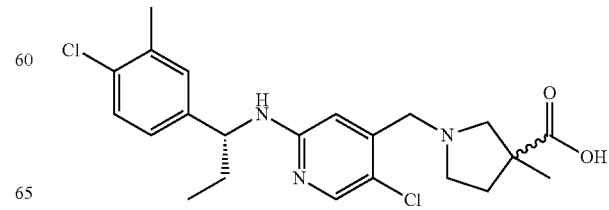

The title compound (single stereoisomer A) was obtained by preparative chiral separation of Example 57. Separation was performed using a Chiralpak AD-i 5×20 cm (20 μM) column and heptane/CH$_2$Cl$_2$/EtOH/TFA (75:22:3:0.05) as mobile phase with a flow of 40 ml/min and UV detection (254 nM).

Chiral HPLC (Chiralpak AD-i 4.6×250 mm (20 μM), heptane/CH$_2$Cl$_2$/EtOH/TFA (75:22:3:0.05), 0.7 ml/min, UV detection (254 nm)): rt=9.74 min.

LC/MS method 2: MS (ESI): 436 [M+H]$^+$, rt=1.85 min.

Example 87

1-{5-Chloro-2-[(R)-1-(4-chloro-3-methyl-phenyl)-propylamino]-pyridin-4-ylmethyl}-3-methyl-pyrrolidine-3-carboxylic acid

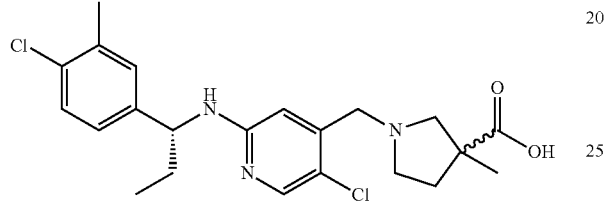

The title compound (single stereoisomer B) was obtained by preparative chiral separation of Example 57. Separation was performed using a Chiralpak AD-i 5×20 cm (20 μM) column and heptane/CH$_2$Cl$_2$/EtOH/TFA (75:22:3:0.05) as mobile phase with a flow of 40 ml/min and UV detection (254 nM).

Chiral HPLC (Chiralpak AD-i 4.6×250 mm (20 μM), heptane/CH$_2$Cl$_2$/EtOH/TFA (75:22:3:0.05), 0.7 ml/min, UV detection (254 nm)): rt=13.44 min.

LC/MS method 2: MS (ESI): 436 [M+H]$^+$, rt=1.91 min.

The compounds of formula (I) and/or formula (II) in free form or in salt form, exhibit valuable pharmacological properties, e.g. properties susceptible to lymphocytes interactions or sphingosine-1-phosphate receptor (SIP) modulating properties, in particular S1P-antagonistic efficacy, especially S1P1-antagonistic efficacy, e.g. as indicated in in vitro and in vivo tests as provided in the next sections and are therefore indicated for therapy.

Biological Testing

Human S1P1 Receptor Calcium FLIPR Antagonist Assay (HeLa Gα16 S1P1)

The assay measures intracellular changes of Ca$^{2+}$ mediated by the synthetic probing agonist 3-{[2-(2-Trifluoromethyl-biphenyl-4-yl)-benzo[b]thiophen-5-ylmethyl]-amino}-propionic acid (GNF-AC-1) in the HeLa-S1P1/Gα16 cell clone 1: HeLa (human cervix carcinoma, ATCC CCL2) cells stably expressing N-terminally myc-tagged human S1P1 receptors (GenBank™ accession No. NM_001400; UNIPROT P21453) and promiscuous Gα16 protein (GenBank™ accession number M63904, Swissprot P30679) are cultured at 37° C., 5% CO2, and 95% relative humidity. The cells are plated in 384 well black plates (10'000 cells per well). After 24 hours the cells are loaded with Fluo-4-AM (1.6 μM in HBSS and 2.5 mM probenicid) for 1 hour at 37° C. After washing, the cells are transferred to the FLIPR. The test compounds are added at different concentrations (≤100 μM) in HBSS in the presence of 0.1% BSA and changes in fluorescence are recorded (indication of agonism). The probing agonist is added 20-30 minutes afterwards to the wells at a concentration giving 80% of the maximal activity (EC$_{80}$). After each addition, time points are collected as follows: 20 time points (2 seconds) before the addition of the agonist (Fmin) and 60 time points (1 or 2 seconds) after the addition of the probing agonist. This allows the determination of the maximal fluorescence (Fmax). The ratio (Fmax−Fmin)/Fmin is plotted against the log of the concentration of the test compounds and the IC$_{50}$ (relative antagonism) is calculated using the XLfit-4 software. Compounds with an inhibition <20% are usually considered "inactive". A concentration-response curve of the probing agonist is determined on each plate in parallel.

The IC$_{50}$ values of compounds of formula (I) in the above described Human S1P Receptor Calcium FLIPR Antagonist Assay are displayed in Table 1.

TABLE 1

| Example No. | IC$_{50}$ [nM] |
| --- | --- |
| 1 | 14.7 |
| 2 | 3.5 |
| 3 | 0.9 |
| 4 | 0.2 |
| 6 | 0.5 |
| 7 | 1.2 |
| 8 | 1.5 |
| 9 | 0.4 |
| 10 | 1.6 |
| 11 | 4.0 |
| 13 | 4.7 |
| 14 | 1.5 |
| 15 | 2.3 |
| 17 | 1.6 |
| 18 | 1.9 |
| 20 | 2.0 |
| 21 | 1.0 |
| 22 | 0.8 |
| 23 | 1.0 |
| 24 | 1.9 |
| 25 | 3.3 |
| 26 | 2.1 |
| 27 | 10.6 |
| 28 | 0.8 |
| 29 | 0.4 |
| 30 | 0.9 |
| 31 | 1.0 |
| 32 | 0.8 |
| 33 | 0.6 |
| 34 | 0.8 |
| 35 | 1.8 |
| 36 | 3.7 |
| 37 | 2.5 |
| 38 | 0.8 |
| 39 | 0.8 |
| 40 | 0.4 |
| 41 | 1.3 |
| 42 | 1.0 |
| 43 | 0.8 |
| 44 | 6.7 |
| 45 | 1.2 |
| 46 | 1.3 |
| 47 | 1.6 |
| 48 | 2.4 |
| 49 | 2.4 |
| 52 | 0.9 |
| 53 | 1.2 |
| 54 | 0.9 |
| 55 | 0.5 |
| 57 | 2.4 |
| 58 | 0.1 |
| 59 | 1.2 |
| 60 | 2.1 |
| 61 | 1.6 |
| 62 | 0.9 |
| 63 | 1.1 |
| 64 | 1.7 |
| 65 | 0.2 |
| 66 | 1.2 |

TABLE 1-continued

| Example No. | IC$_{50}$ [nM] |
|---|---|
| 67 | 0.8 |
| 68 | 0.7 |
| 69 | 0.8 |
| 70 | 0.1 |
| 71 | 0.1 |
| 72 | 1.1 |
| 73 | 1.2 |
| 74 | 14.1 |
| 75 | 2.8 |
| 76 | 5.7 |
| 78 | 0.8 |
| 79 | 0.6 |
| 80 | 24.5 |
| 81 | 3.9 |
| 82 | 3.0 |
| 83 | 2.9 |
| 84 | 0.4 |
| 85 | 0.9 |
| 86 | 1.2 |
| 87 | 0.7 |

B. In vivo

The compounds of the invention, e.g. compounds of formula (I) typically induce the depletion of blood lymphocyte as may be determined in the assay described below. Moreover, compounds of the invention, e.g. compounds of formula (I) are typically efficacious in the said assay also when administered via the per oral route of administration.

Measurement of Circulating Lymphocytes:

The test compounds (or salts thereof) are dissolved in a vehicle such as water, saline, PEG (polyethylene glycol) 200, or PBS (phosphate buffered saline). Adult mice (C57BU6NCrl strain, female, 18-20 g) or rats (Lewis strain, male, 6-12 weeks old) are administered up to 60 mg/kg of the test compounds in 10 ml/kg (C57BU6NCrl mice) or 2 ml/kg (Lewis rats) vehicle via per oral application. The vehicle or a reference salt and FTY720 (0.3 mg/kg) are used as negative and positive controls, respectively. Blood is collected from the sublingual vein at single time points, e.g. 14 or 24 hours after the test compound administration, under short isoflurane anesthesia. Two to three animals are used in each group. Whole blood samples are subjected to hematology analysis. Peripheral lymphocyte counts are determined using an automated analyzer. The Haemathology System uses a combination of light scatter, cytochemical staining and nuclear density on two independent channels to measure the total and differential white cell counts. The reduction of lymphocytes provoked by each test compound is calculated by comparing the lymphocyte counts measured after each treatment to the mean lymphocyte counts measured in five to eight untreated mice or rats, respectively. The data are presented as mean±STDEV.

As an example, Table 2 shows the effect on lymphocyte counts at the indicated time points in hours after oral administration of a given dose in mg/kg of some compounds of formula (I) to the indicated species, as compared to the mean lymphocyte counts of untreated animals.

TABLE 2

| Example No | Species | Dose (mg/kg) | Time point (hours) | Residual Lymphocyte Counts 24 hours after p.o. dosing |
|---|---|---|---|---|
| 21 | C57BL/6NCrl mice | 30 | 24 | 17.8% ± 2.3 |
| 55 | C57BL/6NCrl mice | 30 | 24 | 43.6% ± 4.6 |
| 43 | C57BL/6NCrl mice | 30 | 24 | 21.8% ± 3.4 |
| 29 | C57BL/6NCrl mice | 30 | 24 | 35.6% ± 4.6 |

TABLE 2-continued

| Example No | Species | Dose (mg/kg) | Time point (hours) | Residual Lymphocyte Counts 24 hours after p.o. dosing |
|---|---|---|---|---|
| 34 | C57BL/6NCrl mice | 30 | 24 | 24.2% ± 2.3 |
| 62 | C57BL/6NCrl mice | 30 | 24 | 31.5% ± 8.0 |
| 42 | C57BL/6NCrl mice | 30 | 24 | 19.4% ± 2.3 |
| 42 | Lewis rats | 30 | 24 | 22.2% ± 6.7 |
| 65 | C57BL/6NCrl mice | 30 | 24 | 22.6% ± 11.4 |
| 66 | C57BL/6NCrl mice | 30 | 24 | 19.4% ± 2.3 |
| 41 | C57BL/6NCrl mice | 30 | 24 | 20.2% ± 8.0 |
| 30 | C57BL/6NCrl mice | 30 | 24 | 19.4% ± 2.3 |
| 30 | Lewis rats | 30 | 24 | 26.9 ± 13.0 |
| 32 | C57BL/6NCrl mice | 30 | 24 | 17.0% ± 3.4 |
| 33 | C57BL/6NCrl mice | 30 | 24 | 16.2% ± 2.3 |
| 23 | C57BL/6NCrl mice | 30 | 24 | 25.1% ± 3.4 |
| 70 | C57BL/6NCrl mice | 30 | 24 | 20.2% ± 5.7 |
| 31 | C57BL/6NCrl mice | 30 | 24 | 23.4% ± 3.4 |
| 61 | C57BL/6NCrl mice | 30 | 24 | 16.2% ± 4.6 |
| 84 | Lewis rats | 30 | 24 | 16.8% ± 7.2 |
| 85 | Lewis rats | 30 | 24 | 11.6% ± 0.3 |

The compounds of the invention, e.g. compounds of formula (I) in free form or in pharmaceutically acceptable salt form, exhibit valuable pharmacological properties, e.g. as S1P1 receptor antagonists, e.g. as indicated in the above in vitro and in vivo tests and are therefore indicated for therapy.

Utilities

Compounds of the invention may be useful in the treatment of an indication selected from:

Diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, neuropathic pain, Behcet's disease, Wegener's granulamatosis, ankylosing spondylitis, polymyositis, CIDP (Chronic Idiopathic Demyelinating Polyneuropathy), diabetes type I or Ii and the disorders associated therewith, vasculitis, pernicious anemia, Sjoegren syndrome, uveitis, psoriasis, Graves ophthalmopathy, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, e.g. hepatitis B or C, chronic bacterial infection, or neurodegenerative diseases, e.g. Alzheimer disease, amyotrophic lateral sclerosis or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus.

Furthermore, the compounds of the invention, e.g. compounds of formula (I) are useful in the treatment and/or prevention of diseases or disorders associated with deregulated angiogenesis for example diseases caused by ocular neovascularisation, especially retinopathies (diabetic retinopathy, age-related macular degeneration); psoriasis; haemangioblastomas, such as "strawberry-marks" (=haemangioma); various inflammatory diseases, such as arthritis, especially rheumatoid arthritis, arterial atherosclerosis and atherosclerosis occurring after transplants, endometriosis or chronic asthma; and, especially, tumor diseases (solid tumors, but also leukemias and other liquid tumors).

Thus, as a further embodiment, the present invention provides the use of a compound of the invention, e.g. a compound of formula (I) or a salt thereof in therapy.

In a further embodiment, the therapy is selected from a disease which may be treated by an antagonist of sphingosine-1-phosphate.

In another embodiment, the disease is selected from the afore-mentioned list, suitably diseases or disorders mediated by lymphocytes interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, neuropathic pain, Behcet's disease, Wegener's granulamatosis, ankylosing spondylitis, polymyositis, CIDP (Chronic Idiopathic Demyelinating Polyneuropathy), diabetes type I or II and the disorders associated therewith, vasculitis, pernicious anemia, Sjoegren syndrome, uveitis, psoriasis, Graves ophthalmopathy, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, e.g. hepatitis B or C, chronic bacterial infection, or neurodegenerative diseases, e.g. Alzheimer disease, amyotrophic lateral sclerosis or senile dementia. Examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus;

also suitably in the treatment and/or prevention of diseases or disorders associated with deregulated angiogenesis for example diseases caused by ocular neovascularisation, especially retinopathies (diabetic retinopathy, age-related macular degeneration); psoriasis; haemangioblastomas, such as "strawberry-marks" (=haemangioma); various inflammatory diseases, such as arthritis, especially rheumatoid arthritis, arterial atherosclerosis and atherosclerosis occurring after transplants, endometriosis or chronic asthma; and, especially, tumor diseases (solid tumors, but also leukemias and other liquid tumors).

In another embodiment, the invention provides a method of treating a disease which is treated by the modulation of the S1P receptor comprising administration of a therapeutically acceptable amount of a compound of formula (I) or a salt thereof. In a further embodiment, the disease is selected from the afore-mentioned lists The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

Combinations

The compound of the present invention may be administered either simultaneously with, or before or after, one or more other therapeutic agent. The compound of the present invention may be administered separately, by the same or different route of administration, or together in the same pharmaceutical composition as the other agents. The compounds of formula (I) or formula (II) may be administered as the sole active ingredient or in conjunction with, e.g. as an adjuvant to, other drugs e.g. immunosuppressive or immunomodulating agents or other anti-inflammatory agents, e.g. for the treatment or prevention of alto- or xenograft acute or chronic rejection or inflammatory or autoimmune disorders, or a chemotherapeutic agent, e.g a malignant cell anti-proliferative agent. For example, the compounds of formula (I) or formula (II) may be used in combination with a calcineurin inhibitor, e.g. cyclosporin A or FK 506; a mTOR inhibitor, e.g. rapamycin, 40-O-(2-hydroxyethyl)-rapamycin, CCI779, ABT578, AP23573, AP23464, AP23675, AP23841, TAFA-93, biolimus-7 or biolimus-9; an ascomycin having immunosuppressive properties, e.g. ABT-281, ASM981 (Pimecrolimus), etc.; corticosteroids; cyclophosphamide; azathioprene; methotrexate; leflunomide; mizoribine; mycophenolic acid or salt; mycophenolate mofetil; 15-deoxyspergualine or an immunosuppressive homologue, analogue or derivative thereof; a PKC inhibitor, e.g. as disclosed in WO 02/38561 or WO 03/82859, e.g. the compound of Example 56 or 70; a JAK3 kinase inhibitor, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxyphenyl)-amino-6,7-dimethoxyquinazoline] (WHI-P154), [4-(3',5'-dibromo-4'-hydroxyphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO 04/052359 or WO 05/066156; a JAK2 kinase inhibitor, e.g. [7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-pyridin-3-yl]-amine (example 267 in WO2009098236), β-Cyclopentyl-4-(7H-pyrrolo[2,3-d]pyrimidin-4-yl)-((R)-1H-pyrazole-1-propanenitrile (INCB018424), lestaurtinib (CEP701), (N-tert-butyl-3-(5-methyl-2-(4-(2-(pyrrolidin-1-yl)ethoxy)phenylamino)pyrimidin-4-ylamino)benzenesulfonamide (TG101348), 11-[2-(1-pyrrolidinyl)ethoxy]-14,19-dioxa-5,7,27-triazatetra-cyclo[19.3.1.1(2,6).1(8,12)]heptacosa-1(25),2(27),3,5,8(26),9,11,16,21,23-decaene (SB1518 or ONX-0803), N-(cyanomethyl)-4-[2-[4-(4-morpholinyl)phenylamino]pyrimidin-4-yl]benzamide (CYT387); a STAT5 inhibitor such as N-[5-(2-Furyl)-1,3,4-oxadiazol-2-yl]-2-phenylquinoline-4-carboxamide (STX-0119); an IL-6 receptor antibody such as atlizumab; a sphingosine-1-phosphate receptor modulator such as FTY720 (fingolimod), or compounds disclosed in WO 2005/000833; immunosuppressive monoclonal antibodies, e.g., monoclonal antibodies to leukocyte receptors, e.g., MHC, CD2, CD3, CD4, CD7, CD8, CD25, CD28, CD40, CD45, CD52, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; or an anti-infectious agent.

In another embodiment the present invention relates to a combination comprising a compound of formula (I) or formula (II) or a salt thereof as described in any of the embodiments and at least another drug substance selected from a a JAK2 kinase inhibitor, e.g. [7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-pyridin-3-yl]-amine (example 267 in WO2009098236), β-Cyclopentyl-4-(7H-pyrrolo[2,3-d]pyrimidin-4-yl)-((3R)-1H-pyrazole-1-propanenitrile (INCB018424), lestaurtinib (CEP701), (N-tert-butyl-3-(5-methyl-2-(4-(2-(pyrrolidin-1-yl)ethoxy)phenylamino)pyrimidin-4-ylamino)-benzene-sulfonamide (TG101348), tasocitinib (CP690550), 11-[2-(1-pyrrolidinyl)ethoxy]-14,19-dioxa-5,7,27-triazatetra-cyclo[19.3.1.1(2,6).1(8,12)]heptacosa-1(25),2(27),3,5,8(26),9,11,16,21,23-decaene (SB1518 or ONX-0803), N-(cyanomethyl)-4-[2-[4-(4-morpholinyl)phenylamino]pyrimidin-4-yl]benzamide (CYT387), in free form or in a pharmaceutically acceptable salt form.

In another embodiment the present invention relates to a combination comprising a compound of formula (I) or formula (II) or a salt thereof as described in any of the embodiments and at least another drug substance selected from a a JAK3 kinase inhibitor, e.g. e.g. N-benzyl-3,4-dihydroxy-benzylidene-cyanoacetamide α-cyano-(3,4-dihydroxy)-N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxyphenyl)amino-6,7-dimethoxyquinazoline] (WHI-P154), [4-(3',5'-dibromo-4'-hydroxyphenyl)-amino-6,7-dimethoxyquinazoline] WHI-P97, KRX-211, in free form or in a pharmaceutically acceptable salt form.

A combination of a compound of formula (I) or formula (II) and at least another compound selected from a JAK2 and/or JAK3 inhibitor may be beneficial in the treatment of cancer such as breast cancer, colorectal carcinoma, Wilms tumor, or the like.

In another embodiment the present invention relates to the use of a combination as described above, e.g. a compound of formula (I) or formula (II) and at least another compound, e.g. selected from a JAK2 and/or JAK3 inhibitor for use in the treatment of cancer, in particular breast cancer, colorectal carcinoma, or Wilms tumor.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula (I) or formula (II) and a co-agent, are both administered to a patient simultaneously in the form of a single entity or dosage. The term "non-fixed combination" means that the active ingredients, e.g. a compound of formula (I) or formula (II) and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

In one embodiment, the invention provides a product comprising a compound of formula (I) or formula (II) and at least one other therapeutic agent as a combined preparation for simultaneous, separate or sequential use in therapy. In one embodiment, the therapy is the treatment of a disease or condition mediated by sphingosine-1-phosphate receptors. Products provided as a combined preparation include a composition comprising the compound of formula (I) or formula (II) and the other therapeutic agent(s) together in the same pharmaceutical composition, or the compound of formula (I) or formula (II) and the other therapeutic agent(s) in separate form, e.g. in the form of a kit.

In one embodiment, the invention provides a pharmaceutical composition comprising a compound of formula (I) or formula (II) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I) or formula (II). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) or formula (II) for treating a disease or condition mediated by sphingosine-1-phosphate receptors, wherein the medicament is prepared for administration with another therapeutic agent. The invention also provides the use of another therapeutic agent for treating a disease or condition mediated by sphingosine-1-phosphate receptors, wherein the medicament is administered with a compound of formula (I) or formula (II).

The invention also provides a compound of formula (I) or formula (II) for use in a method of treating a disease or condition mediated by sphingosine-1-phosphate receptors, wherein the compound of formula (I) or formula (II) is prepared for administration with another therapeutic agent. The invention also provides another therapeutic agent for use in a method of treating a disease or condition mediated by sphingosine-1-phosphate receptors, wherein the other therapeutic agent is prepared for administration with a compound of formula (I) or formula (II). The invention also provides a compound of formula (I) or formula (II) for use in a method of treating a disease or condition mediated by sphingosine-1-phosphate receptors, wherein the compound of formula (I) or formula (II) is administered with another therapeutic agent. The invention also provides another therapeutic agent for use in a method of treating a disease or condition mediated by sphingosine-1-phosphate receptors, wherein the other therapeutic agent is administered with a compound of formula (I) or formula (II).

SUMMARY OF THE INVENTION

Embodiment 1 describes a compound of formula (I) or a pharmaceutically acceptable salt thereof;

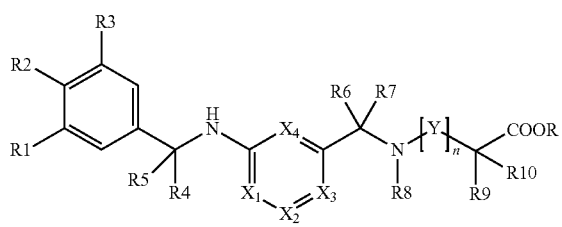

(I)

wherein,
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy optionally substituted by halogen;
or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl or they may form together with the carbon atom to which they are attached a 3-7 membered saturated carbocyclic ring;
R8 and R9 are independently selected from H and $C_1$-$C_6$ alkyl, or R8 and R9 may form together with the atoms to which they are attached a 4-7 membered heterocyclic ring, optionally substituted one or more times by $C_1$-$C_6$-alkyl optionally substituted by halogen, trifluoromethyl, hydroxy, or amino;
n=1, 2, 3 or 4;
R10 is hydrogen, $C_1$-$C_6$ alkyl, amino, hydroxy or $C_1$-$C_6$ alkoxy;
R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl optionally substituted by $C_1$-$C_6$ alkyl, $C_1$-$C_6$ alkoxy, halogen or hydroxy,
$X_1$, $X_2$, $X_3$ and $X_4$, are each independently selected from N or CR11,
R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and
Y stands in each occurrence independently for CR12R13 wherein R12 and R13 are independently selected from H and $C_1$-$C_6$ alkyl.

Embodiment 2 describes a compound of formula (II) or a pharmaceutically acceptable salt thereof,

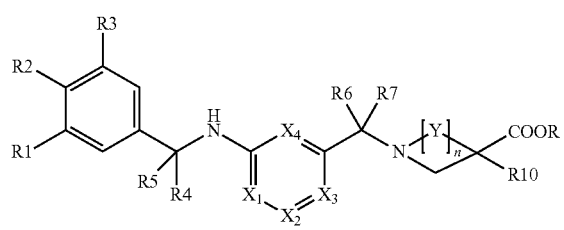

(II)

wherein
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy optionally substituted by halogen;
or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl, or they may form together with the carbon atom to which they are attached a 3-7 membered saturated carbocyclic ring;
n=1, 2, 3 or 4;
R10 is hydrogen, $C_1$-$C_6$ alkyl, amino, hydroxy or $C_1$-$C_6$ alkoxy;

R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl, said phenyl being optionally substituted by $C_1$-$C_6$ alkyl, $C_1$-$C_6$ alkoxy, halogen or hydroxy;

$X_1$, $X_2$, $X_3$ and $X_4$, are each independently selected from N or CR11,

R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and Y stands in each occurrence independently for CR12R13 wherein R12 and R13 are independently selected from H and $C_1$-$C_6$ alkyl optionally substituted by halogen.

Embodiment 3 describes a compound of embodiment 1 or 2 or a pharmaceutically acceptable salt thereof, wherein R1 and R stand for hydrogen.

Embodiment 4 describes a compound of any of the preceding enumerated embodiments or a pharmaceutically acceptable salt thereof, wherein n is 2.

Embodiment 5 describes a compound of any of the preceding enumerated embodiments, wherein $X_3$ is CR11 and wherein R11 stands for methyl.

Embodiment 6 describes a compound in accordance to any of the preceding enumerated embodiments or a pharmaceutically acceptable salt thereof, wherein R4 is trifluoromethyl and R5 is hydrogen.

Embodiment 7 describes a compound of embodiment 1 or 2 or a pharmaceutically acceptable salt thereof, which is selected from:

1-{3-[1-(4-Chloro-3-methyl-phenyl)-ethylamino]-benzyl}-azetidine-3-carboxylic acid,
1-{3-[1-(4-Chloro-3-methyl-phenyl)-propylamino]-benzyl}-azetidine-3-carboxylic acid,
1-{3-[(R)-1-(4-Chloro-3-methyl-phenyl)-propylamino]-benzyl}-azetidine-3-carboxylic acid,
1-{5-[1-(4-Chloro-3-methyl-phenyl)-propylamino]-2-methyl-benzyl}-azetidine-3-carboxylic acid,
1-{3-[1-(4-Chloro-3-methyl-phenyl)-propylamino]-4-methyl-benzyl}-azetidine-3-carboxylic acid,
1-(1-{3-[(R)-1-(4-Chloro-3-methyl-phenyl)-propylamino]-phenyl}-ethyl)-azetidine-3-carboxylic acid,
1-{3-[1-(4-Chloro-3-methyl-phenyl)-propylamino]-2-methyl-benzyl}-azetidine-3-carboxylic acid,
1-{3-[(R)-1-(4-Chloro-3-methyl-phenyl)-propylamino]-benzyl}-3-methyl-azetidine-3-carboxylic acid,
1-{3-[1-(4-Chloro-3-methyl-phenyl)-propylamino]-5-methyl-benzyl}-azetidine-3-carboxylic acid,
1-(1-{5-[1-(4-Chloro-3-methyl-phenyl)-propylamino]-2-methyl-phenyl}-ethyl)-azetidine-3-carboxylic acid,
(R)-1-{3-[(R)-1-(4-Chloro-3-methyl-phenyl)-propylamino]-benzyl}-pyrrolidine-3-carboxylic acid,
(S)-1-{3-[(R)-1-(4-Chloro-3-methyl-phenyl)-propylamino]-benzyl}-pyrrolidine-3-carboxylic acid,
1-(1-{3-[(R)-1-(4-Chloro-3-methyl-phenyl)-propylamino]-phenyl)-propyl}azetidine-3-carboxylic acid,
(R)-1-{3-[1-(4-Chloro-3-methyl-phenyl)-propylamino]-2-methyl-benzyl}-pyrrolidine-3-carboxylic acid,
(R)-1-{3-[1-(4-Chloro-3-methyl-phenyl)-propylamino]-5-methyl-benzyl}-pyrrolidine-3-carboxylic acid,
1-{3-[(R)-1-(4-Chloro-3-methyl-phenyl)-propylamino]-benzyl}-3-ethyl-azetidine-3-carboxylic acid,
1-{3-[1-(4-Chloro-3-methyl-phenyl)-2-methyl-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(5-Chloro-naphthalen-2-yl)-propylamino]-benzyl}-azetidine-3-carboxylic acid,
(R)-1-{5-[(S)-1-(4-Chloro-3-methyl-phenyl)-2,2,2-trifluoro-ethylamino]-2-methyl-benzyl}-pyrrolidine-3-carboxylic acid,
1-{5-[(R)-1-(4-Chloro-3-methyl-phenyl)-propylamino]-2-methyl-benzyl}-azetidine-3-carboxylic acid,
(R)-1-{5-[(R)-1-(4-Chloro-3-methyl-phenyl)-propylamino]-2-methyl-benzyl}-pyrrolidine-3-carboxylic acid,
1-{3-[(R)-1-(4-Chloro-3-methyl-phenyl)-propylamino]-2-fluoro-benzyl}-azetidine-3-carboxylic acid,
(R)-1-{3-[(R)-1-(4-Chloro-3-methyl-phenyl)-propylamino]-2-fluoro-benzyl}-pyrrolidine-3-carboxylic acid,
1-{3-[(R)-1-(4-Chloro-3-methyl-phenyl)-propylamino]-4-fluoro-benzyl}-azetidine-3-carboxylic acid,
(R)-1-{3-[(R)-1-(4-Chloro-3-methyl-phenyl)-propylamino]-4-fluoro-benzyl}-pyrrolidine-3-carboxylic acid,
1-{5-[(R)-1-(4-Chloro-3-methyl-phenyl)-propylamino]-2-methyl-benzyl}-3-methyl-azetidine-3-carboxylic acid,
(R)-1-{2-Chloro-5-[(S)-1-(4-chloro-3-methyl-phenyl)-2,2,2-trifluoro-ethylamino]-benzyl}-pyrrolidine-3-carboxylic acid,
(R)-1-{3-[(S)-1-(4-Chloro-3-methyl-phenyl)-2,2,2-trifluoro-ethylamino]-2,6-dimethyl-benzyl}-pyrrolidine-3-carboxylic acid,
1-{3-[(S)-1-(4-Chloro-3-methyl-phenyl)-2,2,2-trifluoro-ethylamino]-2,6-dimethyl-benzyl}-azetidine-3-carboxylic acid,
(R)-1-{3-[(R)-1-(4-Chloro-3-methyl-phenyl)-propylamino]-2,6-dimethyl-benzyl}-pyrrolidine-3-carboxylic acid,
1-{3-[(R)-1-(4-Chloro-3-methyl-phenyl)-propylamino]-2,6-dimethyl-benzyl}-azetidine-3-carboxylic acid,
(R)-1-{5-[(S)-1-(4-Chloro-3-methyl-phenyl)-2,2,2-trifluoro-ethylamino]-2-ethyl-benzyl}-pyrrolidine-3-carboxylic acid,
1-{5-[(S)-1-(4-Chloro-3-methyl-phenyl)-2,2,2-trifluoro-ethylamino]-2-ethyl-benzyl}-azetidine-3-carboxylic acid,
(R)-1-{5-[(R)-1-(4-Chloro-3-methyl-phenyl)-propylamino]-2-ethyl-benzyl}-pyrrolidine-3-carboxylic acid,
1-{5-[(R)-1-(4-Chloro-3-methyl-phenyl)-propylamino]-2-ethyl-benzyl}-azetidine-3-carboxylic acid,
(R)-1-{2-Chloro-5-[(R)-1-(4-chloro-3-methyl-phenyl)-propylamino]-benzyl}-pyrrolidine-3-carboxylic acid,
1-{3-[(S)-1-(4-Chloro-3-methyl-phenyl)-2,2,2-trifluoro-ethylamino]-2-methyl-benzyl}-azetidine-3-carboxylic acid,
3-{3-[(S)-1-(4-Chloro-3-methyl-phenyl)-2,2,2-trifluoro-ethylamino]-2,6-dimethyl-benzylamino}-propionic acid,
1-{5-[(R)-1-(4-Chloro-3,5-dimethyl-phenyl)-propylamino]-2-methyl-benzyl}-azetidine-3-carboxylic acid,
(R)-1-{5-[(R)-1-(4-Chloro-3,5-dimethyl-phenyl)-propylamino]-2-methyl-benzyl}-pyrrolidine-3-carboxylic acid,
(R)-1-{2-Chloro-5-[(R)-1-(4-chloro-3,5-dimethyl-phenyl)-propylamino]-benzyl}-pyrrolidine-3-carboxylic acid,
(R)-1-{5-[(R)-1-(4-Chloro-3,5-dimethyl-phenyl)-ethylamino]-2-methyl-benzyl}-pyrrolidine-3-carboxylic acid,
3-{5-[(R)-1-(4-Chloro-3,5-dimethyl-phenyl)-propylamino]-2-methyl-benzylamino}-propionic acid,
(R)-1-{2-Chloro-5-[(R)-1-(4-chloro-3,5-dimethyl-phenyl)-ethylamino]-benzyl}-pyrrolidine-3-carboxylic acid,
3-{5-[(R)-1-(4-Chloro-3,5-dimethyl-phenyl)-ethylamino]-2-methyl-benzylamino}-propionic acid,
3-{2-Chloro-5-[(R)-1-(4-chloro-3,5-dimethyl-phenyl)-propylamino]-benzylamino}-propionic acid,
(R)-3-{5-[(R)-1-(4-Chloro-3,5-dimethyl-phenyl)-propylamino]-2-methyl-benzylamino}-2-methyl-propionic acid, 3-{5-[(S)-1-(4-Chloro-3,5-dimethyl-phenyl)-2,2,2-trifluoro-ethylamino]-2-methyl-benzylamino}-propionic acid,
3-{2-Chloro-5-[(S)-1-(4-chloro-3,5-dimethyl-phenyl)-2,2,2-trifluoro-ethylamino]-benzylamino}-propionic acid,
3-{2-Chloro-5-[(S)-1-(4-chloro-3-methyl-phenyl)-2,2,2-trifluoro-ethylamino]-benzylamino}-propionic acid,
3-{2-Chloro-5-[(R)-1-(4-chloro-3,5-dimethyl-phenyl)-propylamino]-benzylamino}-propionic acid,
1-{2-[(R)-1-(4-Chloro-3-methyl-phenyl)-propylamino]-5-fluoro-pyridin-4-ylmethyl}-azetidine-3-carboxylic acid,
(R)-1-{5-Chloro-2-[(R)-1-(4-chloro-3-methyl-phenyl)-propylamino]-pyridin-4-ylmethyl}-pyrrolidine-3-carboxylic acid,
(R)-1-{5-[(R)-1-(4-Chloro-3-methyl-phenyl)-propylamino]-2-methyl-pyridin-3-ylnnethyl}-pyrrolidine-3-carboxylic acid,
1-{5-Chloro-2-[(R)-1-(4-chloro-3-methyl-phenyl)-propylamino]-pyridin-4-ylmethyl}-3-methyl-pyrrolidine-3-carboxylic acid,
3-({5-Chloro-2-[(R)-1-(4-chloro-3-methyl-phenyl)-propylamino]-pyridin-4-ylmethyl}-amino)-propionic acid,
(R)-1-{5-Chloro-2-[(R)-1-(4-chloro-3,5-dimethyl-phenyl)-propylamino]-pyridin-4-ylmethyl}-pyrrolidine-3-carboxylic acid,
(R)-1-{2-[(R)-1-(4-Chloro-3-methyl-phenyl)-propylamino]-5-methyl-pyridin-4-ylmethyl}-pyrrolidine-3-carboxylic acid,
1-{2-Chloro-5-[(R)-1-(4-chloro-3,5-dimethyl-phenyl)-propylamino]-benzyl}-azetidine-3-carboxylic acid,
1-{2-Chloro-5-[(R)-1-(4-chloro-3-methyl-phenyl)-propylamino]-benzyl}-azetidine-3-carboxylic acid,
1-{2-Chloro-5-[(R)-1-(4-chloro-3-methyl-phenyl)-2-methyl-propylamino]-benzyl}-azetidine-3-carboxylic acid,
1-{2-Chloro-5-[(R)-1-(4-chloro-3,5-dimethyl-phenyl)-2-methyl-propylamino]-benzyl}-azetidine-3-carboxylic acid,
1-{2-Chloro-5-[(S)-1-(4-chloro-3-methyl-phenyl)-2,2,2-trifluoro-ethylamino]-benzyl}-3-methyl-azetidine-3-carboxylic acid,
1-{2-Chloro-5-[(R)-1-(4-chloro-3,5-dimethyl-phenyl)-propylamino]-benzyl}-3-methyl-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{5-[(S)-1-(4-Chloro-3-methyl-phenyl)-2,2,2-trifluoro-ethylamino]-2-trifluoromethyl-benzyl}-azetidine-3-carboxylic acid,
1-{5-[(S)-1-(4-Chloro-3-methyl-phenyl)-2,2,2-trifluoro-ethylamino]-2-methyl-benzyl}-azetidine-3-carboxylic acid,
1-{5-[(S)-1-(4-Chloro-3-methyl-phenyl)-2,2,2-trifluoro-ethylamino]-2-fluoro-benzyl}-azetidine-3-carboxylic acid,
1-{2-Chloro-5-[(S)-1-(4-chloro-3-methyl-phenyl)-2,2,2-trifluoro-ethylamino]-benzyl}-pyrrolidine-3-carboxylic acid,
3-((S)-1-{3-[(S)-1-(4-Chloro-3-methyl-phenyl)-2,2,2-trifluoro-ethylamino]-phenyl}-ethylamino)-propionic acid
1-{6-[(R)-1-(4-Chloro-3-methyl-phenyl)-propylamino]-pyridin-2-ylmethyl}-azetidine-3-carboxylic acid,
1-{2-[(R)-1-(4-Chloro-3-methyl-phenyl)-propylamino]-pyridin-4-ylmethyl}-azetidine-3-carboxylic acid,
1-(3-{[(R)-(4-Chloro-3-methyl-phenyl)cyclobutyl-methyl]-amino}-benzyl)-azetidine-3-carboxylic acid,
1-(3-{[(S)-(4-Chloro-3-methyl-phenyl)-cyclobutyl-methyl]-amino}-benzyl)-azetidine-3-carboxylic acid,
1-{4-[(R)-1-(4-Chloro-3-methyl-phenyl)-propylamino]pyridin-2-ylmethyl}-azetidine-3-carboxylic acid,
1-{5-Chloro-2-[(R)-1-(4-chloro-3-methyl-phenyl)-propylamino]-pyridin-4-ylmethyl}-azetidine-3-carboxylic acid,
3-{5-[(R)-1-(4-Chloro-3,5-dimethyl-phenyl)-propylamino]-2-methyl-benzylamino}-2,2-dimethyl-propionic acid,
(S)-3-{5-[(R)-1-(4-Chloro-3,5-dimethyl-phenyl)-propylamino]-2-methyl-benzylamino}-2-methyl-propionic acid,
3-({5-[(R)-1-(4-Chloro-3,5-dimethyl-phenyl)-propylamino]-2-methyl-benzyl}-methyl-amino)-propionic acid,
1-{5-[(S)-1-(4-Chloro-3-methyl-phenyl)-2,2,2-trifluoro-ethylamino]-2-methyl-benzyl}-3-methyl-pyrrolidine-3-carboxylic acid,
(R)-1-{5-Chloro-2-[(S)-1-(4-chloro-3-methyl-phenyl)-2,2,2-trifluoro-ethylamino]-pyridin-4-ylmethyl}-pyrrolidine-3-carboxylic acid,
3-({5-Chloro-2-[(S)-1-(4-chloro-3-methyl-phenyl)-2,2,2-trifluoro-ethylamino]-pyridin-4-ylmethyl}-amino)-propionic acid,
1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer A), and
1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer B).

Embodiment 8 describes a method for preventing or treating diseases or disorders which are mediated by lymphocytes interactions, in a subject in need of such treatment or prevention, which method comprises administering to said subject an effective amount of a compound of formula (I) or a compound of formula (II) in accordance to the definition of embodiment 1 or 2 or a pharmaceutically acceptable salt thereof.

Embodiment 9 describes the use of a compound of formula (I) or a compound of formula (II) according to embodiment 1 or 2 or a pharmaceutically acceptable salt thereof, in the preparation of a medicament for the treatment and/or prevention of diseases or disorders mediated by lymphocytes interactions.

Embodiment 10 describes a compound of formula (I) or a compound of formula (II) according to embodiment 1 or 2 or a pharmaceutically acceptable salt thereof for use as a medicament, in particular for use in the treatment and/or prevention of diseases or disorders mediated by lymphocytes interactions.

Embodiment 11 describes a method, use or a compound for use of any of the preceding enumerated embodiments, wherein said diseases or disorders mediated by lymphocytes interactions pertain to transplantation, such as acute or chronic rejection of cell, tissue or organ allo- or xenografts or delayed graft function, graft versus host disease, autoimmune diseases, e.g. rheumatoid arthritis, systemic lupus erythematosus, hashimoto's thyroidis, multiple sclerosis, myasthenia gravis, neuropathic pain, Behcet's disease, Wegener's granulamatosis, ankylosing spondylitis, polymyositis, CIDP (Chronic Idiopathic Demyelinating Polyneuropathy), diabetes type I or II and the disorders associated therewith, vasculitis, pernicious anemia, Sjoegren syndrome, uveitis, psoriasis, Graves ophthalmopathy, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock, cancer, e.g. breast cancer, T cell lymphomas or T cell leukemias, infectious diseases, e.g. toxic shock (e.g. superantigen induced), septic shock, adult respiratory distress syndrome or viral infections, e.g. AIDS, viral hepatitis, e.g. hepatitis B or C, chronic bacterial infection, or neurodegenerative diseases, e.g. Alzheimer disease, amyotrophic lateral sclerosis, or senile dementia, wherein examples of cell, tissue or solid organ transplants include e.g. pancreatic islets, stem cells, bone marrow, corneal tissue, neuronal tissue, heart, lung, combined heart-lung, kidney, liver, bowel, pancreas, trachea or oesophagus, deregulated angiogenesis e.g. diseases caused by ocular neovascularisation, especially retinopathies (diabetic retinopathy, age-related macular degeneration); psoriasis; haemangioblastomas, such as "strawberry-marks" (=haemangioma); various inflammatory diseases, such as arthritis, especially rheumatoid arthritis, arterial atherosclerosis and atherosclerosis occurring after transplants, endometriosis or chronic asthma; and, especially, tumor diseases (solid tumors, but also leukemias and other liquid tumors).

Embodiment 12 describes a method, use or a compound for use of any of the preceding enumerated embodiments, wherein said disease or said disorder is selected from an autoimmune disease, such as rheumatoid arthritis, systemic lupus erythematosus, inflammatory bowel disease, psoriasis, or multiple sclerosis; or wherein said disorder is a tumor disease such as solid tumors, but also leukemias and other liquid tumors.

Embodiment 13 describes a combination, e.g. a pharmaceutical combination or a kit, comprising a) a first agent which is a compound of formula (I) or formula (II) as disclosed in embodiment 1 or embodiment 2, or a salt thereof, in particular a pharmaceutically acceptable salt thereof, and b) at least one co-agent, e.g. an immunosuppressant, immunomodulatory, anti-inflammatory, chemotherapeutic or anti-infectious agent.

Embodiment 14 describes a pharmaceutical composition, in particular for use in any of the methods of the preceding enumerated embodiments, comprising a compound of formula (I) or a compound of formula (II) of embodiment 1 or embodiment 2 or a pharmaceutically acceptable salt thereof in association with a pharmaceutically acceptable diluent or carrier therefore.

Embodiment 15 describes a method of manufacturing a compound of formula (I) in accordance to embodiment 1, comprising reacting:
(A) a nitro aldehyde derivative of formula (i) with an amine of formula (ii) under reductive amination conditions, e.g. with a sodium borohydride such as sodium borohydride triacetate in the presence of a base, such as Hünig's base, to furnish the nitro intermediate (iii),

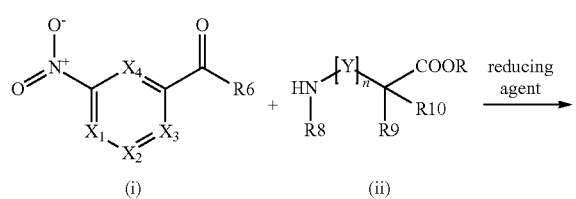

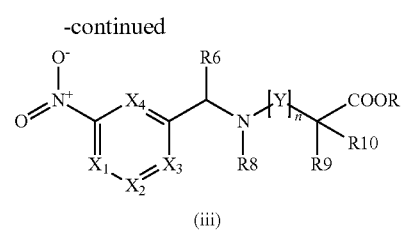

which is converted to the amino-derivative (iv) e.g. by chemical reduction such as hydrogenation in the presence (e.g. palladium on carbon) or absence of a catalyst (e.g. $SnCl_2$ in diluted aqueous hydrochloric acid),

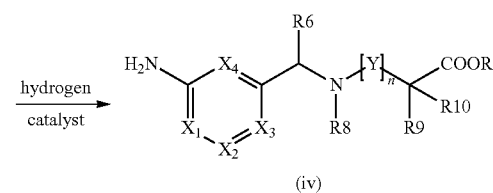

which is further reacted with the keto-derivative (v) e.g. under reductive amination conditions e.g. with decaborane, to furnish a compound (vi),

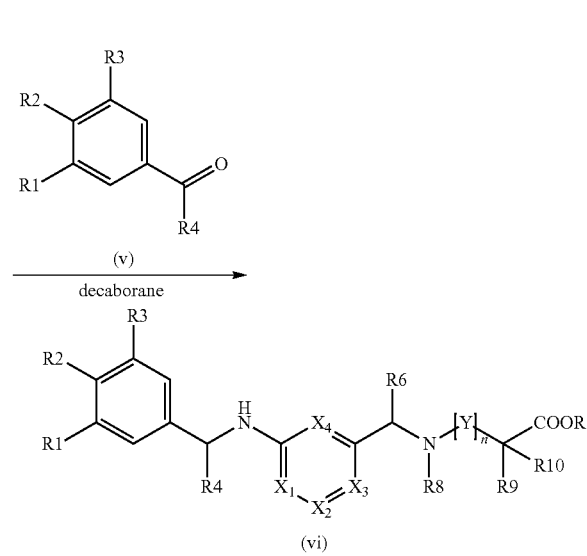

which may or may not be cleaved to the acid, e.g. by treating ester of formula (vi) with an acid such as hydrochlorid acid or alternatively with a base such as LiOH in water, to a final compound in accordance to the definition of formula (I'):

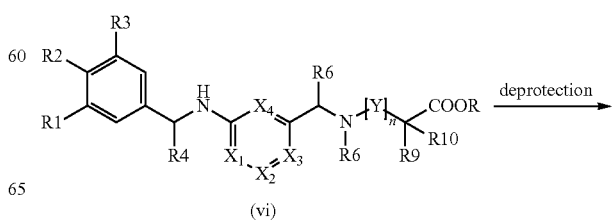

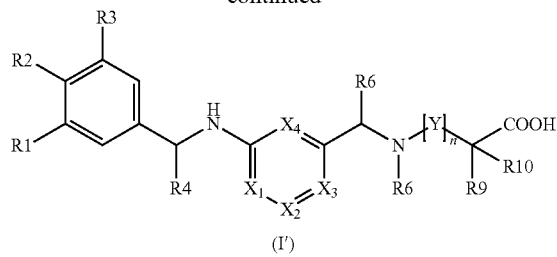

(I')

or reacting:

(B) a keto derivative of formula (v) with an amine derivative of formula (vii) under reductive amination conditions e.g. with a decaborane in the presence of a solvent, e.g. methanol to yield the halo-derivative of formula (viii),

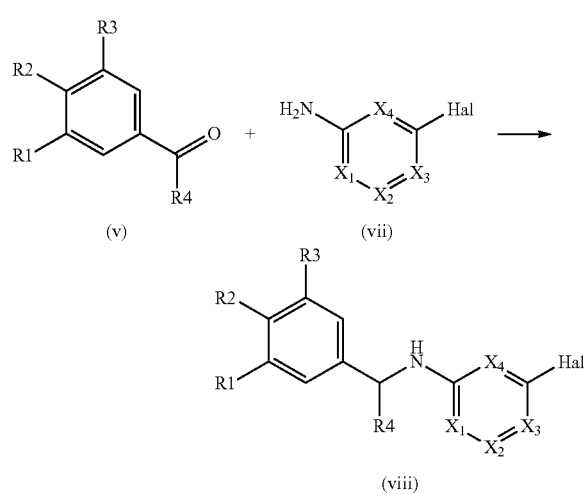

which is converted to the aldehyde of formula (ix) for example by a halogen metal exchange reaction with an appropriate organolithium reagent, e.g. t-BuLi (t-butyllithium) and subsequent quenching with DMF,

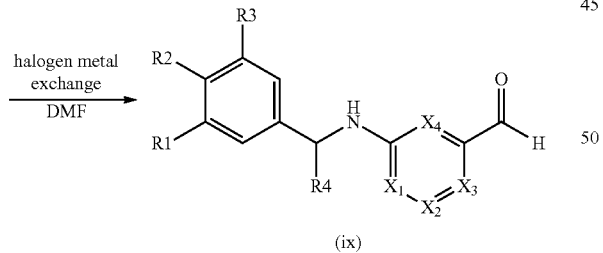

which is reacted with amine of formula (ii) under reductive amination conditions to furnish the ester of formula (vi), or it will furnish the acid of formula (vi) when R=hydrogen,

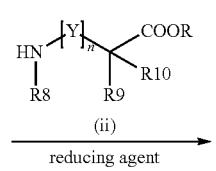

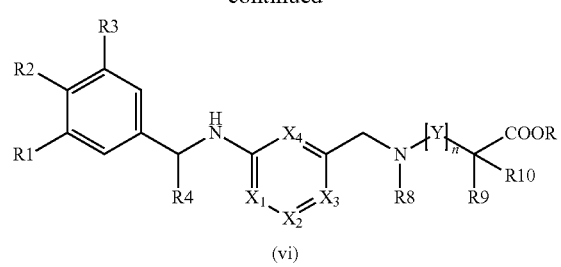

(vi)

or alternatively, aldehyde of formula (ix) is converted with an appropriate Grignard reagent to furnish the alcohol derivative (x),

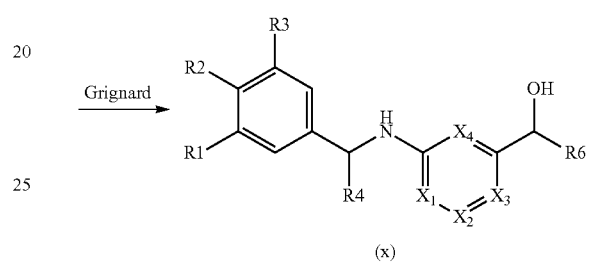

(x)

which is converted to the ketone derivative (xi) by an oxidation reaction such as Dess-Martin periodinane, or with pyridin-SO$_3$ complex, typically in the presence of a solvent, e.g. an aprotic solvent, e.g. methylenechloride,

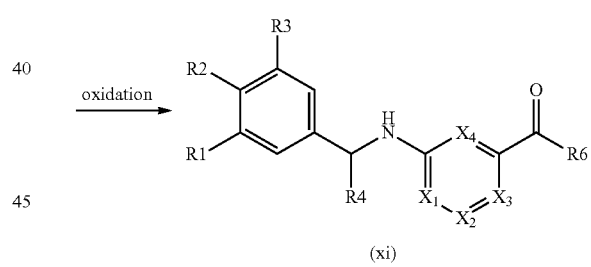

(xi)

which ketone (xi) is then converted under reductive amination conditions as described hereinbefore with an amine of formula (ii) into final compound of formula (xii), which may be optionally treated for example with an acid, e.g. with hydrochloric acid, or with a base, e.g. LiOH in water, to cleave the ester into the carboxylic acid (R=hydrogen);

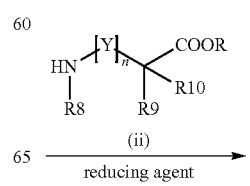

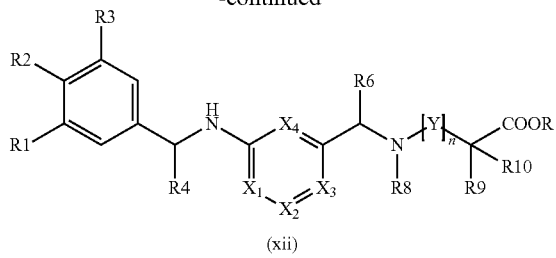

(xii)

or reacting:
(C) an amine of formula (xiii) with the halo-derivative (xiv) under Buchwald coupling conditions for example with a catalyst e.g. tris(dibenzylideneacetone)dipalladium(0) in the presence of a base such as sodium bis(trimethylsilyl)amide or a tert-butoxide, to furnish acetal derivative (xv), wherein each R' independently represents a $C_{1-6}$alkyl, $C_{3-7}$cycloalkyl, benzyl, or wherein both R' with the oxygen atoms to which they are attached form a 5, 6 or 7 membered ring system, such as methylenedioxolane, ethylenedioxolane, propylenedioxolane,

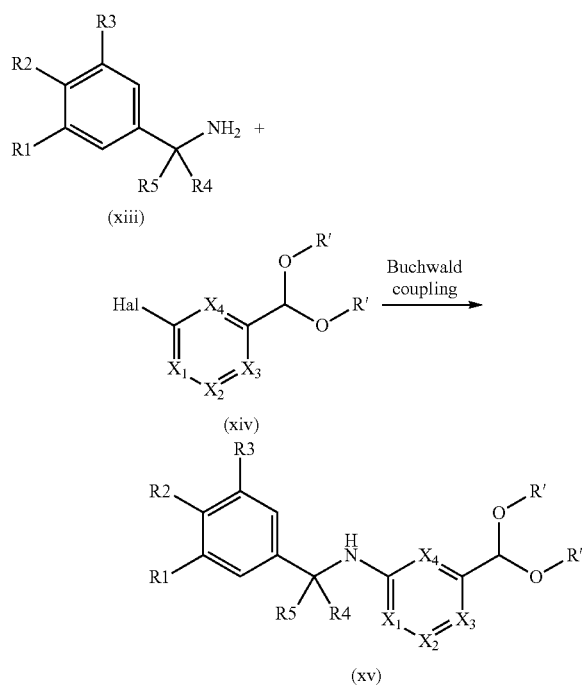

which is deprotected e.g. by reacting the acetal-derivative with an acid, e.g. hydrochloric or hydrobromic acid to furnish aldehyde (xvi),

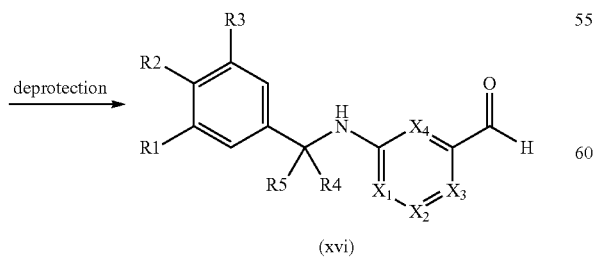

which is reacted with amine-derivative of formula (ii) to furnish final compound of formula (xvii), which may be optionally treated for example with an acid, e.g. with hydrochloric acid, or alternatively with a base, such as LiOH in water, to cleave the ester into the carboxylic acid (R=hydrogen);

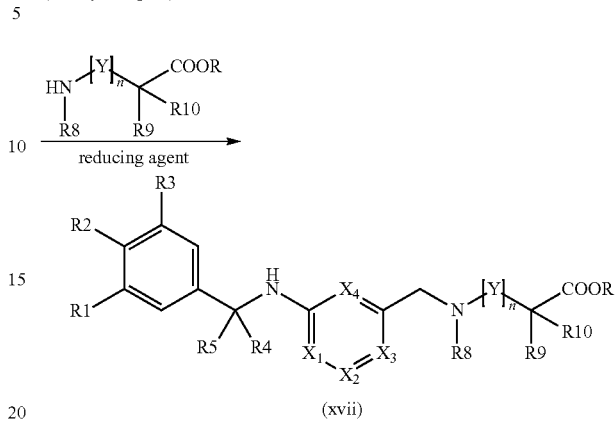

(xvii)

or reacting:
(D) a haloketone of formula (xviii) and an amine of formula (ii) under reductive amination conditions as described hereinbefore to furnish halo-ester intermediate of formula (xix),

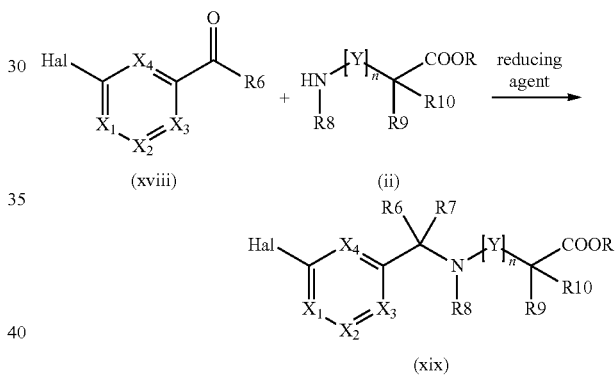

or alternatively a haloamine derivative of formula (xx) is reacted with an acrylic acid derivative (xxi) in the presence of a Lewis acid such as boron trifluoride etherate to furnish the halo-ester intermediate of formula (xix),

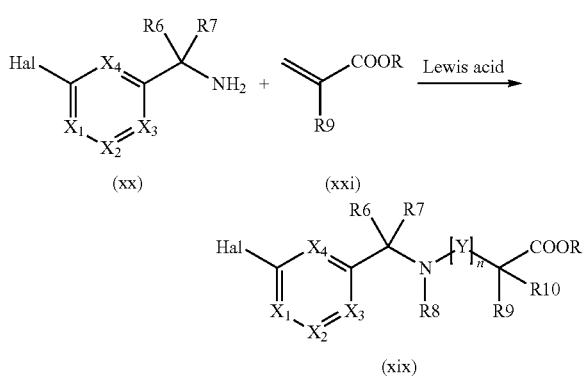

which is reacted with an amine of formula (xiii) under Buchwald reaction conditions, e.g. with a catalyst e.g. tris(dibenzylideneacetone)dipalladium(0) in the presence of a base such as sodium bis(trimethylsilyl)amide or a tert-butoxide to furnish ester compound (xxii), which may be optionally treated for example with an acid, e.g. with hydrochloric acid, to cleave the ester into the carboxylic acid (R=hydrogen).

(xiii)

Buchwald coupling (xxii)

Embodiment 16 describes a compound of formula (I) or a pharmaceutically acceptable salt thereof;

(I)

wherein,
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy;
or R1 and R2 together with the C-atoms to which they are attached form an aryl ring with 6-10 carbon atoms, which may optionally be substituted by 1-4 substituents selected from cyano, $C_1$-$C_4$-alkyl, $C_1$-$C_4$-alkoxy, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl or they may form together with the carbon atom to which they are attached a 3-7 membered saturated carbocyclic ring;
R8 and R9 are independently selected from H and $C_1$-$C_6$ alkyl, or R8 and R9 may form together with the atoms to which they are attached a 4-7 membered heterocyclic ring, optionally substituted one or more times by $C_1$-$C_6$-alkyl, trifluoromethyl, hydroxy, $C_1$-$C_6$ alkoxy, or amino;
n=1, 2, 3 or 4;
R10 is hydrogen, $C_1$-$C_6$ alkyl, amino, hydroxy or $C_1$-$C_6$ alkoxy;
R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl optionally substituted by $C_1$-$C_6$ alkyl, $C_1$-$C_6$ alkoxy, halogen or hydroxy,
$X_1$, $X_2$, $X_3$ and $X_4$, are each independently selected from N or CR11,
R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and
Y stands in each occurrence independently for CR12R13 wherein R12 and R13 are independently selected from H and $C_1$-$C_6$ alkyl.

Embodiment 17 describes a compound of formula (II) or a pharmaceutically acceptable salt thereof, (II)

wherein
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy;
or R1 and R2 together with the C-atoms to which they are attached form an aryl ring with 6-10 carbon atoms, which may optionally be substituted by 1-4 substituents selected from cyano, $C_1$-$C_4$-alkyl, $C_1$-$C_4$-alkoxy, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;
R5 is hydrogen or $C_1$-$C_6$ alkyl;
R6 and R7 are independently selected from H and $C_1$-$C_6$ alkyl, or they may form together with the carbon atom to which they are attached a 3-7 membered saturated carbocyclic ring;
n=1, 2, 3 or 4;
R10 is hydrogen, $C_1$-$C_6$ alkyl, amino, hydroxy or $C_1$-$C_6$ alkoxy;
R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl, said phenyl being optionally substituted by $C_1$-$C_6$ alkyl, $C_1$-$C_6$ alkoxy, halogen or hydroxy;
$X_1$, $X_2$, $X_3$ and $X_4$, are each independently selected from N or CR11,
R11 in each case being independently selected from H, halo, cyano, $C_1$-$C_6$ alkoxy, $C_1$-$C_6$ alkyl optionally substituted by halo; or —$SO_2$—$C_1$-$C_6$ alkyl; and
Y stands in each occurrence independently for CR12R13 wherein R12 and R13 are independently selected from H and $C_1$-$C_6$ alkyl optionally substituted by halogen.

Embodiment 18 describes a compound of embodiment 16 or 17 or a pharmaceutically acceptable salt thereof, wherein R1 and R stand for hydrogen.

Embodiment 19 describes a compound of embodiment 16 or 17 or a pharmaceutically acceptable salt thereof, wherein n is 2.

Embodiment 20 describes a compound of embodiment 16 or 17 or a pharmaceutically acceptable salt thereof, wherein $X_3$ is CR11 and wherein R11 stands for methyl.

Embodiment 21 describes a compound of embodiment 16 or 17 or a pharmaceutically acceptable salt thereof, wherein R4 is trifluoromethyl and R5 is hydrogen.

Embodiment 22 describes a compound of embodiment 16 or 17 or a pharmaceutically acceptable salt thereof, which is selected from:

1-{3-[1-(4-Chloro-3-methyl-phenyl)-ethylamino]-benzyl}-azetidine-3-carboxylic acid,
1-{3-[1-(4-Chloro-3-methyl-phenyl)-propylamino]-benzyl}-azetidine-3-carboxylic acid,
1-{3-[(R)-1-(4-Chloro-3-methyl-phenyl)-propylamino]-benzyl}-azetidine-3-carboxylic acid,
1-{5-[1-(4-Chloro-3-methyl-phenyl)-propylamino]-2-methyl-benzyl}-azetidine-3-carboxylic acid,
1-{3-[1-(4-Chloro-3-methyl-phenyl)-propylamino]-4-methyl-benzyl}-azetidine-3-carboxylic acid,
1-(1-{3-[(R)-1-(4-Chloro-3-methyl-phenyl)-propylamino]-phenyl}-ethyl)-azetidine-3-carboxylic acid,
1-{3-[1-(4-Chloro-3-methyl-phenyl)-propylamino]-2-methyl-benzyl}-azetidine-3-carboxylic acid,
1-{3-[(R)-1-(4-Chloro-3-methyl-phenyl)-propylamino]-benzyl}-3-methyl-azetidine-3-carboxylic acid,
1-{3-[1-(4-Chloro-3-methyl-phenyl)-propylamino]-5-methyl-benzyl}-azetidine-3-carboxylic acid,
1-(1-{5-[1-(4-Chloro-3-methyl-phenyl)-propylamino]-2-methyl-phenyl}-ethyl)-azetidine-3-carboxylic acid,
(R)-1-{3-[(R)-1-(4-Chloro-3-methyl-phenyl)-propylamino]-benzyl}-pyrrolidine-3-carboxylic acid,
(S)-1-{3-[(R)-1-(4-Chloro-3-methyl-phenyl)-propylamino]-benzyl}-pyrrolidine-3-carboxylic acid,
1-(1-{3-[(R)-1-(4-Chloro-3-methyl-phenyl)-propylamino]-phenyl}-propyl)-azetidine-3-carboxylic acid,
(R)-1-{3-[1-(4-Chloro-3-methyl-phenyl)-propylamino]-2-methyl-benzyl}-pyrrolidine-3-carboxylic acid,
(R)-1-{3-[1-(4-Chloro-3-methyl-phenyl)-propylamino]-5-methyl-benzyl}-pyrrolidine-3-carboxylic acid,
1-{3-[(R)-1-(4-Chloro-3-methyl-phenyl)-propylamino]-benzyl}-3-ethyl-azetidine-3-carboxylic acid,
1-{3-[1-(4-Chloro-3-methyl-phenyl)-2-methyl-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(4-Chloro-3,5-dimethyl-phenyl)-propylamino]-benzyl}-azetidine-3-carboxylic acid,
1-{3-[(R)-1-(5-Chloro-naphthalen-2-yl)-propylamino]-benzyl}-azetidine-3-carboxylic acid,
(R)-1-{5-[(S)-1-(4-Chloro-3-methyl-phenyl)-2,2,2-trifluoro-ethylamino]-2-methyl-benzyl}-pyrrolidine-3-carboxylic acid,
1-{5-[(R)-1-(4-Chloro-3-methyl-phenyl)-propylamino]-2-methyl-benzyl}-azetidine-3-carboxylic acid,
(R)-1-{5-[(R)-1-(4-Chloro-3-methyl-phenyl)-propylamino]-2-methyl-benzyl}-pyrrolidine-3-carboxylic acid,
1-{3-[(R)-1-(4-Chloro-3-methyl-phenyl)-propylamino]-2-fluoro-benzyl}-azetidine-3-carboxylic acid,
(R)-1-{3-[(R)-1-(4-Chloro-3-methyl-phenyl)-propylamino]-2-fluoro-benzyl}-pyrrolidine-3-carboxylic acid,
1-{3-[(R)-1-(4-Chloro-3-methyl-phenyl)-propylamino]-4-fluoro-benzyl}-azetidine-3-carboxylic acid, and
(R)-1-{3-[(R)-1-(4-Chloro-3-methyl-phenyl)-propylamino]-4-fluoro-benzyl}-pyrrolidine-3-carboxylic acid.

Embodiment 23 describes a compound of embodiment 16 or 17 or a pharmaceutically acceptable salt thereof, which is selected from:

(R)-1-{3-[(R)-1-(4-Chloro-3-methyl-phenyl)-propylamino]-4-fluoro-benzyl}-pyrrolidine-3-carboxylic acid,
1-{5-[(R)-1-(4-Chloro-3-methyl-phenyl)-propylamino]-2-methyl-benzyl}-3-methyl-azetidine-3-carboxylic acid,
(R)-1-{2-Chloro-5-[(S)-1-(4-chloro-3-methyl-phenyl)-2,2,2-trifluoro-ethylamino]-benzyl}-pyrrolidine-3-carboxylic acid,
(R)-1-{3-[(S)-1-(4-Chloro-3-methyl-phenyl)-2,2,2-trifluoro-ethylamino]-2,6-dimethyl-benzyl}-pyrrolidine-3-carboxylic acid,
1-{3-[(S)-1-(4-Chloro-3-methyl-phenyl)-2,2,2-trifluoro-ethylamino]-2,6-dimethyl-benzyl}-azetidine-3-carboxylic acid,
(R)-1-{3-[(R)-1-(4-Chloro-3-methyl-phenyl)-propylamino]-2,6-dimethyl-benzyl}-pyrrolidine-3-carboxylic acid,
1-{3-[(R)-1-(4-Chloro-3-methyl-phenyl)-propylamino]-2,6-dimethyl-benzyl}-azetidine-3-carboxylic acid,
(R)-1-{5-[(S)-1-(4-Chloro-3-methyl-phenyl)-2,2,2-trifluoro-ethylamino]-2-ethyl-benzyl}-pyrrolidine-3-carboxylic acid,
1-{5-[(S)-1-(4-Chloro-3-methyl-phenyl)-2,2,2-trifluoro-ethylamino]-2-ethyl-benzyl}-azetidine-3-carboxylic acid,
(R)-1-{5-[(R)-1-(4-Chloro-3-methyl-phenyl)-propylamino]-2-ethyl-benzyl}-pyrrolidine-3-carboxylic acid,
1-{5-[(R)-1-(4-Chloro-3-methyl-phenyl)-propylamino]-2-ethyl-benzyl}-azetidine-3-carboxylic acid,
(R)-1-{2-Chloro-5-[(R)-1-(4-chloro-3-methyl-phenyl)-propylamino]-benzyl}-pyrrolidine-3-carboxylic acid,
1-{3-[(S)-1-(4-Chloro-3-methyl-phenyl)-2,2,2-trifluoro-ethylamino]-2-methyl-benzyl}-azetidine-3-carboxylic acid,
3-{3-[(S)-1-(4-Chloro-3-methyl-phenyl)-2,2,2-trifluoro-ethylamino]-2,6-dimethyl-benzylamino}-propionic acid,
1-{5-[(R)-1-(4-Chloro-3,5-dimethyl-phenyl)-propylamino]-2-methyl-benzyl}-azetidine-3-carboxylic acid,
(R)-1-{5-[(R)-1-(4-Chloro-3,5-dimethyl-phenyl)-propylamino]-2-methyl-benzyl}-pyrrolidine-3-carboxylic acid,
(R)-1-{2-Chloro-5-[(R)-1-(4-chloro-3,5-dimethyl-phenyl)-propylamino]-benzyl}-pyrrolidine-3-carboxylic acid,
(R)-1-{5-[(R)-1-(4-Chloro-3,5-dimethyl-phenyl)-ethylamino]-2-methyl-benzyl}-pyrrolidine-3-carboxylic acid,
3-{5-[(R)-1-(4-Chloro-3,5-dimethyl-phenyl)-propylamino]-2-methyl-benzylamino}-propionic acid,
(R)-1-{2-Chloro-5-[(R)-1-(4-chloro-3,5-dimethyl-phenyl)-ethylamino]-benzyl}-pyrrolidine-3-carboxylic acid,
3-{5-[(R)-1-(4-Chloro-3,5-dimethyl-phenyl)-ethylamino]-2-methyl-benzylamino}-propionic acid,
3-{2-Chloro-5-[(R)-1-(4-chloro-3,5-dimethyl-phenyl)-propylamino]-benzylamino}-propionic acid,
(R)-3-{5-[(R)-1-(4-Chloro-3,5-dimethyl-phenyl)-propylamino]-2-methyl-benzylamino}-2-methyl-propionic acid,
3-{5-[(S)-1-(4-Chloro-3,5-dimethyl-phenyl)-2,2,2-trifluoro-ethylamino]-2-methyl-benzylamino}-propionic acid,
3-{2-Chloro-5-[(S)-1-(4-chloro-3,5-dimethyl-phenyl)-2,2,2-trifluoro-ethylamino]-benzylamino}-propionic acid,
3-{2-Chloro-5-[(S)-1-(4-chloro-3-methyl-phenyl)-2,2,2-trifluoro-ethylamino]-benzylamino}-propionic acid,
3-{2-Chloro-5-[(R)-1-(4-chloro-3,5-dimethyl-phenyl)-propylamino]-benzylamino}-propionic acid,
1-{2-[(R)-1-(4-Chloro-3-methyl-phenyl)-propylamino]-5-fluoro-pyridin-4-ylmethyl)-azetidine-3-carboxylic acid, (R)-1-{5-Chloro-2-[(R)-1-(4-chloro-3-methyl-phenyl)-propylamino]-pyridin-4-ylmethyl}-pyrrolidine-3-carboxylic acid,
(R)-1-{5-[(R)-1-(4-Chloro-3-methyl-phenyl)-propylamino]-2-methyl-pyridin-3-ylmethyl}-pyrrolidine-3-carboxylic acid, and
1-{5-Chloro-2-[(R)-1-(4-chloro-3-methyl-phenyl)-propylamino]pyridin-4-ylmethyl}-3-methyl-pyrrolidine-3-carboxylic acid, Embodiment 24 describes a compound of embodiment 16 or 17 or a pharmaceutically acceptable salt thereof, which is selected from:
3-({5-Chloro-2-[(R)-1-(4-chloro-3-methyl-phenyl)-propylamino]-pyridin-4-ylmethyl)-amino)-propionic acid,
(R)-1-{5-Chloro-2-[(R)-1-(4-chloro-3,5-dimethyl-phenyl)-propylamino]-pyridin-4-ylmethyl)-pyrrolidine-3-carboxylic acid,
(R)-1-{2-[(R)-1-(4-Chloro-3-methyl-phenyl)-propylamino]-5-methyl-pyridin-4-ylmethyl}-pyrrolidine-3-carboxylic acid,
1-{2-Chloro-5-[(R)-1-(4-chloro-3,5-dimethyl-phenyl)-propylamino]-benzyl}-azetidine-3-carboxylic acid,
1-{2-Chloro-5-[(R)-1-(4-chloro-3-methyl-phenyl)-propylamino]-benzyl}-azetidine-3-carboxylic acid,
1-{2-Chloro-5-[(R)-1-(4-chloro-3-methyl-phenyl)-2-methyl-propylamino]-benzyl}-azetidine-3-carboxylic acid,
1-{2-Chloro-5-[(R)-1-(4-chloro-3,5-dimethyl-phenyl)-2-methyl-propylamino]-benzyl}-azetidine-3-carboxylic acid,
1-{2-Chloro-5-[(S)-1-(4-chloro-3-methyl-phenyl)-2,2,2-trifluoro-ethylamino]-benzyl}-3-methyl-azetidine-3-carboxylic acid,
1-{2-Chloro-5-[(R)-1-(4-chloro-3,5-dimethyl-phenyl)-propylamino]-benzyl}-3-methyl-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{5-[(S)-1-(4-Chloro-3-methyl-phenyl)-2,2,2-trifluoro-ethylamino]-2-trifluoromethyl-benzyl}-azetidine-3-carboxylic acid,
1-{5-[(S)-1-(4-Chloro-3-methyl-phenyl)-2,2,2-trifluoro-ethylamino]-2-methyl-benzyl}-azetidine-3-carboxylic acid,
1-{5-[(S)-1-(4-Chloro-3-methyl-phenyl)-2,2,2-trifluoro-ethylamino]-2-fluoro-benzyl}-azetidine-3-carboxylic acid,
1-{2-Chloro-5-[(S)-1-(4-chloro-3-methyl-phenyl)-2,2,2-trifluoro-ethylamino]-benzyl}-pyrrolidine-3-carboxylic acid,
3-((S)-1-{3-[(S)-1-(4-Chloro-3-methyl-phenyl)-2,2,2-trifluoro-ethylamino]-phenyl}-ethylamino)-propionic acid
1-{6-[(R)-1-(4-Chloro-3-methyl-phenyl)-propylamino]-pyridin-2-ylmethyl}-azetidine-3-carboxylic acid,
1-{2-[(R)-1-(4-Chloro-3-methyl-phenyl)-propylamino]-pyridin-4-ylmethyl}-azetidine-3-carboxylic acid,
1-(3-{[(R)-(4-Chloro-3-methyl-phenyl)-cyclobutyl-methyl]-amino}-benzyl)-azetidine-3-carboxylic acid,
1-(3-{[(S)-(4-Chloro-3-methyl-phenyl)-cyclobutyl-methyl]-amino}-benzyl)-azetidine-3-carboxylic acid,
1-{4-[(R)-1-(4-Chloro-3-methyl-phenyl)-propylamino]-pyridin-2-ylmethyl}-azetidine-3-carboxylic acid,
1-{5-Chloro-2-[(R)-1-(4-chloro-3-methyl-phenyl)-propylamino]-pyridin-4-ylmethyl}-azetidine-3-carboxylic acid,
3-{5-[(R)-1-(4-Chloro-3,5-dimethyl-phenyl)-propylamino]-2-methyl-benzylamino}-2,2-dimethyl-propionic acid,
(S)-3-{5-[(R)-1-(4-Chloro-3,5-dimethyl-phenyl)-propylamino]-2-methyl-benzylamino}-2-methyl-propionic acid,
3-{5-[(R)-1-(4-Chloro-3,5-dimethyl-phenyl)-propylamino]-2-methyl-benzyl}-methyl-amino)-propionic acid,
1-{5-[(S)-1-(4-Chloro-3-methyl-phenyl)-2,2,2-trifluoro-ethylamino]-2-methyl-benzyl}-3-methyl-pyrrolidine-3-carboxylic acid,
(R)-1-{5-Chloro-2-[(S)-1-(4-chloro-3-methyl-phenyl)-2,2,2-trifluoro-ethylamino]-pyridin-4-ylmethyl}-pyrrolidine-3-carboxylic acid,
3-({5-Chloro-2-[(S)-1-(4-chloro-3-methyl-phenyl)-2,2,2-trifluoro-ethylamino]-pyridin-4-ylmethyl}-amino)-propionic acid,
1-{5-Chloro-2-[(R)-1-(4-chloro-3-methyl-phenyl)-propylamino]pyridin-4-ylmethyl}-3-methyl-pyrrolidine-3-carboxylic acid (single stereoisomer A), and
1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer B).

Embodiment 25 describes a compound of formula (I) or a compound of formula (II) according to embodiment 16 or 17 or a pharmaceutically acceptable salt thereof for use as a medicament, in particular for use in the treatment and/or prevention of diseases or disorders mediated by lymphocytes interactions.

Embodiment 26 describes a method for preventing or treating diseases or disorders which are mediated by lymphocytes interactions, in a subject in need of such treatment or prevention, which method comprises administering to said subject an effective amount of a compound of formula (I) or a compound of formula (II) in accordance to the definition of embodiment 16 or 17 or a pharmaceutically acceptable salt thereof.

The invention claimed is:
1. A compound of formula (I) or a pharmaceutically acceptable salt thereof;

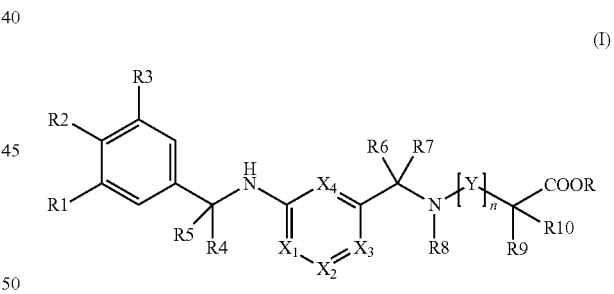

wherein,
R1 is hydrogen, halogen or $C_1$-$C_6$ alkyl optionally substituted by halogen;
R2 is halogen, $C_1$-$C_6$ alkyl optionally substituted by halogen, cyano, or $C_1$-$C_6$ alkoxy optionally substituted by halogen;
or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, and halogen;
R3 is hydrogen, halogen or $C_1$-$C_6$ alkyl optionally substituted by halogen;
R4 is hydrogen, $C_3$-$C_6$ cycloalkyl or $C_1$-$C_6$ alkyl optionally substituted by halogen;

R5 is hydrogen or $C_1$-$C_6$ alkyl;

R6 and R7 are independently selected from H and $C_1$-$C_6$ alkyl or they may form together with the carbon atom to which they are attached a 3-7 membered saturated carbocyclic ring;

R8 and R9 are independently selected from H and $C_1$-$C_6$ alkyl, or R8 and R9 may form together with the atoms to which they are attached a 4-7 membered heterocyclic ring, optionally substituted one or more times by $C_1$-$C_6$-alkyl optionally substituted by halogen, trifluoromethyl, hydroxy, or amino;

n=1, 2, 3 or 4;

R10 is hydrogen, $C_1$-$C_6$ alkyl, amino, hydroxy or $C_1$-$C_6$ alkoxy;

R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl optionally substituted by $C_1$-$C_6$ alkyl, $C_1$-$C_6$ alkoxy, halogen or hydroxy, $X_1$, $X_2$, $X_3$ and $X_4$, are each independently selected from N or CR11, R11 in each case being independently selected from H, halo, cyano, $C_1$-$C_6$ alkoxy, $C_1$-$C_6$ alkyl optionally substituted by halo, or —$SO_2$—$C_1$-$C_6$ alkyl; and Y stands in each occurrence independently for CR12R13 wherein R12 and R13 are independently selected from H and $C_1$-$C_6$ alkyl.

2. A compound of formula (II) or a pharmaceutically acceptable salt thereof,

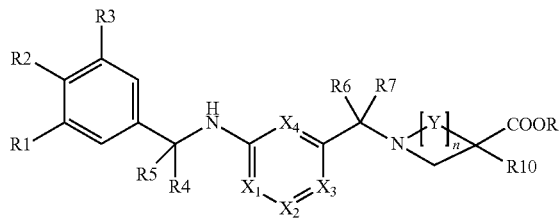

(II)

wherein

R1 is hydrogen, halogen or $C_1$-$C_6$ alkyl optionally substituted by halogen;

R2 is halogen, $C_1$-$C_6$ alkyl optionally substituted by halogen, cyano, or $C_1$-$C_6$ alkoxy optionally substituted by halogen;

or R1 and R2 together with the C-atoms to which they are attached form an aryl ring with 6-10 carbon atoms, which may optionally be substituted by 1-4 substituents selected from cyano, $C_1$-$C_4$-alkyl optionally substituted by halogen, $C_1$-$C_4$-alkoxy optionally substituted by halogen, and halogen;

R3 is hydrogen, halogen or $C_1$-$C_6$ alkyl optionally substituted by halogen;

R4 is hydrogen, $C_3$-$C_6$ cycloalkyl or $C_1$-$C_6$ alkyl optionally substituted by halogen;

R5 is hydrogen or $C_1$-$C_6$ alkyl;

R6 and R7 are independently selected from H and $C_1$-$C_6$ alkyl, or they may form together with the carbon atom to which they are attached a 3-7 membered saturated carbocyclic ring;

n=1, 2, 3 or 4;

R10 is hydrogen, $C_1$-$C_6$ alkyl, amino, hydroxy or $C_1$-$C_6$ alkoxy;

R is selected from H; phenyl being optionally substituted by $C_1$-$C_6$ alkyl, $C_1$-$C_6$ alkoxy, halogen or hydroxy; and $C_1$-$C_6$ alkyl optionally substituted by $C_1$-$C_6$ alkoxy, halogen, hydroxy, or phenyl, said phenyl being optionally substituted by $C_1$-$C_6$ alkyl, $C_1$-$C_6$ alkoxy, halogen or hydroxy;

$X_1$, $X_2$, $X_3$ and $X_4$, are each independently selected from N or CR11,

R11 in each case being independently selected from H, halo, cyano, $C_1$-$C_6$ alkoxy, $C_1$-$C_6$ alkyl optionally substituted by halo, or —$SO_2$—$C_1$-$C_6$ alkyl; and Y stands in each occurrence independently for CR12R13 wherein R12 and R13 are independently selected from H and $C_1$-$C_6$ alkyl optionally substituted by halogen.

3. A compound of claim 1 or 2 or a pharmaceutically acceptable salt thereof, wherein R1 and R stand for hydrogen.

4. A compound of claim 1 or 2, or a pharmaceutically acceptable salt thereof, wherein n is 2.

5. A compound of claim 1 or 2, wherein $X_3$ is CR11 and wherein R11 stands for methyl, or a pharmaceutically acceptable salt thereof.

6. A compound in accordance to claim 1 or 2 or a pharmaceutically acceptable salt thereof, wherein R4 is trifluoromethyl and R5 is hydrogen.

7. A compound of claim 1 or 2 or a pharmaceutically acceptable salt thereof, which is selected from:

1-{3-[1-(4-Chloro-3-methyl-phenyl)-ethylamino]-benzyl}-azetidine-3-carboxylic acid, 1-{3-[1-(4-Chloro-3-methyl-phenyl)-propylamino]-benzyl}-azetidine-3-carboxylic acid, 1-{3-[(R)-1-(4-Chloro-3-methyl-phenyl)-propylamino]-benzyl}-azetidine-3-carboxylic acid, 1-{5-[1-(4-Chloro-3-methyl-phenyl)-propylamino]-2-methyl-benzyl}-azetidine-3-carboxylic acid, 1-{3-[1-(4-Chloro-3-methyl-phenyl)-propylamino]-4-methyl-benzyl}-azetidine-3-carboxylic acid, 1-(1-{3-[(R)-1-(4-Chloro-3-methyl-phenyl)-propylamino]-phenyl}-ethyl)azetidine-3-carboxylic acid, 1-{3-[1-(4-Chloro-3-methyl-phenyl)-propylamino]-2-methyl-benzyl}-azetidine-3-carboxylic acid, 1-{3-[(R)-1-(4-Chloro-3-methyl-phenyl)-propylamino]-benzyl}-3-methyl-azetidine-3-carboxylic acid, 1-{3-[1-(4-Chloro-3-methyl-phenyl)-propylamino]-5-methyl-benzyl}-azetidine-3-carboxylic acid, 1-(1-{5-[1-(4-Chloro-3-methyl-phenyl)-propylamino]-2-methyl-phenyl}-ethyl)-azetidine-3-carboxylic acid, (R)-1-{3-[(R)-1-(4-Chloro-3-methyl-phenyl)-propylamino]-benzyl}-pyrrolidine-3-carboxylic acid, (S)-1-{3-[(R)-1-(4-Chloro-3-methyl-phenyl)-propylamino]-benzyl}-pyrrolidine-3-carboxylic acid, 1-(1-(3-[(R)-1-(4-Chloro-3-methyl-phenyl)-propylamino]-phenyl}-propyl)-azetidine-3-carboxylic acid, (R)-1-{3-[1-(4-Chloro-3-methyl-phenyl)-propylamino]-2-methyl-benzyl}-pyrrolidine-3-carboxylic acid, (R)-1-{3-[1-(4-Chloro-3-methyl-phenyl)-propylamino]-5-methyl-benzyl}-pyrrolidine-3-carboxylic acid, 1-{3-[(R)-1-(4-Chloro-3-methyl-phenyl)-propylamino]-benzyl}-3-ethyl-azetidine-3-carboxylic acid, 1-{3-[1-(4-Chloro-3-methyl-phenyl)-2-methyl-propylamino]-benzyl}-azetidine-3-carboxylic acid, 1-{3-[(R)-1-(4-Chloro-3,5-dimethyl-phenyl)-propylamino]-benzyl}-azetidine-3-carboxylic acid, 1-{3-[(R)-1-(4-Chloro-3,5-dimethyl-phenyl)-propylamino]-benzyl}-azetidine-3-carboxylic acid, 1-{3-[(R)-1-(5-Chloro-naphthalen-2-yl)-propylamino]-benzyl}-azetidine-3-carboxylic acid, (R)-1-{5-[(S)-1-(4-Chloro-3-methyl-phenyl)-2,2,2-trifluoro-ethylamino]-2-methyl-benzyl}-pyrrolidine-3-carboxylic acid,
1-{5-[(R)-1-(4-Chloro-3-methyl-phenyl)-propylamino]-2-methyl-benzyl}-azetidine-3-carboxylic acid,
(R)-1-{5-[(R)-1-(4-Chloro-3-methyl-phenyl)-propylamino]-2-methyl-benzyl}-pyrrolidine-3-carboxylic acid,
1-{3-[(R)-1-(4-Chloro-3-methyl-phenyl)-propylamino]-2-fluoro-benzyl}-azetidine-3-carboxylic acid,
(R)-1-{3-[(R)-1-(4-Chloro-3-methyl-phenyl)-propylamino]-2-fluoro-benzyl}-pyrrolidine-3-carboxylic acid,
1-{3-[(R)-1-(4-Chloro-3-methyl-phenyl)-propylamino]-4-fluoro-benzyl}-azetidine-3-carboxylic acid,
(R)-1-{3-[(R)-1-(4-Chloro-3-methyl-phenyl)-propylamino]-4-fluoro-benzyl}-pyrrolidine-3-carboxylic acid,
1-{5-[(R)-1-(4-Chloro-3-methyl-phenyl)-propylamino]-2-methyl-benzyl}-3-methyl-azetidine-3-carboxylic acid,
(R)-1-{2-Chloro-5-[(S)-1-(4-chloro-3-methyl-phenyl)-2,2,2-trifluoro-ethylamino]-benzyl}-pyrrolidine-3-carboxylic acid,
(R)-1-{3-[(S)-1-(4-Chloro-3-methyl-phenyl)-2,2,2-trifluoro-ethylamino]-2,6-dimethyl-benzyl}-pyrrolidine-3-carboxylic acid,
1-{3-[(S)-1-(4-Chloro-3-methyl-phenyl)-2,2,2-trifluoro-ethylamino]-2,6-dimethyl-benzyl}-azetidine-3-carboxylic acid,
(R)-1-{3-[(R)-1-(4-Chloro-3-methyl-phenyl)-propylamino]-2,6-dimethyl-benzyl}-pyrrolidine-3-carboxylic acid,
1-{3-[(R)-1-(4-Chloro-3-methyl-phenyl)-propylamino]-2,6-dimethyl-benzyl}-azetidine-3-carboxylic acid,
(R)-1-{5-[(S)-1-(4-Chloro-3-methyl-phenyl)-2,2,2-trifluoro-ethylamino]-2-ethyl-benzyl}-pyrrolidine-3-carboxylic acid,
1-{5-[(S)-1-(4-Chloro-3-methyl-phenyl)-2,2,2-trifluoro-ethylamino]-2-ethyl-benzyl}-azetidine-3-carboxylic acid,
(R)-1-{5-[(R)-1-(4-Chloro-3-methyl-phenyl)-propylamino]-2-ethyl-benzyl}-pyrrolidine-3-carboxylic acid,
1-{5-[(R)-1-(4-Chloro-3-methyl-phenyl)-propylamino]-2-ethyl-benzyl}-azetidine-3-carboxylic acid,
(R)-1-{2-Chloro-5-[(R)-1-(4-chloro-3-methyl-phenyl)-propylamino]-benzyl}-pyrrolidine-3-carboxylic acid,
1-{3-[(S)-1-(4-Chloro-3-methyl-phenyl)-2,2,2-trifluoro-ethylamino]-2-methyl-benzyl}-azetidine-3-carboxylic acid,
3-{3-[(S)-1-(4-Chloro-3-methyl-phenyl)-2,2,2-trifluoro-ethylamino]-2,6-dimethyl-benzylamino}-propionic acid,
1-{5-[(R)-1-(4-Chloro-3,5-dimethyl-phenyl)-propylamino]-2-methyl-benzyl}-azetidine-3-carboxylic acid,
(R)-1-{5-[(R)-1-(4-Chloro-3,5-dimethyl-phenyl)-propylamino]-2-methyl-benzyl}-pyrrolidine-3-carboxylic acid,
(R)-1-{2-Chloro-5-[(R)-1-(4-chloro-3,5-dimethyl-phenyl)-propylamino]-benzyl}-pyrrolidine-3-carboxylic acid,
(R)-1-{5-[(R)-1-(4-Chloro-3,5-dimethyl-phenyl)-ethylamino]-2-methyl-benzyl}-pyrrolidine-3-carboxylic acid,
3-{5-[(R)-1-(4-Chloro-3,5-dimethyl-phenyl)-propylamino]-2-methyl-benzylamino}-propionic acid,
(R)-1-{2-Chloro-5-[(R)-1-(4-chloro-3,5-dimethyl-phenyl)-ethylamino]-benzyl}-pyrrolidine-3-carboxylic acid,
3-{5-[(R)-1-(4-Chloro-3,5-dimethyl-phenyl)-ethylamino]-2-methyl-benzylamino}-propionic acid,
3-{2-Chloro-5-[(R)-1-(4-chloro-3,5-dimethyl-phenyl)-propylamino]-benzylamino}-propionic acid,
(R)-3-{5-[(R)-1-(4-Chloro-3,5-dimethyl-phenyl)-propylamino]-2-methyl-benzylamino}-2-methyl-propionic acid,
3-{5-[(S)-1-(4-Chloro-3,5-dimethyl-phenyl)-2,2,2-trifluoro-ethylamino]-2-methyl-benzylamino}-propionic acid,
3-{2-Chloro-5-[(S)-1-(4-chloro-3,5-dimethyl-phenyl)-2,2,2-trifluoro-ethylamino]-benzylamino}-propionic acid,
3-{2-Chloro-5-[(S)-1-(4-chloro-3-methyl-phenyl)-2,2,2-trifluoro-ethylamino]-benzylamino}-propionic acid,
3-{2-Chloro-5-[(R)-1-(4-chloro-3,5-dimethyl-phenyl)-propylamino]-benzylamino}-propionic acid,
1-{2-[(R)-1-(4-Chloro-3-methyl-phenyl)-propylamino]-5-fluoro-pyridin-4-ylmethyl}-azetidine-3-carboxylic acid,
(R)-1-{5-Chloro-2-[(R)-1-(4-chloro-3-methyl-phenyl)-propylamino]-pyridin-4-ylmethyl}-pyrrolidine-3-carboxylic acid,
(R)-1-{5-[(R)-1-(4-Chloro-3-methyl-phenyl)-propylamino]-2-methyl-pyridin-3-ylmethyl}-pyrrolidine-3-carboxylic acid,
1-{5-Chloro-2-[(R)-1-(4-chloro-3-methyl-phenyl)-propylamino]-pyridin-4-ylmethyl}-3-methyl-pyrrolidine-3-carboxylic acid,
3-({5-Chloro-2-[(R)-1-(4-chloro-3-methyl-phenyl)-propylamino]-pyridin-4-ylmethyl}-amino)-propionic acid,
(R)-1-{5-Chloro-2-[(R)-1-(4-chloro-3,5-dimethyl-phenyl)-propylamino-]-pyridin-4-ylmethyl}-pyrrolidine-3-carboxylic acid,
(R)-1-{2-[(R)-1-(4-Chloro-3-methyl-phenyl)-propylamino]-5-methyl-pyridin-4-ylmethyl}-pyrrolidine-3-carboxylic acid,
1-{2-Chloro-5-[(R)-1-(4-chloro-3,5-dimethyl-phenyl)-propylamino]-benzyl}-azetidine-3-carboxylic acid,
1-{2-Chloro-5-[(R)-1-(4-chloro-3-methyl-phenyl)-propylamino]-benzyl}-azetidine-3-carboxylic acid,
1-{2-Chloro-5-[(R)-1-(4-chloro-3-methyl-phenyl)-2-methyl-propylamino]-benzyl}-azetidine-3-carboxylic acid,
1-{2-Chloro-5-[(R)-1-(4-chloro-3,5-dimethyl-phenyl)-2-methyl-propylamino]-benzyl}-azetidine-3-carboxylic acid,
1-{2-Chloro-5-[(S)-1-(4-chloro-3-methyl-phenyl)-2,2,2-trifluoro-ethylamino]-benzyl}-3-methyl-azetidine-3-carboxylic acid,
1-{2-Chloro-5-[(R)-1-(4-chloro-3,5-dimethyl-phenyl)-propylamino]-benzyl}-3-methyl-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{3-[(S)-1-(4-Chloro-3-methyl-phenyl)-2,2,2-trifluoro-ethylamino]-benzyl}-azetidine-3-carboxylic acid,
1-{5-[(S)-1-(4-Chloro-3-methyl-phenyl)-2,2,2-trifluoro-ethylamino]-2-trifluoromethyl-benzyl}-azetidine-3-carboxylic acid,
1-{5-[(S)-1-(4-Chloro-3-methyl-phenyl)-2,2,2-trifluoro-ethylamino]-2-methyl-benzyl}-azetidine-3-carboxylic acid, 1-{5-[(S)-1-(4-Chloro-3-methyl-phenyl)-2,2,2-trifluoro-ethylamino]-2-fluoro-benzyl}-azetidine-3-carboxylic acid,
1-{2-Chloro-5-[(S)-1-(4-chloro-3-methyl-phenyl)-2,2,2-trifluoro-ethylamino]-benzyl}-pyrrolidine-3-carboxylic acid,
3-((S)-1-{3-[(S)-1-(4-Chloro-3-methyl-phenyl)-2,2,2-trifluoro-ethylamino]-phenyl}-ethylamino)-propionic acid
1-{6-[(R)-1-(4-Chloro-3-methyl-phenyl)-propylamino]-pyridin-2-ylmethyl}-azetidine-3-carboxylic acid,
1-{2-[(R)-1-(4-Chloro-3-methyl-phenyl)-propylamino]-pyridin-4-ylmethyl}-azetidine-3-carboxylic acid,
1-(3-{[(R)-(4-Chloro-3-methyl-phenyl)-cyclobutyl-methyl]-amino}-benzyl)-azetidine-3-carboxylic acid,
1-(3-{[(S)-(4-Chloro-3-methyl-phenyl)-cyclobutyl-methyl]-amino}-benzyl)-azetidine-3-carboxylic acid,
1-{4-[(R)-1-(4-Chloro-3-methyl-phenyl)-propylamino]-pyridin-2-ylmethyl}-azetidine-3-carboxylic acid,
1-{5-Chloro-2-[(R)-1-(4-chloro-3-methyl-phenyl)-propylamino]-pyridin-4-ylmethyl}-azetidine-3-carboxylic acid,
3-{5-[(R)-1-(4-Chloro-3,5-dimethyl-phenyl)-propylamino]-2-methyl-benzylamino}-2,2-dimethyl-propionic acid,
(S)-3-{5-[(R)-1-(4-Chloro-3,5-dimethyl-phenyl)-propylamino]-2-methyl-benzylamino}-2-methyl-propionic acid,
3-({5-[(R)-1-(4-Chloro-3,5-dimethyl-phenyl)-propylamino]-2-methyl-benzyl}-methyl-amino)-propionic acid,
1-{5-[(S)-1-(4-Chloro-3-methyl-phenyl)-2,2,2-trifluoro-ethylamino]-2-methyl-benzyl}-3-methyl-pyrrolidine-3-carboxylic acid,
(R)-1-{5-Chloro-2-[(S)-1-(4-chloro-3-methyl-phenyl)-2,2,2-trifluoro-ethylamino]-pyridin-4-ylmethyl}-pyrrolidine-3-carboxylic acid,
3-({5-Chloro-2-[(S)-1-(4-chloro-3-methyl-phenyl)-2,2,2-trifluoro-ethylamino]-pyridin-4-ylmethyl}-amino)-propionic acid,
1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer A), and
1-{5-Chloro-2-[(R)-1-(4-chloro-3-methyl-phenyl)-propylamino]-pyridin-4-ylmethyl}-3-methyl-pyrrolidine-3-carboxylic acid (single stereoisomer B).

8. A method for preventing or treating diseases or disorders which are mediated by lymphocytes interactions, in a subject in need of such treatment or prevention, which method comprises administering to said subject an effective amount of a compound of formula (I) or a compound of formula (II) in accordance to the definition of claim 1 or 2 or a pharmaceutically acceptable salt thereof; wherein the diseases or disorders mediated by lymphocytes interactions are selected from the group consisting of transplantation, autoimmune diseases, allergic diseases, inflammatory diseases optionally with underlying aberrant reactions, ischemia/reperfusion injury, cancer, infectious diseases, adult respiratory distress syndrome or viral infections, viral hepatitis, chronic bacterial infection, neurodegenerative diseases, deregulated angiogenesis, inflammatory diseases, endometriosis or chronic asthma, and tumor diseases.

9. The method according to claim 8, wherein said disease or said disorder is selected from an autoimmune disease and a tumor disease.

10. A pharmaceutical combination or a kit, comprising a) a first agent which is a compound of formula (I) or formula (II) as disclosed in claim 1 or claim 2, or a pharmaceutically acceptable salt thereof, and b) at least one co-agent.

11. A pharmaceutical composition, comprising a compound of formula (I) or a compound of formula (II) of claim 1 or claim 2 or a pharmaceutically acceptable salt thereof in association with a pharmaceutically acceptable diluent or carrier therefore.

12. A method of manufacturing a compound of formula (I) in accordance to claim 1, comprising reacting:

(A) a nitro aldehyde derivative of formula (I) with an amine of formula (II) under reductive amination conditions, to furnish the nitro intermediate (iii),

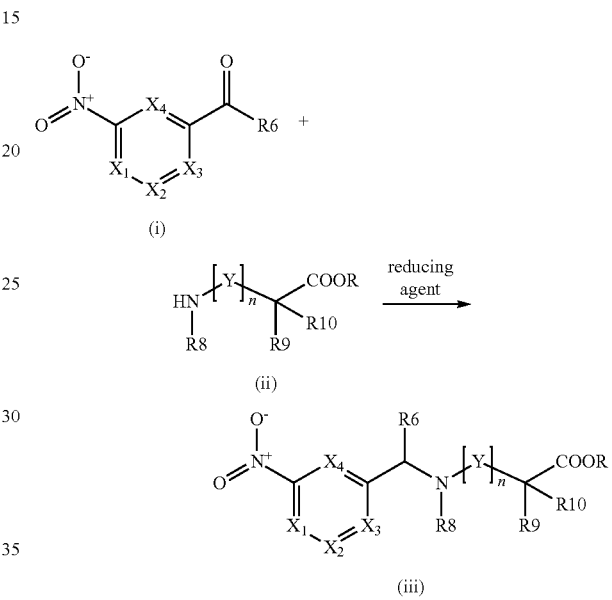

which is converted to the amino-derivative (iv) by chemical reduction

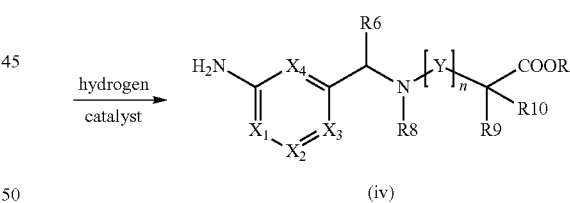

which is further reacted with the keto-derivative (v) under reductive amination conditions to furnish a compound (vi),

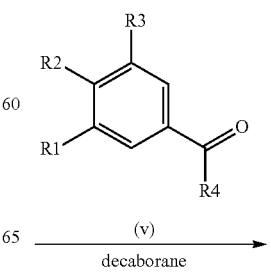

-continued

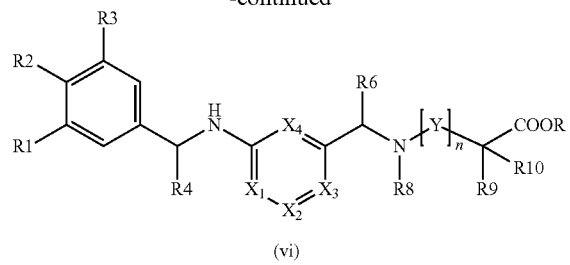

(vi)

which may or may not be cleaved to the acid, by treating ester of formula (vi) with an acid such as hydrochlorid acid or alternatively with a base such as LiOH in water, to a final compound in accordance to the definition of formula (I'):

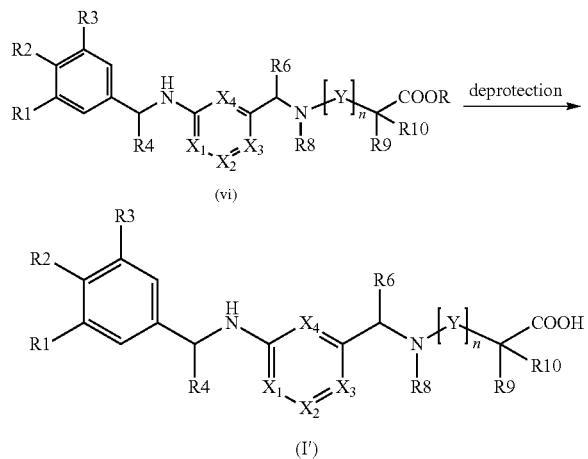

or reacting:

(B) a keto derivative of formula (v) with an amine derivative of formula (vii) under reductive amination conditions to yield the halo-derivative of formula (viii),

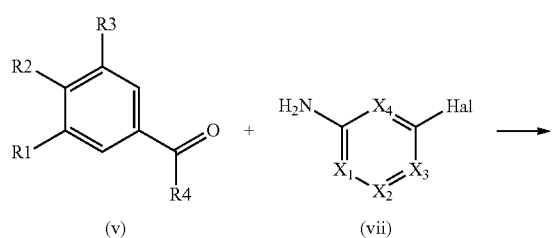

which is converted to the aldehyde of formula (ix) by a halogen metal exchange reaction with an appropriate organolithium reagent, and subsequent quenching with DMF,

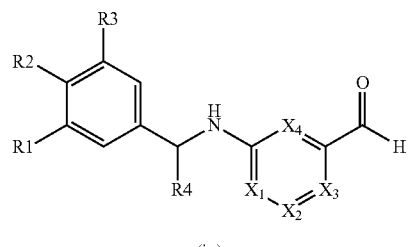

which is reacted with amine of formula (ii) under reductive amination conditions to furnish the ester of formula (vi), or it will furnish the acid of formula (vi) when R=hydrogen,

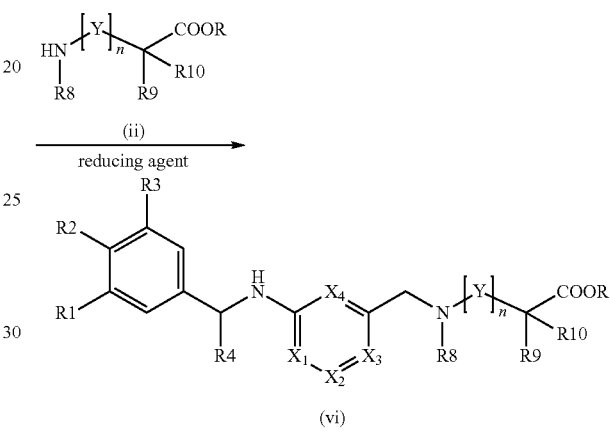

or alternatively, aldehyde of formula (ix) is converted with an appropriate Grignard reagent to furnish the alcohol derivative (x),

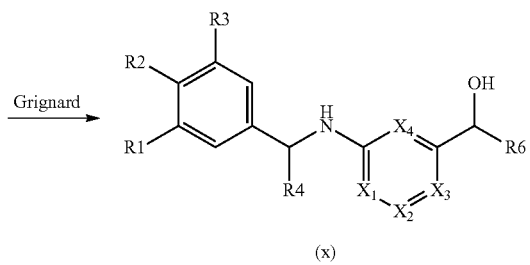

which is converted to the ketone derivative (xi) by an oxidation reaction, typically in the presence of a solvent,

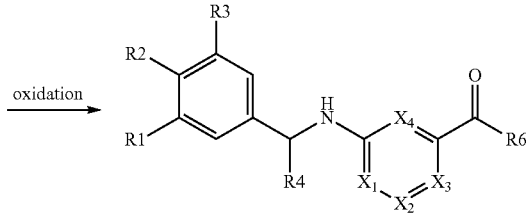

which ketone (xi) is then converted under reductive amination conditions as described hereinbefore with an amine of formula (ii) into final compound of formula (xii), which may be optionally treated for example with an acid, or with a base, to cleave the ester into the carboxlic acid (R=hydrogen);

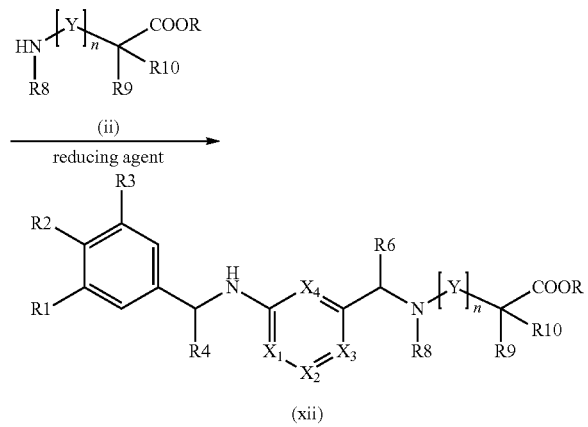

or reacting:

(C) an amine of formula (xiii) with the halo-derivative (xiv) under Buchwald coupling conditions to furnish acetal derivative (xv), wherein each R' independently represents a $C_{1-6}$alkyl, $C_{3-7}$cycloalkyl, benzyl, or wherein both R' with the oxygen atoms to which they are attached form a 5, 6 or 7 membered ring system, such as methylenedioxolane, ethylenedioxolane, propylenedioxolane,

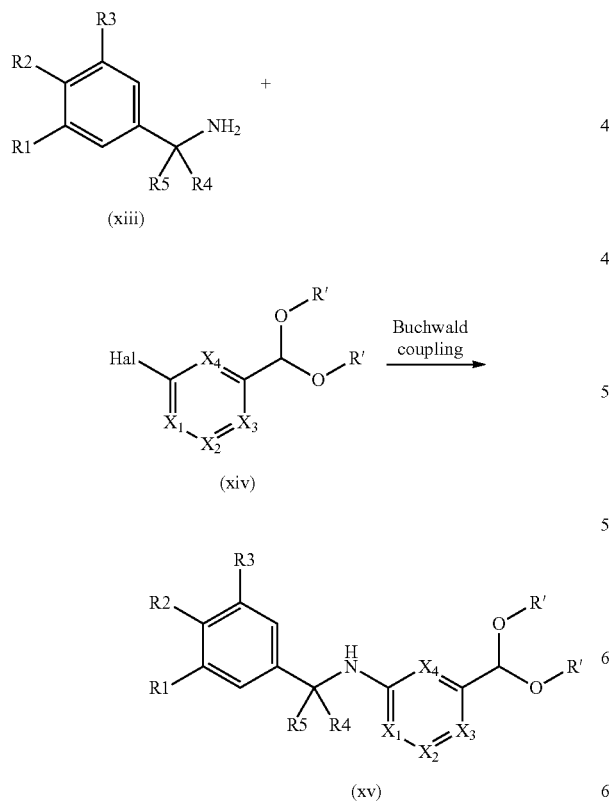

which is deprotected by reacting the acetal-derivative with an acid, to furnish aldehyde (xvi),

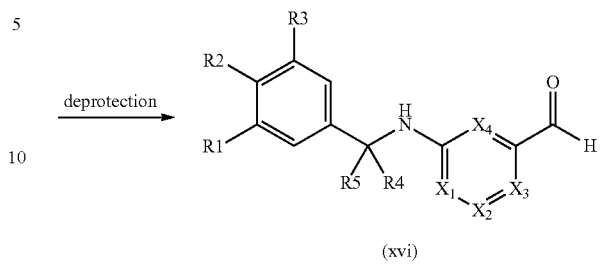

which is reacted with amine-derivative of formula (ii) to furnish final compound of formula (xvii), which may be optionally treated with an acid, or alternatively with a base, to cleave the ester into the carboxlic acid (R=hydrogen);

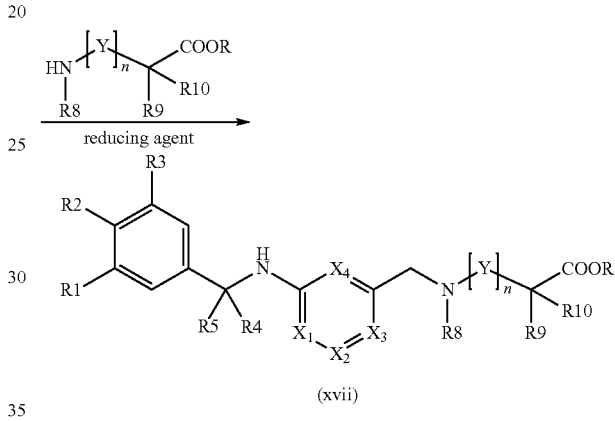

or reacting:

(D) a haloketone of formula (xviii) and an amine of formula (ii) under reductive amination conditions as described hereinbefore to furnish halo-ester intermediate of formula (xix),

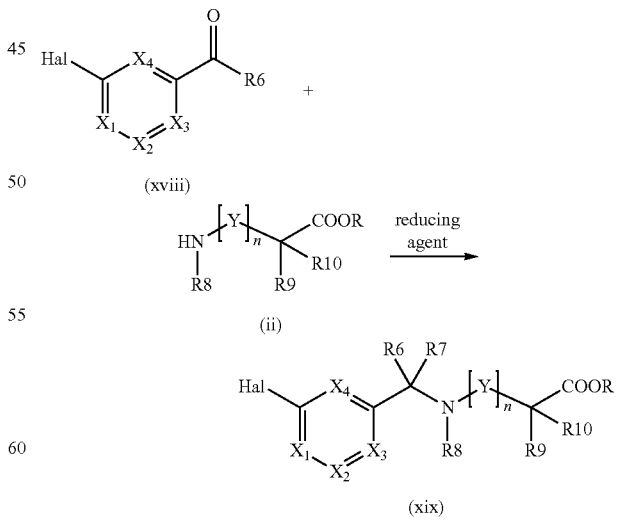

or alternatively a haloamine derivative of formula (xx) is reacted with an acrylic acid derivative (xxi) in the presence of a Lewis acid to furnish the halo-ester intermediate of formula (xix),

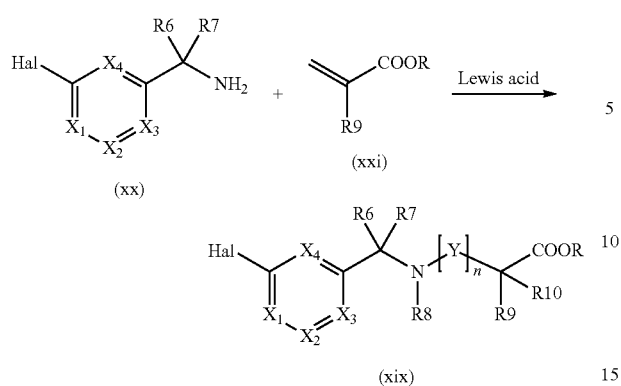

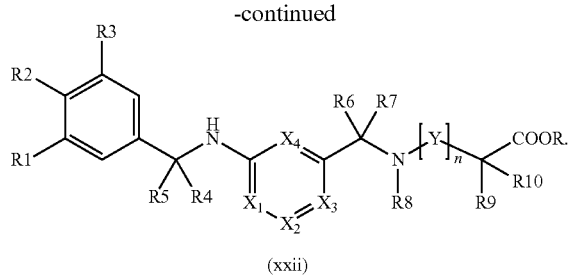

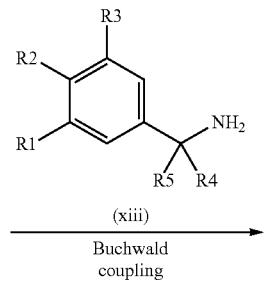

which is reacted with an amine of formula (xiii) under Buchwald reaction conditions, to furnish ester compound (xxii), which may be optionally treated with an acid, to cleave the ester into the carboxlic acid (R=hydrogen)

13. The method according to claim 9 wherein said autoimmune disease is rheumatoid arthritis, systemic lupus erythematosus, inflammatory bowel disease, psoriasis, or multiple sclerosis.

14. The method according to claim 9 wherein said tumor disease is solid tumors, leukemias or other liquid tumors.

15. A pharmaceutical combination or a kit according to claim 10 wherein said co-agent is an immunosuppressant, immunomodulatory, anti-inflammatory, chemotherapeutic or an anti-infectious agent.

16. The method of claim 8, wherein said disease or disorders are selected from the group consisting of rheumatoid arthritis, systemic lupus erythematosus, hashimoto's thyroidis, multiple sclerosis, myasthenia gravis, neuropathic pain, Behcet's disease, Wegener's granulamatosis, ankylosing spondylitis, polymyositis, Chronic Idiopathic Demyelinating Polyneuropathy, diabetes type I or II, vasculitis, pernicious anemia, Sjoegren syndrome, uveitis, psoriasis, Graves ophthalmopathy, and alopecia greata.

\* \* \* \* \*